US011466298B2

(12) United States Patent
De Berardinis et al.

(10) Patent No.: US 11,466,298 B2
(45) Date of Patent: Oct. 11, 2022

(54) METHOD FOR PREPARING PHOSPHORYLATED KETO POLYOLS, DERIVATIVES THEREOF AND USES THEREOF

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE CLERMONT AUVERGNE, Clermont Ferrand (FR); UNIVERSITE D'EVRY VAL D'ESSONNE, Evry (FR)

(72) Inventors: Véronique De Berardinis, Paris (FR); Marcel Salanoubat, Malakoff (FR); Marielle Lemaire, Ceyrat (FR); Christine Guerard-Helaine, Saint Amand Tallende (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE CLERMONT AUVERGNE, Clermont Ferrand (FR); UNIVERSITE D'EVRY VAL D'ESSONNE, Evry (FR)

( * ) Notice: Subject to any disclaimer, the term of this patent is extended or adjusted under 35 U.S.C. 154(b) by 247 days.

(21) Appl. No.: 16/615,427

(22) PCT Filed: May 22, 2018

(86) PCT No.: PCT/EP2018/063400
§ 371 (c)(1),
(2) Date: Nov. 21, 2019

(87) PCT Pub. No.: WO2018/215476
PCT Pub. Date: Nov. 29, 2018

(65) Prior Publication Data
US 2020/0208181 A1 Jul. 2, 2020

(30) Foreign Application Priority Data

May 23, 2017 (EP) .................... 17305604

(51) Int. Cl.
| | |
|---|---|
| *C12P 9/00* | (2006.01) |
| *C07F 9/09* | (2006.01) |
| *C12P 7/26* | (2006.01) |
| *C07H 1/02* | (2006.01) |
| *C07H 3/02* | (2006.01) |
| *C07H 11/04* | (2006.01) |

(52) U.S. Cl.
CPC ....... *C12P 9/00* (2013.01); *C07F 9/09* (2013.01); *C07F 9/091* (2013.01); *C07H 1/02* (2013.01); *C07H 3/02* (2013.01); *C07H 11/04* (2013.01); *C12P 7/26* (2013.01); *C12Y 401/00* (2013.01); *C12Y 401/0204* (2013.01); *C12Y 401/02017* (2013.01); *C12Y 401/02019* (2013.01)

(58) Field of Classification Search
None
See application file for complete search history.

(56) References Cited

U.S. PATENT DOCUMENTS 5,759,825 A * 6/1998 Wong .................... C12P 19/02
536/18.6
2005/0009153 A1 * 1/2005 Sugiyama ............... C12P 13/04
435/121

OTHER PUBLICATIONS

Durrwachter et al., "Enzymatic Aldol Condensation/Isomerization as a Route to Unusual Sugar Derivatives" J am Chem Soc vol. 108 pp. 7812-7818 (Year: 1986).*
List et al., "A Catalytic Enantioselective Route to Hydroxy-Substituted Quaternary Carbon Centers: Resolution of Tertiary Aldols with a Catalytic Antibody" J Am Chem Soc volo. 121 pp. 7283-7291 (Year: 1999).*
Barbas, C. F. III, et al. "Immune Versus Natural Selection: Antibody Aldolases with Enzymic Rates But Broader Scope" *Science*, Dec. 19, 1997, pp. 2085-2092, vol. 278.
Bhanushali, M. et al. "Developing Novel Organocatalyzed Aldol Reactions for the Enantioselective Synthesis of Biologically Active Molecules" *Synthesis*, 2011, pp. 1815-1830, vol. 2011, No. 12.
Oisaki, K. et al. "Catalytic Enantioselective Aldol Reaction to Ketones" *J. Am. Chem. Soc.*, 2006, pp. 7164-7165, vol. 128, No. 22.
Rao, D. et al. "Towards the biotechnological isomerization of branched sugars: $_D$-tagatose-3-epimerase equilibrates both enantiomers of 4-C-methyl-ribulose with both enantiomers of 4-C-methyl-xylulose" *Tetrahedron Letters*, 2008, pp. 3316-3321, vol. 49, No. 20.
Schmidt, N. G. et al. "Building Bridges: Biocatalytic C-C-Bond Formation toward Multifunctional Products" *ACS Catal.*, 2016, pp. 4286-4311, vol. 6, No. 7.
Szarek, W. A. et al. "Oxidation of a Branched-Chain Alditol By *Acetobacter suboxydans*: A Stereospecific Synthesis of $_L$-Dendroketose" *Carbohydrate Research*, 1977, pp. 101-108, vol. 53, No. 1.
Trost, B. M. et al. "The direct catalytic asymmetric aldol reaction" *Chemical Society Reviews*, 2010, pp. 1600-1632, vol. 39, No. 5.
Written Opinion in International Application No. PCT/EP2018/063400, dated Aug. 29, 2018, pp. 1-9.

\* cited by examiner

*Primary Examiner* — Eric Olson
(74) *Attorney, Agent, or Firm* — Saliwanchik, Lloyd & Eisenschenk

(57) ABSTRACT

The present invention relates to a method for preparing phosphorylated keto polyols by biocatalysis and uses thereof.

17 Claims, No Drawings
Specification includes a Sequence Listing.

SEQUENCE LISTING

<160> NUMBER OF SEQ ID NOS: 35

<210> SEQ ID NO 1
<211> LENGTH: 274
<212> TYPE: PRT
<213> ORGANISM: Escherichia coli

<400> SEQUENCE: 1

Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
                20                  25                  30

Leu Thr Leu Arg Leu Asp Asp Ala Asp Ile Ala Pro Tyr His Asp Asn
                35                  40                  45

Phe His Gln Gln Pro Arg Tyr Ile Pro Leu Ser Gln Pro Met Pro Leu
 50                  55                  60

Leu Ala Asn Thr Pro Phe Ile Val Thr Gly Ser Gly Lys Phe Phe Arg
 65                  70                  75                  80

Asn Val Gln Leu Asp Pro Ala Ala Asn Leu Gly Ile Val Lys Val Asp
                85                  90                  95

Ser Asp Gly Ala Gly Tyr His Ile Leu Trp Gly Leu Thr Asn Glu Ala
                100                 105                 110

Val Pro Thr Ser Glu Leu Pro Ala His Phe Leu Ser His Cys Glu Arg
                115                 120                 125

Ile Lys Ala Thr Asn Gly Lys Asp Arg Val Ile Met His Cys His Ala
                130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Glu
                180                 185                 190

Ile Gly Gln Ala Thr Ala Gln Glu Met Gln Lys His Ser Leu Val Leu
                195                 200                 205

Trp Pro Phe His Gly Val Phe Gly Ser Gly Pro Thr Leu Asp Glu Thr
210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
                260                 265                 270

Ala Leu

<210> SEQ ID NO 2
<211> LENGTH: 278
<212> TYPE: PRT
<213> ORGANISM: Listeria welshimeri

<400> SEQUENCE: 2

Met Tyr Ser Ile Tyr Glu Ala Pro Phe Met Lys Glu Met Cys Glu Met
1               5                   10                  15

Thr Gln Asn Leu Trp Arg Asn Gly Trp Ala Glu Lys Asn Gly Gly Asn
                20                  25                  30

Ile Ser Gln Leu Leu Glu Ala Ser Glu Ile Lys His Tyr Leu Asp Thr
                35                  40                  45

Asp Arg Tyr Leu Trp Thr Glu Pro Leu Gly Phe Asp Ala Ser Pro Leu
 50                  55                  60

Ala Gly Asn Val Phe Leu Val Ser Gly Ser Gly Lys Tyr Phe Lys Asn
 65                  70                  75                  80

Val Gln Lys Asn Pro Ala Asp Asn Leu Cys Ile Ile Lys Val Ser Ser
                85                  90                  95

Asp Gly Ala Ser Tyr His Leu Leu Trp Gly Leu Glu Asn Gly Gly Arg
                100                 105                 110

```
Pro Thr Ser Glu Leu Ala Ser His Leu Lys Cys His Ile Val Arg Leu
            115                 120                 125

Ser Gln Asp Pro Asp His Arg Val Ile Leu His Thr His Ala Thr Ala
    130                 135                 140

Val Ser Ala Met Thr Phe Val His Asp Leu Asp Glu Ala Lys Phe Thr
145                 150                 155                 160

Arg Thr Leu Trp Gln Met Ile Thr Glu Cys Leu Val Val Phe Pro Asp
                165                 170                 175

Gly Val Ala Val Val Pro Trp Met Val Ala Gly Thr Asn Glu Leu Gly
            180                 185                 190

Glu Ala Ser Ala Ala Lys Met Asn Asp Ser Arg Ile Val Val Trp Ala
        195                 200                 205

His His Gly Ile Met Gly Ala Gly Thr Thr Met Asp Asp Ala Phe Gly
    210                 215                 220

Leu Val Glu Thr Val Glu Lys Ala Ala Lys Ile Tyr Met Gln Ile Ala
225                 230                 235                 240

His Phe Pro Thr Gly Ile Lys Gln Ala Ile Thr Asp Glu Glu Leu Val
                245                 250                 255

Ala Leu Ala Glu Arg Phe Asn Val Val Pro Lys Ala Gly Ile Leu Lys
            260                 265                 270

Glu Ala Gly Gly Val Lys
        275

<210> SEQ ID NO 3
<211> LENGTH: 270
<212> TYPE: PRT
<213> ORGANISM: Clostridium hylemonae

<400> SEQUENCE: 3

Met Lys Asn Ile Leu Glu Ser Pro Ile Ile Thr Glu Ile Cys Asp Met
1               5                   10                  15

Thr Ala Asn Met Tyr Arg Leu Gly Trp Asp Glu Arg Asn Gly Gly Asn
            20                  25                  30

Ile Ser Trp Leu Leu Asp Glu Gln Glu Leu Ala Glu Tyr Leu Asp Leu
        35                  40                  45

Ser Gln Val Ile Arg Asn Ile Pro Ile Ala Phe Asp Ala Ala Glu Leu
    50                  55                  60

Ala Gly Arg Ile Phe Leu Val Thr Gly Thr Gly Lys Tyr Phe Lys Asn
65                  70                  75                  80

Val Thr Gly Asn Pro Gln Glu Asn Leu Gly Ile Val Arg Val Ala Ser
                85                  90                  95

Asn Gly Thr Glu Leu Glu Leu Leu Trp Gly Phe Glu Gly Gly Ala Leu
            100                 105                 110

Pro Thr Ser Glu Phe Pro Thr His Leu Met Asn His Met Ala Arg Leu
        115                 120                 125

Lys Ala Asp Pro Glu His Arg Ile Val Met His Cys His Pro Ala Asn
    130                 135                 140

Thr Ile Ala Met Thr Phe Val His Ser Ile Asp Asp Arg Glu Phe Thr
145                 150                 155                 160

Cys Thr Leu Trp Gln Met Ile Thr Glu Cys Ile Val Val Phe Pro Asp
                165                 170                 175

Gly Val Gly Val Val Pro Trp Met Val Ser Gly Thr Asn Asp Ile Gly
            180                 185                 190

Glu Ala Thr Ala Arg Lys Ile Lys Asp Cys Arg Leu Val Val Trp Ala
        195                 200                 205
```

```
His His Gly Ile Phe Gly Thr Gly Arg Thr Leu Asp Glu Ala Phe Gly
    210                 215                 220

Leu Ile Glu Thr Val Glu Lys Ala Ala Gln Ile Tyr Met Lys Ile Ala
225                 230                 235                 240

His Leu Asp Ile Lys Asn Thr Ile Pro Lys Glu Gln Leu Lys Ala Leu
            245                 250                 255

Ala Glu Thr Phe His Ala Val Pro Arg Glu Gly Trp Leu Asp
        260                 265                 270

<210> SEQ ID NO 4
<211> LENGTH: 296
<212> TYPE: PRT
<213> ORGANISM: Lactobacillus rhamnosus

<400> SEQUENCE: 4

Met Asp Asn Lys Lys Gln Phe Leu Asn Pro Glu Tyr Thr Gln Ser Phe
1               5                   10                  15

Val Glu Ser Pro Tyr Val Ala Gln Met Arg Lys Val Thr Trp Asn Leu
            20                  25                  30

Tyr Gln His Gly Trp Asp Glu Arg Asn Gly Gly Asn Val Ser Tyr Arg
        35                  40                  45

Leu Thr Ala Ala Glu Ile Ala Pro Tyr Gly Asp Val His Glu Val Lys
50                  55                  60

Arg Asn Leu Pro Ile Lys Phe Asp Ala Ser Glu Leu Ala Gly Gln Tyr
65                  70                  75                  80

Phe Leu Val Thr Gly Thr Gly Arg Tyr Phe Lys Asn Val Lys Asp Phe
                85                  90                  95

Pro Ala Arg Asp Thr Gly Leu Val Gln Ile Ala Lys Asp Gly His Ser
            100                 105                 110

Val Asp Leu Leu Trp Gly Phe Asn Asp Gly Gly Gln Pro Thr Ser Glu
        115                 120                 125

Phe Pro Ser His Leu Met Thr His Ile Gln Arg Leu Lys Gln Asp Pro
130                 135                 140

Asn Gln Arg Val Val Met His Cys His Pro Thr Asn Leu Val Ala Met
145                 150                 155                 160

Ser Phe Thr Leu Pro Leu Glu Glu Lys Leu Phe Ser Arg Ile Leu Trp
                165                 170                 175

Lys Met Gln Ala Glu Ser Ile Val Val Phe Pro Glu Gly Ile Gly Val
            180                 185                 190

Leu Pro Tyr Met Thr Pro Gly Thr Asn Glu Ile Gly Gln Ala Thr Ala
        195                 200                 205

Gln Lys Met Ala Asp Phe Arg Ile Val Met Trp Pro Gln His Gly Ile
210                 215                 220

Phe Gly Ala Gly Asp Ser Ile Asp Glu Thr Tyr Gly Leu Ile Glu Thr
225                 230                 235                 240

Val Glu Lys Ala Ala Thr Ile Tyr Thr Ala Ile Gln Ala Gln Gly Gly
                245                 250                 255

Arg Ile Ile Asn Glu Ile Thr Asp Glu Asn Leu Glu Gln Leu Ala Lys
            260                 265                 270

Arg Phe Asp Leu Thr Pro Asn Leu Ala Phe Leu His Gly Asp Ser Leu
        275                 280                 285

Ile Ser Gln Val Thr Leu Lys Val
290                 295
```

```
<210> SEQ ID NO 5
<211> LENGTH: 275
<212> TYPE: PRT
<213> ORGANISM: Serratia odorifera

<400> SEQUENCE: 5
```

| | | | | | | | | | | | | | | |
|---|---|---|---|---|---|---|---|---|---|---|---|---|---|---|
| Met | Gln | Arg | Ile | Leu | Ser | Ser | Trp | Phe | Val | Gln | Gly | Met | Ile | Lys | Ala |
| 1 | | | | 5 | | | | | 10 | | | | | 15 | |

| Thr | Gly | Asp | Met | Trp | Leu | Lys | Gly | Trp | Asp | Glu | Arg | Asn | Gly | Gly | Asn |
|---|---|---|---|---|---|---|---|---|---|---|---|---|---|---|---|
| | | | 20 | | | | | 25 | | | | | 30 | | |

| Ile | Ser | Leu | Arg | Leu | Thr | Asp | Asp | Val | Ala | Pro | Tyr | Arg | Ala | Asp |
|---|---|---|---|---|---|---|---|---|---|---|---|---|---|---|
| | | 35 | | | | | 40 | | | | | 45 | | |

| Phe | Val | Ala | Glu | Pro | Arg | Cys | Glu | Glu | Leu | Ser | Gln | Pro | Ala | Ala | Glu |
|---|---|---|---|---|---|---|---|---|---|---|---|---|---|---|---|
| | 50 | | | | | 55 | | | | | 60 | | | | |

| Leu | Ala | Asp | Cys | Trp | Phe | Leu | Val | Thr | Gly | Ser | Gly | Lys | Phe | Phe | Arg |
|---|---|---|---|---|---|---|---|---|---|---|---|---|---|---|---|
| 65 | | | | | 70 | | | | | 75 | | | | | 80 |

| Asn | Val | Pro | Leu | Ala | Pro | Glu | Glu | Ser | Leu | Val | Leu | Leu | Gln | Val | Asn |
|---|---|---|---|---|---|---|---|---|---|---|---|---|---|---|---|
| | | | | 85 | | | | | 90 | | | | | 95 | |

| His | Asn | Gly | Thr | Ala | Tyr | His | Ile | His | Trp | Gly | Leu | Ser | Gln | Gly | Gly |
|---|---|---|---|---|---|---|---|---|---|---|---|---|---|---|---|
| | | | 100 | | | | | 105 | | | | | 110 | | |

| Leu | Pro | Thr | Ser | Glu | Leu | Ala | Ser | His | Phe | Gln | Ser | His | Ile | Val | Arg |
|---|---|---|---|---|---|---|---|---|---|---|---|---|---|---|---|
| | | | 115 | | | | | 120 | | | | | 125 | | |

| Met | Gln | Leu | Ser | Asn | Gly | Gln | Asp | Arg | Val | Ile | Met | His | Cys | His | Ala |
|---|---|---|---|---|---|---|---|---|---|---|---|---|---|---|---|
| | 130 | | | | | 135 | | | | | 140 | | | | |

| Thr | Asn | Leu | Ile | Ala | Leu | Ser | Phe | Val | Glu | Lys | Leu | Glu | Ser | Ala | Ser |
|---|---|---|---|---|---|---|---|---|---|---|---|---|---|---|---|
| 145 | | | | | 150 | | | | | 155 | | | | | 160 |

| Phe | Thr | Arg | Leu | Leu | Trp | Glu | Gly | Ser | Thr | Glu | Cys | Leu | Val | Val | Phe |
|---|---|---|---|---|---|---|---|---|---|---|---|---|---|---|---|
| | | | | 165 | | | | | 170 | | | | | 175 | |

| Pro | Asp | Gly | Ile | Gly | Ile | Val | Pro | Trp | Met | Val | Pro | Gly | Thr | Asp | Gly |
|---|---|---|---|---|---|---|---|---|---|---|---|---|---|---|---|
| | | | 180 | | | | | 185 | | | | | 190 | | |

| Ile | Gly | Val | Lys | Thr | Ala | Glu | Gln | Met | Arg | His | His | Ser | Leu | Val | Leu |
|---|---|---|---|---|---|---|---|---|---|---|---|---|---|---|---|
| | | 195 | | | | | 200 | | | | | 205 | | | |

| Trp | Pro | Phe | His | Gly | Ile | Phe | Gly | Cys | Gly | Pro | Thr | Leu | Asp | Glu | Ala |
|---|---|---|---|---|---|---|---|---|---|---|---|---|---|---|---|
| | 210 | | | | | 215 | | | | | 220 | | | | |

| Phe | Gly | Leu | Ile | Asp | Thr | Ala | Glu | Lys | Ser | Ala | Glu | Ile | Met | Val | Lys |
|---|---|---|---|---|---|---|---|---|---|---|---|---|---|---|---|
| 225 | | | | | 230 | | | | | 235 | | | | | 240 |

| Val | Ile | Ala | Met | Gly | Gly | Lys | Arg | Gln | Thr | Ile | Ser | Thr | Glu | Gln | Phe |
|---|---|---|---|---|---|---|---|---|---|---|---|---|---|---|---|
| | | | | 245 | | | | | 250 | | | | | 255 | |

| Ile | Ala | Leu | Ala | Ala | Arg | Phe | Gly | Val | Thr | Pro | Met | Ser | Ala | Ala | Leu |
|---|---|---|---|---|---|---|---|---|---|---|---|---|---|---|---|
| | | | 260 | | | | | 265 | | | | | 270 | | |

| Glu | Val | Gln |
|---|---|---|
| | | 275 |

```
<210> SEQ ID NO 6
<211> LENGTH: 274
<212> TYPE: PRT
<213> ORGANISM: Cronobacter turicensis

<400> SEQUENCE: 6
```

| | | | | | | | | | | | | | | |
|---|---|---|---|---|---|---|---|---|---|---|---|---|---|---|
| Met | Gln | Arg | Ile | Leu | Ser | Ser | Trp | Phe | Val | Gln | Gly | Met | Val | Lys | Ala |
| 1 | | | | 5 | | | | | 10 | | | | | 15 | |

| Thr | Ser | Asp | Met | Trp | Leu | Lys | Gly | Trp | Asp | Glu | Arg | Asn | Gly | Gly | Asn |
|---|---|---|---|---|---|---|---|---|---|---|---|---|---|---|---|
| | | | 20 | | | | | 25 | | | | | 30 | | |

| Val | Ser | Leu | Arg | Leu | Asp | Ala | Ala | Asp | Val | Glu | Pro | Tyr | Arg | Asp | Glu |
|---|---|---|---|---|---|---|---|---|---|---|---|---|---|---|---|
| | | 35 | | | | | 40 | | | | | 45 | | | |

| Phe | Tyr | Pro | Ala | Pro | Arg | Ser | Val | Glu | Leu | Ser | Gln | Pro | Arg | Thr | Glu |
|---|---|---|---|---|---|---|---|---|---|---|---|---|---|---|---|

```
                    50                  55                  60
Leu Ala Gly Cys Trp Phe Leu Val Thr Gly Ser Gly Lys Phe Phe Arg
 65                  70                  75                  80

Asn Val Gln Leu Asp Pro Ala Asp Thr Leu Val Leu Leu Gln Ile Thr
                 85                  90                  95

Asp Asp Gly Met Ala Tyr His Ile His Trp Gly Leu Ala Asn Gly Gly
                100                 105                 110

Leu Pro Thr Ser Glu Leu Ala Ser His Phe Gln Ser His Ala Val Arg
                115                 120                 125

Lys Ala Val Ser Ala Asp Lys Asp Arg Val Ile Met His Cys His Ala
                130                 135                 140

Thr Asn Leu Ile Ala Leu Ser Phe Val Leu Glu Leu Asp Glu Ala Arg
145                 150                 155                 160

Phe Thr Arg Leu Leu Trp Glu Gly Ser Thr Glu Cys Leu Val Val Phe
                165                 170                 175

Pro Asp Gly Ile Gly Ile Val Pro Trp Met Val Pro Gly Thr Asp Gly
                180                 185                 190

Ile Gly Ser Ala Thr Ser Glu Gln Met Lys Thr His Thr Leu Val Leu
                195                 200                 205

Trp Pro His His Gly Ile Phe Gly Thr Gly Pro Thr Leu Asp Glu Ala
210                 215                 220

Phe Gly Leu Ile Asp Thr Ala Glu Lys Ser Ala Glu Ile Leu Val Lys
225                 230                 235                 240

Val Leu Ser Met Gly Gly Met Lys Gln Thr Ile Thr Arg Glu Glu Leu
                245                 250                 255

Ile Ala Leu Gly Glu Arg Phe Gly Val Thr Pro His Ala Gly Ala Ile
                260                 265                 270

Ala Leu
```

<210> SEQ ID NO 7
<211> LENGTH: 273
<212> TYPE: PRT
<213> ORGANISM: Providencia rettgeri

<400> SEQUENCE: 7

```
Met Gln Asp Ile Leu Thr Ser Trp Phe Val Gln Gly Met Ile Lys Ala
 1                   5                  10                  15

Thr Ser Asp Met Trp Leu Lys Gly Trp Asp Glu Arg Asn Gly Gly Asn
                 20                  25                  30

Val Ser Leu Arg Leu Thr Glu Asp Val Ala Pro Phe Lys His Thr
                 35                  40                  45

Phe His Ala Asp Pro Arg Tyr Ile Glu Thr Thr Glu Pro Val Lys Glu
                 50                  55                  60

Leu Ala Asn Gln Tyr Phe Ile Val Thr Gly Ser Gly Lys Phe Phe Arg
 65                  70                  75                  80

Asn Val Ala Leu Asp Pro Ala Asp Asn Leu Gly Leu Val Arg Ile Asp
                 85                  90                  95

Asn Glu Gly Gln Gly Tyr His Ile Val Trp Gly Phe Val Asn Gly Ala
                100                 105                 110

Ile Pro Thr Ser Glu Phe Ala Ala His Phe Gln Ser His Ile Thr Arg
                115                 120                 125

Met Gln Ala Thr Asn Gly Ala Asn Arg Val Ile Met His Cys His Ala
                130                 135                 140

Thr Asn Ile Ile Ala Leu Ser Tyr Val Leu Pro Leu Asp Ser Ala Ser
```

```
145                 150                 155                 160
Ile Thr Arg His Leu Trp Glu Met Ser Thr Glu Cys Leu Val Val Phe
                165                 170                 175
Pro Asp Gly Ile Gly Val Leu Pro Trp Met Val Pro Gly Thr Asp Gly
            180                 185                 190
Ile Gly Leu Glu Thr Ala Glu Met Lys Gln His Gly Leu Val Leu
        195                 200                 205
Trp Pro Phe His Gly Ile Phe Gly Ser Gly Pro Thr Leu Asp Asp Ala
210                 215                 220
Phe Gly Leu Ile Asp Thr Ala Glu Lys Ser Ala Glu Ile Leu Val Lys
225                 230                 235                 240
Val Leu Ser Met Gly Gly Lys Lys Gln Thr Ile Ser Thr Glu Asn Leu
                245                 250                 255
Ile Ala Leu Ala Lys Arg Phe Asn Val Thr Pro Met Ser Asp Ala Leu
            260                 265                 270
Lys

<210> SEQ ID NO 8
<211> LENGTH: 275
<212> TYPE: PRT
<213> ORGANISM: Marvinbryantia formatexigens

<400> SEQUENCE: 8

Met Lys Val Leu Glu Ala Glu Phe Val Arg Glu Phe Ile Arg Met Cys
1               5                   10                  15
Asp Asp Gly Trp Lys Gln Gly Trp His Glu Arg Asn Gly Gly Asn Leu
            20                  25                  30
Ser Tyr Arg Ile Arg Lys Glu Glu Ile Asp Ala Met Lys Glu Asp Phe
        35                  40                  45
Asn Pro Ala Gly Ala Trp Leu Glu Ile Gly Thr Ser Val Pro Gly Leu
50                  55                  60
Arg Gly Glu Tyr Phe Leu Val Thr Gly Ser Gly Lys His Phe Arg Asn
65                  70                  75                  80
Val Ala Gly Lys Pro Glu Glu Ser Ile Gly Ile Ile Glu Ile Asp Asp
                85                  90                  95
Ser Gly Glu His Tyr Arg Ile Cys Trp Gly Leu Gln Asp Gln Ala Arg
            100                 105                 110
Pro Thr Ser Glu Leu Pro Thr His Leu Met Asn His Glu Val Lys Lys
        115                 120                 125
Thr Ala Thr Gly Gly Ala His Arg Val Ile Tyr His Ala His Pro Ala
    130                 135                 140
Asn Leu Ile Ala Leu Thr Phe Leu Leu Pro Leu Lys Asp Glu Val Phe
145                 150                 155                 160
Thr Arg Glu Leu Trp Glu Met Ala Thr Glu Cys Pro Val Val Phe Pro
                165                 170                 175
Ala Gly Ile Gly Val Val Gly Trp Met Val Pro Gly Gly Arg Glu Ile
            180                 185                 190
Ala Val Ala Thr Ser Lys Leu Met Glu Gln Tyr Asp Ala Val Val Trp
        195                 200                 205
Ala His His Gly Leu Phe Ala Ser Gly Glu Asp Phe Asp Asn Thr Phe
    210                 215                 220
Gly Leu Met His Thr Ile Glu Lys Ser Ala Glu Ile Leu Val Lys Val
225                 230                 235                 240
Leu Ser Val Arg Pro Asp Lys Leu Gln Thr Ile Gln Pro Gln Asp Phe
```

Arg Asn Leu Ala Ala Glu Phe Lys Val Thr Leu Pro Glu Lys Phe Leu
            245                 250                 255
Tyr Glu Lys
        260             265                 270

275

<210> SEQ ID NO 9
<211> LENGTH: 272
<212> TYPE: PRT
<213> ORGANISM: Mitsuokella multacida

<400> SEQUENCE: 9

Met Asp Ile Gln Asp Ser Lys Phe Met Glu Gly Phe Lys Arg Leu Thr
1               5                   10                  15

Ala Asp Ala Phe Lys Lys Gly Trp His Glu Arg Asn Gly Gly Asn Leu
            20                  25                  30

Thr Tyr Arg Val Lys Pro Glu Glu Val Glu Ala Val Lys Glu Ser Leu
        35                  40                  45

His Glu Val Lys Glu Trp Gln Pro Ile Gly Asn Thr Val Pro Gly Leu
    50                  55                  60

Ala Gly Glu Tyr Phe Leu Val Thr Gly Ser Gly Lys Tyr Met Arg Asn
65                  70                  75                  80

Val Ser Leu Ala Pro Glu Glu Asn Val Ala Leu Ile Lys Ile Asp Glu
                85                  90                  95

Lys Gly Glu Gln Tyr Gly Ile Val Trp Gly Leu Val Asn Gly Gly Arg
            100                 105                 110

Pro Thr Ser Glu Leu Pro Thr His Leu Ala Ala His Glu Leu Lys Lys
        115                 120                 125

Lys Met Thr Asp Gly Arg Asn Arg Ile Ile Tyr His Ala His Pro Thr
    130                 135                 140

Asn Leu Ile Ala Leu Thr Phe Val Leu Pro Leu Lys Asp Lys Glu Phe
145                 150                 155                 160

Thr Arg Glu Leu Trp Glu Met Ala Thr Glu Asp Pro Val Ile Phe Pro
                165                 170                 175

Glu Gly Ile Gly Val Val Pro Trp Met Val Pro Gly Gly Lys Glu Ile
            180                 185                 190

Ala Asp Ala Ser Val Lys Leu Met Glu Lys Tyr Arg Val Val Val Trp
        195                 200                 205

Ala His His Gly Leu Phe Val Cys Gly Asp Asp Phe Asp Glu Ala Phe
    210                 215                 220

Gly Leu Met Asp Thr Val Glu Lys Ala Ser Glu Ile Cys Val Lys Val
225                 230                 235                 240

Leu Ser Met Gly Gly Lys Lys Gln Thr Ile Pro Arg Glu Gly Phe Ile
                245                 250                 255

Gln Leu Ala Lys Asp Phe His Ile Asp Leu Asn Thr Asp Leu Leu Asp
            260                 265                 270

<210> SEQ ID NO 10
<211> LENGTH: 269
<212> TYPE: PRT
<213> ORGANISM: Bacteroides thetaiotaomicron

<400> SEQUENCE: 10

Met Lys Ser Ile Leu Glu Asn Arg Pro Ala Leu Ala Lys Glu Val Asn
1               5                   10                  15

Lys Val Ala Glu Val Ala Gly Tyr Leu Trp Gln Lys Gly Trp Ala Glu

```
            20                  25                  30
Arg Asn Gly Gly Asn Ile Thr Val Asn Ile Thr Glu Phe Val Asp Asp
            35                  40                  45

Glu Ile Arg Arg Met Glu Pro Ile Ser Glu Val Lys Ser Ile Gly Val
        50                  55                  60

Thr Leu Pro Tyr Leu Lys Gly Cys Tyr Phe Tyr Cys Lys Gly Thr Asn
65                  70                  75                  80

Lys Arg Met Arg Asp Leu Ala Arg Trp Pro Met Glu Asn Gly Ser Val
                85                  90                  95

Ile Arg Ile Leu Asp Asp Cys Ala Ser Tyr Val Ile Ala Asp Glu
            100                 105                 110

Ala Val Ala Pro Thr Ser Glu Leu Pro Ser His Leu Ser Val His Asn
        115                 120                 125

Asp Leu Leu Ser Lys Asn Ser Pro Tyr Lys Ala Ser Val His Thr His
    130                 135                 140

Pro Ile Glu Leu Ile Ala Met Thr His Cys Glu Lys Phe Leu Gln Lys
145                 150                 155                 160

Asp Val Ala Thr Asn Leu Leu Trp Ser Met Ile Pro Glu Thr Lys Ala
                165                 170                 175

Phe Cys Pro Arg Gly Leu Gly Ile Ile Pro Tyr Lys Leu Pro Ser Ser
            180                 185                 190

Val Glu Leu Ala Glu Ala Thr Ile Lys Glu Leu Gln Asp Tyr Asp Val
        195                 200                 205

Val Met Trp Glu Lys His Gly Val Phe Ala Val Asp Cys Asp Ala Met
    210                 215                 220

Gln Ala Phe Asp Gln Ile Asp Val Leu Asn Lys Ser Ala Leu Ile Tyr
225                 230                 235                 240

Ile Ala Ala Lys Asn Met Gly Phe Glu Pro Asp Gly Met Ser Gln Glu
                245                 250                 255

Gln Met Lys Glu Met Ser Val Ala Phe Asn Leu Pro Lys
            260                 265

<210> SEQ ID NO 11
<211> LENGTH: 274
<212> TYPE: PRT
<213> ORGANISM: Shimwellia blattae

<400> SEQUENCE: 11

Met Gln Gln Ile Leu Asp Ala Trp Phe Val Gln Gly Met Ile Lys Ala
1               5                   10                  15

Thr Ser Asp Ala Trp Leu Lys Gly Trp Asp Glu Arg Asn Gly Gly Asn
            20                  25                  30

Leu Thr Leu Arg Leu Asp Glu Asp Ile Ala Pro Tyr Thr Ala Asp
        35                  40                  45

Phe His Ala Thr Pro Arg Tyr Ile Pro Leu Ser Gln Pro Met Pro Glu
    50                  55                  60

Leu Ala Gly Thr Pro Phe Ile Val Thr Gly Ser Gly Lys Phe Phe Arg
65                  70                  75                  80

Asn Val Ala Leu Glu Thr Ala Ala Asn Ile Gly Val Val Arg Val Asp
                85                  90                  95

Arg Asp Gly Ala Gly Tyr His Ile Leu Trp Gly Leu Glu Gly Asp Ala
            100                 105                 110

Leu Pro Thr Ser Glu Leu Pro Ala His Phe Leu Ser His Cys Ala Arg
        115                 120                 125
```

Ile Arg Ala Thr Gly Gly Lys Asp Arg Val Ile Met His Cys His Ala
130                 135                 140

Thr Asn Leu Ile Ala Leu Thr Tyr Val Leu Glu Asn Asp Thr Asn Leu
145                 150                 155                 160

Ile Thr Arg Lys Leu Trp Glu Gly Ser Thr Glu Cys Leu Val Val Phe
                165                 170                 175

Pro Asp Gly Val Gly Ile Leu Pro Trp Met Val Pro Gly Thr Asp Asp
                180                 185                 190

Ile Gly Gln Thr Thr Ala Arg Glu Met Asp Lys His Ala Leu Val Leu
                195                 200                 205

Trp Pro Phe His Gly Val Phe Gly Ser Gly Pro Thr Leu Asp Glu Ala
210                 215                 220

Phe Gly Leu Ile Asp Thr Ala Glu Lys Ser Ala Glu Ile Leu Val Lys
225                 230                 235                 240

Val Leu Ser Met Gly Gly Met Lys Gln Thr Ile Ser Arg Glu Glu Leu
                245                 250                 255

Ala Ala Leu Ala Ala Arg Phe Gly Val Thr Pro Leu Ala Gly Ala Leu
                260                 265                 270

Ala Leu

<210> SEQ ID NO 12
<211> LENGTH: 281
<212> TYPE: PRT
<213> ORGANISM: Enterococcus avium

<400> SEQUENCE: 12

Met Lys Leu His Glu Ile Asn Gln Ala Pro Phe Ile Lys Glu Met Cys
1               5                   10                  15

Glu Ala Thr Ser Gln Leu Trp Ala Tyr Gly Trp Ala Glu Arg Asn Gly
                20                  25                  30

Gly Asn Ile Ser Tyr Arg Leu Pro Gln Glu Glu Val Gln Tyr Tyr Leu
                35                  40                  45

Asp Ser Asp Gln Val Lys Arg Thr Ile Pro Leu Asp Phe Thr Val Lys
50                  55                  60

Ser Leu Ala Gly Glu Leu Phe Leu Val Ser Gly Ser Gly Lys Tyr Phe
65                  70                  75                  80

Lys Asn Ile Gln Lys Asn Pro Ala Asp Ser Leu Ala Ile Ile Arg Ile
                85                  90                  95

Ser Ala Glu Gly Asp Arg Tyr Glu Leu Leu Trp Gly Leu Glu Gly Gly
                100                 105                 110

Asp Leu Pro Thr Ser Glu Leu Ala Ser His Leu Gln Cys His Glu Val
                115                 120                 125

Arg Leu Ala Gln Asp Pro Glu His Arg Val Ile Leu His Thr His Ala
130                 135                 140

Thr Ala Ile Ser Ala Met Thr Phe Ile His Asp Leu Asp Glu Lys Lys
145                 150                 155                 160

Phe Ser Lys Thr Leu Trp Gln Met Ile Thr Glu Cys Leu Val Val Phe
                165                 170                 175

Pro Asp Gly Val Ser Val Leu Pro Trp Met Val Ala Gly Thr Ser Gln
                180                 185                 190

Leu Gly Ala Ala Ser Ala Asp Lys Met Gln Asn Ser Arg Ile Val Ile
                195                 200                 205

Trp Pro His His Gly Ile Met Gly Ala Gly Gln Thr Met Asp Asp Ala
210                 215                 220

```
Phe Gly Leu Val Glu Thr Ala Glu Lys Ala Ala Glu Ile Tyr Leu Gln
225                 230                 235                 240

Ile Cys Ser Ala Lys Gln Glu Ile Lys Gln Gln Ile Thr Asp Gln Gln
            245                 250                 255

Leu Leu Asp Leu Ala Glu Lys Phe His Val Lys Pro Lys Ser Gly Ile
            260                 265                 270

Leu Leu Glu Glu Gly Leu Arg Ser Asp
            275                 280
```

<210> SEQ ID NO 13
<211> LENGTH: 270
<212> TYPE: PRT
<213> ORGANISM: [Clostridium] termitidis

<400> SEQUENCE: 13

Met Lys Asp Ile Leu Thr Ala Pro Phe Ile Thr Glu Ile Cys Lys Leu
1 5 10 15

Thr Ser Asn Leu Tyr Arg Leu Gly Trp Asp Glu Arg Asn Gly Gly Asn
20 25 30

Ile Ser Tyr Ile Val Pro Glu Ala Glu Ala Ala Glu Tyr Leu Asp Ile
35 40 45

Lys Lys Ala Ile Arg Asn Ile Pro Met Thr Phe Asp Gly Thr Ser Leu
50 55 60

Ala Gly Arg Ile Phe Val Val Thr Gly Thr Gly Lys Tyr Phe Lys Asn
65 70 75 80

Val Met Asp Ala Pro Gly Ile Asn Leu Gly Ile Ile Lys Val Lys Glu
85 90 95

Asp Gly Lys Ser Leu Asp Leu Leu Trp Gly Tyr Glu Asp Gly Gly Arg
100 105 110

Pro Thr Ser Glu Leu Pro Ala His Leu Met Thr His Ile Glu Arg Leu
115 120 125

Lys Ala Asp Pro Asn His Arg Val Val Ile His Ser His Pro Thr Asn
130 135 140

Thr Ile Ala Met Thr Phe Val His Glu Leu Asp Glu Arg Ala Phe Thr
145 150 155 160

Arg Thr Leu Trp Gln Met Cys Thr Glu Cys Leu Val Val Phe Pro Asp
165 170 175

Gly Val Gly Val Leu Pro Trp Met Leu Cys Gly Asn Glu Glu Ile Gly
180 185 190

Arg Val Thr Ala Gln Lys Met Lys Glu Phe Arg Val Val Val Trp Gly
195 200 205

Met His Gly Ile Phe Gly Thr Gly Arg Asp Leu Asp Glu Thr Phe Gly
210 215 220

Leu Ile Glu Thr Val Glu Lys Ala Ala Glu Ile Tyr Ile Lys Ile Met
225 230 235 240

Asn Met Pro Ile Arg Gln Thr Ile Thr Asp Asp Asn Leu Lys Val Leu
245 250 255

Ala Gly Ala Phe Gly Val Thr Pro Arg Ala Gly Tyr Leu Glu
260 265 270

<210> SEQ ID NO 14
<211> LENGTH: 304
<212> TYPE: PRT
<213> ORGANISM: Lactobacillus shenzhenensis

<400> SEQUENCE: 14

Met Asp Met Lys Lys Gln Phe Leu Asn Pro Glu Tyr Ala Pro Ala Phe
1               5                   10                  15

Val Asp Ser Pro Tyr Val Thr Gln Met Arg Lys Thr Thr Trp Asn Leu
            20                  25                  30

Tyr Ser His Gly Trp Asp Glu Arg Asn Gly Gly Asn Val Ser Tyr Arg
        35                  40                  45

Leu Thr Ala Asp Glu Ile Lys Met Tyr Gly Asp Val His Ser Val Leu
    50                  55                  60

Arg Asn Ile Pro Ile Lys Phe Asp Ala Ser Leu Lys Gly Asp Tyr
65                  70                  75                  80

Phe Leu Val Thr Gly Thr Gly Arg Tyr Phe Lys Asn Val Thr Asp Phe
                85                  90                  95

Pro Gln Arg Asp Leu Gly Leu Val Arg Ile Ala Asp Gly Lys Ser
            100                 105                 110

Val Asp Leu Val Trp Gly Phe Asn Asp Gly Gly Gln Pro Thr Ser Glu
        115                 120                 125

Phe Pro Ala His Leu Met Thr His Ile Gln Arg Leu Gln His Asp Ala
    130                 135                 140

Asn Gln Arg Ile Val Met His Cys His Pro Thr Asn Leu Val Ala Met
145                 150                 155                 160

Thr Phe Thr Leu Pro Trp Asn Glu Lys Leu Phe Ser Arg Ile Leu Trp
                165                 170                 175

Lys Met Gln Ala Glu Ser Ile Val Val Phe Pro Glu Gly Val Gly Val
            180                 185                 190

Leu Pro Tyr Met Thr Pro Gly Thr Asn Glu Ile Gly Ala Ala Thr Ala
        195                 200                 205

Lys Lys Met Gly Ala Tyr Arg Val Val Leu Trp Pro Leu His Gly Val
    210                 215                 220

Phe Gly Ala Gly Asp Ser Ile Asp Glu Val Tyr Gly Leu Ile Glu Thr
225                 230                 235                 240

Val Glu Lys Ala Ala Thr Ile Tyr Thr Ala Ile Lys Ser Gln Gly Gly
                245                 250                 255

Gln Phe Val Asn Glu Ile Thr Asp Asp Asp Leu His Lys Leu Ala Ala
            260                 265                 270

Arg Phe Asp Leu Thr Pro Asn Lys Asp Phe Ile Asn Gly Lys Ser Leu
        275                 280                 285

Ala Glu Val Leu Asn Gly Ala Ala Ser Lys Glu Pro Val Gly Ala Arg
    290                 295                 300

<210> SEQ ID NO 15
<211> LENGTH: 274
<212> TYPE: PRT
<213> ORGANISM: Dickeya dadantii

<400> SEQUENCE: 15

Met Gln Ser Ile Leu Ser Ser Trp Phe Val Gln Gly Met Val Lys Ala
1               5                   10                  15

Thr Gly Asp Met Trp Leu Lys Gly Trp Asp Glu Arg Asn Gly Gly Asn
            20                  25                  30

Ile Ser Leu Arg Leu Thr Thr Glu Asp Ile Thr Pro Tyr Glu Ser Asp
        35                  40                  45

Phe Tyr Pro Gln Pro Arg His Glu Ala Leu Ser Gln Pro Met Pro Glu
    50                  55                  60

Leu Ala Asn Gly Trp Phe Ile Val Thr Gly Ser Gly Lys Phe Phe Arg
65                  70                  75                  80

```
Asn Val Pro Leu Asp Pro Ala Glu Asn Leu Val Leu Gln Val Asp
                85                  90                  95

Ala Asn Gly Ala Gly Tyr Arg Ile Phe Trp Gly Leu Thr Ala Gly Gly
            100                 105                 110

Leu Pro Thr Ser Glu Leu Ala Ala His Phe Gln Ser His Ile Val Arg
            115                 120                 125

Ile Gly Val Ser Gly Gly Arg Asp Arg Val Ile Met His Cys His Ala
130                 135                 140

Thr Asn Leu Ile Ala Leu Ser Tyr Val Leu Glu Leu Thr Ser Ala Thr
145                 150                 155                 160

Phe Thr Arg Glu Leu Trp Glu Gly Ser Thr Glu Cys Leu Val Val Phe
                165                 170                 175

Pro Asp Gly Val Gly Ile Val Pro Trp Met Val Pro Gly Thr Asp Ala
            180                 185                 190

Ile Gly Thr Ala Thr Ala Glu Gln Met His His Ser Leu Val Leu
            195                 200                 205

Trp Pro Phe His Gly Ile Phe Gly Thr Gly Pro Ser Leu Asp Asp Ala
210                 215                 220

Phe Gly Leu Ile Asp Thr Ala Glu Lys Ser Ala Glu Ile Met Val Lys
225                 230                 235                 240

Val Arg Ala Met Gly Gly Lys Lys Gln Thr Ile Ser Thr Glu Glu Leu
                245                 250                 255

Ile Ala Leu Gly Thr Arg Phe Gly Val Ser Pro Met Ala Ser Ala Leu
            260                 265                 270

Lys Gln

<210> SEQ ID NO 16
<211> LENGTH: 274
<212> TYPE: PRT
<213> ORGANISM: Pectobacterium carotovorum

<400> SEQUENCE: 16

Met Gln Ala Ile Leu Ser Ser Trp Phe Val Gln Gly Met Ile Lys Ala
1               5                   10                  15

Thr Ser Asp Met Trp Leu Lys Gly Trp Asp Glu Arg Asn Gly Gly Asn
            20                  25                  30

Val Ser Leu Arg Leu Thr Ala Glu Asp Val Thr Pro Tyr Glu Ser Asp
        35                  40                  45

Phe Tyr Pro Gln Pro Arg His Glu Ala Leu Ser Gln Pro Met Pro Ala
    50                  55                  60

Leu Ala Asp Cys Trp Phe Ile Val Thr Gly Ser Gly Lys Phe Phe Arg
65                  70                  75                  80

Asn Val Gln Leu Asp Pro Ala Asp Ser Leu Val Val Leu Gln Val Asp
                85                  90                  95

Ser Asp Gly Lys Gly Tyr Arg Ile Phe Trp Gly Leu Thr Asn Gly Gly
            100                 105                 110

Leu Pro Thr Ser Glu Leu Ala Ser His Phe Gln Ser His Ile Val Arg
            115                 120                 125

Met Gly Val Thr His Gly Arg Asp Arg Val Ile Met His Cys His Ala
130                 135                 140

Thr Asn Leu Ile Ala Leu Ser Tyr Val Leu Glu Leu Asp Thr Ala Thr
145                 150                 155                 160

Phe Thr Arg Glu Leu Trp Glu Gly Ser Thr Glu Cys Leu Val Val Phe
                165                 170                 175
```

```
Pro Asp Gly Val Gly Ile Val Pro Trp Met Val Pro Gly Thr Asp Ala
            180                 185                 190

Ile Gly Asp Ala Thr Ser Glu Gln Met Lys Arg His Ser Leu Val Leu
            195                 200                 205

Trp Pro Phe His Gly Ile Phe Gly Thr Gly Pro Thr Leu Asp Glu Ala
            210                 215                 220

Phe Gly Leu Ile Asp Thr Ala Glu Lys Ser Ala Glu Val Met Val Lys
225                 230                 235                 240

Val Arg Ser Met Gly Gly Lys Lys Gln Thr Ile Ser Thr Glu Glu Leu
            245                 250                 255

Ile Ala Leu Gly Lys Arg Phe Gly Val Thr Pro Leu Glu Ala Ala Leu
            260                 265                 270

Arg Val

<210> SEQ ID NO 17
<211> LENGTH: 274
<212> TYPE: PRT
<213> ORGANISM: Obesumbacterium proteus

<400> SEQUENCE: 17

Met Gln Ser Ile Ile Asp Ser Trp Phe Val Gln Gly Met Ile Lys Ala
1               5                   10                  15

Thr Ser Asp Met Trp Leu Lys Gly Trp Asp Glu Arg Asn Gly Gly Asn
            20                  25                  30

Val Ser Leu Arg Leu Leu Glu Glu Val Ala Pro Phe Arg Ala Asp
            35                  40                  45

Phe Asn Ser Gln Pro Arg Cys Val Glu Leu Thr Gln Pro Ala Thr Glu
50                  55                  60

Leu Ala Asn Ser Trp Phe Leu Val Thr Gly Ser Gly Lys Phe Phe Arg
65                  70                  75                  80

Asn Val Gln Ile Ala Pro Gln Glu Asn Leu Val Leu Leu Gln Val Ser
            85                  90                  95

Ala Asp Gly Met Ala Tyr His Ile His Trp Gly Leu Thr Lys Gly Gly
            100                 105                 110

Leu Pro Thr Ser Glu Leu Ala Ala His Phe Gln Ser His Ile Val Arg
            115                 120                 125

Met Gln Val Thr Asn Gly Asp Asn Arg Val Ile Met His Cys His Ala
            130                 135                 140

Thr Asn Leu Ile Ala Leu Ser Tyr Val His Asp Leu Asp Asn Ala Lys
145                 150                 155                 160

Phe Thr Arg Leu Leu Trp Glu Gly Ser Thr Glu Cys Leu Val Val Phe
            165                 170                 175

Pro Asp Gly Ile Gly Ile Val Pro Trp Met Val Pro Gly Thr Asp Gly
            180                 185                 190

Ile Gly Thr Gln Thr Ala Glu Gln Met Arg Gln His Gly Leu Val Leu
            195                 200                 205

Trp Pro Phe His Gly Ile Phe Gly Ser Gly Pro Thr Leu Asp Asp Ala
            210                 215                 220

Phe Gly Leu Ile Asp Thr Ala Glu Lys Ser Ala Glu Ile Met Val Lys
225                 230                 235                 240

Val Leu Ser Met Gly Gly Lys Lys Gln Thr Ile Ser Thr Gln Glu Leu
            245                 250                 255

Ile Ala Leu Ala Ala Arg Phe Gly Val Thr Pro Met Ala Ala Ala Leu
            260                 265                 270
```

Glu Asp

<210> SEQ ID NO 18
<211> LENGTH: 275
<212> TYPE: PRT
<213> ORGANISM: Hungatella hathewayi

<400> SEQUENCE: 18

Met Arg Val Thr Asp Ala Glu Phe Val Lys Gly Phe Ile Arg Leu Cys
1               5                   10                  15

Asp Asp Gly Phe Lys Gln Asn Trp His Glu Arg Asn Gly Gly Asn Leu
            20                  25                  30

Ser Tyr Arg Ile Lys Pro Glu Glu Val Glu Ser Val Lys Glu Glu Leu
        35                  40                  45

Thr Asp Ser Asn Pro Trp Gln Pro Ile Gly Thr Ser Val Pro Lys Leu
    50                  55                  60

Ala Gly Glu Tyr Phe Met Val Thr Gly Ser Gly Lys Tyr Phe Arg Asn
65                  70                  75                  80

Val Ile Leu Asp Pro Ala Ala Asn Ser Cys Ile Ile Glu Val Asp Glu
                85                  90                  95

Ala Gly Glu Asn Tyr Arg Ile Cys Trp Gly Leu Val Asn Gly Gly Arg
            100                 105                 110

Pro Thr Ser Glu Leu Pro Ser His Leu Met Asn His Glu Val Lys Lys
        115                 120                 125

Glu Val Thr Gly Gly Lys His Arg Val Ile Tyr His Ala His Pro Thr
    130                 135                 140

Asn Val Ile Ala Leu Thr Phe Val Leu Pro Leu Glu Asp Lys Val Phe
145                 150                 155                 160

Thr Arg Glu Leu Trp Glu Met Ala Thr Glu Cys Pro Val Val Phe Pro
                165                 170                 175

Asp Gly Val Gly Val Val Gly Trp Met Val Pro Gly Gly Arg Asp Ile
            180                 185                 190

Ala Val Ala Thr Ser Glu Leu Met Lys Lys Tyr Asp Val Ala Val Trp
        195                 200                 205

Ala His His Gly Leu Phe Ala Ser Gly Glu Asp Phe Asp Leu Thr Phe
    210                 215                 220

Gly Leu Met His Thr Val Glu Lys Ser Ala Glu Ile Leu Val Lys Val
225                 230                 235                 240

Leu Ser Ile Arg Pro Asp Lys Leu Gln Thr Ile Thr Pro Gln Asn Phe
                245                 250                 255

Lys Asp Leu Ala Lys Asp Phe Lys Val Thr Leu Pro Glu Glu Phe Leu
            260                 265                 270

Tyr Glu Lys
        275

<210> SEQ ID NO 19
<211> LENGTH: 272
<212> TYPE: PRT
<213> ORGANISM: Megamonas hypermegale

<400> SEQUENCE: 19

Met Leu Ile Thr Asn Ala Glu Phe Ile Gln Gly Phe Ile Arg Leu Thr
1               5                   10                  15

Asp Asp Ala Phe Lys Lys Gly Trp His Glu Arg Asn Gly Gly Asn Leu
            20                  25                  30

```
Ser Tyr Arg Ile Lys Pro Glu Glu Ile Glu Ile Lys Ser Glu Leu
         35                  40                  45

Lys Ala Pro Thr Asn Trp Ile Pro Ile Gly Val Ser Val Pro Asn Leu
 50                  55                  60

Ala Asn Glu Tyr Phe Leu Val Ser Gly Thr Gly Arg Tyr Met Arg Asn
 65                  70                  75                  80

Ile Ile Leu Lys Pro Lys Asp Asn Ile Cys Ile Ala Lys Ile Asp Asp
                 85                  90                  95

Lys Gly Glu Asn Tyr Ala Ile Val Trp Gly Leu Glu Lys Gly Gly Arg
            100                 105                 110

Pro Thr Ser Glu Phe Pro Thr His Leu Met Asn His Ser Ile Lys Lys
        115                 120                 125

Asp Leu Thr Asn Gly Gln Asn His Val Ile Tyr His Ala His Pro Thr
130                 135                 140

Asn Ile Ile Ala Leu Thr Phe Val Leu Pro Leu Asn Asp Lys Glu Phe
145                 150                 155                 160

Thr Arg Glu Leu Trp Glu Met Ala Thr Glu Asp Pro Val Ile Phe Pro
                165                 170                 175

Glu Gly Ile Gly Val Val Pro Trp Met Val Pro Gly Gly Ser Glu Ile
            180                 185                 190

Ala Lys Ala Thr Ser Glu Leu Met Lys Lys Tyr Asn Ile Val Val Trp
        195                 200                 205

Ala His His Gly Met Phe Cys Ser Gly Lys Asp Phe Asp Glu Ala Phe
    210                 215                 220

Gly Leu Met Asp Thr Ala Glu Lys Ala Glu Ile Cys Val Lys Val
225                 230                 235                 240

Arg Ser Met Gly Gly Lys Lys Gln Thr Ile Thr Thr Gln Asn Phe Leu
                245                 250                 255

Asp Leu Ala Lys Asp Phe Lys Ile Asp Leu Asn Lys Thr Phe Leu Lys
            260                 265                 270

<210> SEQ ID NO 20
<211> LENGTH: 269
<212> TYPE: PRT
<213> ORGANISM: Prevotella oryzae

<400> SEQUENCE: 20

Met Lys Ser Ile Leu Glu Gly Arg Pro Ala Leu Lys Lys Glu Val Asp
 1               5                  10                  15

Lys Ile Ala Glu Val Ala Gly Tyr Leu Trp Gln Lys Gly Trp Ala Glu
                 20                  25                  30

Arg Asn Gly Gly Asn Ile Thr Val Asn Ile Thr Asp Leu Val Asp Asp
            35                  40                  45

Glu Ile Lys Asn Met Pro Ala Ile Ser Glu Val Lys Gln Ile Gly Val
        50                  55                  60

Thr Leu Pro His Leu Lys Gly Thr Tyr Phe Phe Cys Lys Gly Thr Gly
 65                  70                  75                  80

Met Arg Met Arg Asp Leu Ala Arg Trp Pro Met Asp Asn Gly Ser Ile
                 85                  90                  95

Ile Arg Ile Leu Asp Asp Cys Ala Ser Tyr Val Ile Ile Ala Asp Asn
            100                 105                 110

Pro Val Asn Pro Thr Ser Glu Leu Pro Ser His Leu Met Val His Asn
        115                 120                 125

His Leu Ile Glu Lys Gly Ser Thr Phe Lys Ala Ser Leu His Thr His
130                 135                 140
```

Pro Ile Glu Leu Ile Ala Met Thr His Ile Arg Lys Phe Met Gly Lys
145                 150                 155                 160

Asp Val Leu Thr Lys Leu Leu Trp Ser Met Ile Pro Glu Thr Lys Ala
            165                 170                 175

Phe Cys Pro Lys Gly Leu Gly Ile Ile Pro Tyr Glu Leu Pro Ser Ser
        180                 185                 190

Val Lys Leu Ala Glu Glu Thr Val Arg Gln Leu Asp Asp Tyr Asp Val
    195                 200                 205

Ala Met Trp Glu Lys His Gly Val Phe Ala Ile Asp Asn Asp Ile Met
210                 215                 220

Ala Ala Phe Asp Gln Val Asp Val Leu Asn Lys Ser Ala Leu Ile Tyr
225                 230                 235                 240

Ile Ala Ala Lys Asn Met Gly Ala Asp Pro Glu Gly Met Ser Asp Ala
                245                 250                 255

Gln Met Val Glu Met Thr Lys Ala Phe Asn Leu Pro Lys
            260                 265

<210> SEQ ID NO 21
<211> LENGTH: 236
<212> TYPE: PRT
<213> ORGANISM: Thermotoga maritima

<400> SEQUENCE: 21

Met Arg Glu Thr Ile Arg Glu Ile Gln Lys Val Ala Tyr Trp Leu Ala
1               5                   10                  15

Ile Lys Gly Leu Ser Glu Ala Asn Ala Gly Asn Ile Ser Val Arg Leu
            20                  25                  30

Asp Glu Arg Pro Glu Gly Tyr Glu Val Lys Ser Val Asn Glu Tyr Gly
        35                  40                  45

Phe Asp Tyr Asp Gly Pro Glu Met Tyr Leu Leu Ile Thr Ala Thr Gly
    50                  55                  60

Ser Arg Met Arg Glu Val Tyr Glu Asp Asp Ser Lys Ile Cys Leu Leu
65                  70                  75                  80

His Val Leu Pro Gly Lys His Tyr Glu Ile Leu His Gly Asn Gly Lys
                85                  90                  95

Pro Thr Ser Glu Phe Pro Thr His Leu Met Ile His Ala Lys Phe Lys
            100                 105                 110

Glu Met Asn Pro Glu Lys Lys Ala Ile Val His Thr His Pro Leu Asn
        115                 120                 125

Leu Leu Thr Leu Met Asn Leu Glu Glu Phe Gln Glu Leu Leu Pro Lys
    130                 135                 140

Met Met Lys Ile His Pro Glu Val Leu Ile Phe Phe Pro Gln Gly Ile
145                 150                 155                 160

Ser Val Val Glu Phe Glu Lys Pro Gly Ser Val Glu Leu Gly Leu Lys
                165                 170                 175

Thr Val Glu Lys Ser Glu Gly Lys Asp Ala Val Leu Trp Asp Lys His
            180                 185                 190

Gly Val Val Ala Phe Gly Lys Asp Val Ala Glu Ala Tyr Asp Arg Val
        195                 200                 205

Glu Ile Leu Glu Lys Ala Ala Glu Ile Leu Leu Arg Val Leu Ser Leu
    210                 215                 220

Gly Arg Asn Pro Thr Gly Val Pro Glu Gly Trp Leu
225                 230                 235

-continued

```
<210> SEQ ID NO 22
<211> LENGTH: 215
<212> TYPE: PRT
<213> ORGANISM: Escherichia coli

<400> SEQUENCE: 22
```

Met Glu Arg Asn Lys Leu Ala Arg Gln Ile Ile Asp Thr Cys Leu Glu
1               5                   10                  15

Met Thr Arg Leu Gly Leu Asn Gln Gly Thr Ala Gly Asn Val Ser Val
            20                  25                  30

Arg Tyr Gln Asp Gly Met Leu Ile Thr Pro Thr Gly Ile Pro Tyr Glu
        35                  40                  45

Lys Leu Thr Glu Ser His Ile Val Phe Ile Asp Gly Asn Gly Lys His
    50                  55                  60

Glu Gly Gly Lys Leu Pro Ser Ser Glu Trp Arg Phe His Met Ala Ala
65                  70                  75                  80

Tyr Gln Ser Arg Pro Asp Ala Asn Ala Val Val His Asn His Ala Val
                85                  90                  95

His Cys Thr Ala Val Ser Ile Leu Asn Arg Ser Ile Pro Ala Ile His
            100                 105                 110

Tyr Met Ile Ala Ala Gly Gly Asn Ser Ile Pro Cys Ala Pro Tyr
        115                 120                 125

Ala Thr Phe Gly Thr Arg Glu Leu Ser Glu His Val Ala Leu Ala Leu
    130                 135                 140

Lys Asn Arg Lys Ala Thr Leu Leu Gln His His Gly Leu Ile Ala Cys
145                 150                 155                 160

Glu Val Asn Leu Glu Lys Ala Leu Trp Leu Ala His Glu Val Glu Val
                165                 170                 175

Leu Ala Gln Leu Tyr Leu Thr Thr Leu Ala Ile Thr Asp Pro Val Pro
            180                 185                 190

Val Leu Ser Asp Glu Glu Ile Ala Val Val Leu Glu Lys Phe Lys Thr
        195                 200                 205

Tyr Gly Leu Arg Ile Glu Glu
    210                 215

```
<210> SEQ ID NO 23
<211> LENGTH: 216
<212> TYPE: PRT
<213> ORGANISM: Kyrpidia tusciae

<400> SEQUENCE: 23
```

Met Pro Glu Asn Ile Gln Glu Leu Arg Asn Ala Leu Leu Asp Ala Ala
1               5                   10                  15

His Arg Leu Ala Ala Arg Gly Leu Val Pro Gly Thr Thr Gly Asn Val
            20                  25                  30

Ser Leu Arg Ile Pro Gly Thr Asp Arg Phe Leu Ile Thr Pro Thr Gly
        35                  40                  45

Ile Pro Tyr Asp Val Leu His Ala Ser Asp Met Val Glu Val Asn Leu
    50                  55                  60

Gln Gly Ala Val Val Glu Gly Asn Arg Lys Pro Ser Ser Glu Thr Pro
65                  70                  75                  80

Leu His Thr Arg Ile Tyr His Asn His Pro Trp Ala Gly Ala Val Val
                85                  90                  95

His Thr His Ser Met Phe Ala Thr Thr Phe Ala Val Leu Asn Glu Ala
            100                 105                 110

Ile Pro Ala Val His Tyr Val Ile Ala Gly Met Gly Thr Asp Ile Pro

```
            115                 120                 125
Val Ala Gln Tyr Ala Thr Tyr Gly Ser Glu Asp Leu Ala Val Asn Ala
    130                 135                 140

Ala Glu Leu Ile Ser Pro Glu Gln Arg Ala Ile Leu Leu Gln Asn His
145                 150                 155                 160

Gly Val Ile Thr Val Gly Gly His Leu Glu Ala Leu His His Ala
                    165                 170                 175

Glu Thr Val Glu Tyr Leu Ala Glu Leu Tyr Tyr Arg Ser Arg Ser Ile
                180                 185                 190

Gly Ser Pro Asn Ile Leu Pro Glu Glu Ile Arg Arg Val Ala Glu
                195                 200                 205

Lys Phe Lys Thr Tyr Gly Gln Arg
    210                 215

<210> SEQ ID NO 24
<211> LENGTH: 516
<212> TYPE: PRT
<213> ORGANISM: Acinetobacter baylyi

<400> SEQUENCE: 24

Met Leu Val Leu Ser Ala Cys Asn Asp Asn His Asp Asn Asn Ser Thr
1               5                   10                  15

Ser Asp Arg Ser Ala Thr Val Glu Thr Ser Ala Tyr Val Gln Thr Lys
                20                  25                  30

Thr Pro Tyr Lys Pro Gln Gln Asp Leu Asn Thr Tyr Gln Ala Ala Pro
            35                  40                  45

Thr Gly Phe Gln Pro Val Phe Thr Glu Leu Val Ala Arg His Gly Ser
    50                  55                  60

Arg Gly Leu Ser Ser Met Lys Tyr Asp Leu Ala Leu Tyr Asn Leu Trp
65                  70                  75                  80

Lys Gln Ala Lys Thr Glu Asn Ala Leu Thr Pro Leu Gly Glu Gln Leu
                85                  90                  95

Gly Ala Asp Ile Glu Ala Ile Met Lys Ala Asn Ile Leu Leu Gly Tyr
            100                 105                 110

Gly Val Ala Gly Ile Arg Gln Phe Gly Tyr Gly Asn Glu Ser Gln Leu
        115                 120                 125

Gly Ile Glu Glu His Arg Gly Ile Ala Asp Arg Leu Leu Gln Arg Leu
    130                 135                 140

Pro Gln Leu Phe Asn Thr Ser Thr Leu Gly Gln Met Asp Ile Ala Val
145                 150                 155                 160

Gln Ser Ser Gly Val Asp Arg Ala Val Asp Ser Ala Lys Phe Phe Thr
                165                 170                 175

Asn Glu Leu Ile Val Lys Arg Pro Asp Leu Gln Glu Lys Ile Arg Pro
            180                 185                 190

Val Ser Tyr Ala Ser Leu Ser Ser Asp Thr Tyr Pro Ser Ile Asp Asp
        195                 200                 205

Gln Gly Val Asp Arg Phe Leu Leu Tyr Phe His Ser Leu Asn Lys Thr
    210                 215                 220

Thr Asp Leu Ser Gln Ile Asn Ser Thr Leu Arg Gln Asn Ile Tyr Asp
225                 230                 235                 240

Ala Ser Leu Lys Tyr Gln Asp Phe Glu Glu Asn Asp Ala Asp Leu Lys
                245                 250                 255

Gln Lys Leu Lys Glu Leu Ser Ser Asn Asn Ala Gln Gln Ile Ala
            260                 265                 270
```

```
Leu Lys Val Leu Thr Pro Leu Phe Lys Asp Glu Phe Ile Gln Lys Leu
            275                 280                 285

Gly Ser Gln Gly Tyr Thr Phe Ser Asn Thr Gly Ser Phe Thr Thr Thr
        290                 295                 300

Ala Ser Asn Gly Thr Gln Ile Thr Glu Lys Gly Lys Gly Lys Asn Thr
305                 310                 315                 320

Ile Ala Ser Thr Val Asp Ala Ala Tyr Leu Tyr Glu Leu Tyr Ser
                325                 330                 335

Ile Ala Pro Gly Met Lys Lys Glu Leu Gly Asn Thr Asp Phe Thr Lys
                340                 345                 350

Tyr Met Pro Ile Asp Ala Ala Lys Phe Tyr Ala Glu Tyr Asn Asp Ala
        355                 360                 365

Gln Asp Phe Tyr Glu Lys Gly Pro Ser Phe Thr Glu Ser Asn Gln Val
    370                 375                 380

Thr Ser Asn Ile Ala Asn Gly Leu Lys Gln Asp Phe Phe Ala Gln Val
385                 390                 395                 400

Asp Gln Val Ile Asn Lys Gln Gln His Lys Ala Val Leu Arg Phe
                405                 410                 415

Ala His Ala Glu Ile Ile Ile Pro Leu Ala Thr Ala Phe Glu Leu Lys
        420                 425                 430

Gly Met Met Thr Pro Leu Ala Leu Asn Gln Thr Tyr Ser Tyr Ser Thr
        435                 440                 445

Ser Thr Trp Arg Gly Glu Asp Ile Ser Pro Met Ala Ala Asn Met Gln
        450                 455                 460

Trp Asp Ile Tyr Gln Asn Ala Gln Gly Tyr Thr Leu Val Lys Met Leu
465                 470                 475                 480

Tyr Asn Glu Lys Glu Thr Leu Phe Lys Ser Ser Cys Asp Tyr Ala Arg
                485                 490                 495

Tyr Asn Ser Ser Ser Phe Tyr Tyr Asp Tyr Gln Lys Leu Lys Gln Cys
            500                 505                 510

Tyr Gly Ile Asn
            515

<210> SEQ ID NO 25
<211> LENGTH: 188
<212> TYPE: PRT
<213> ORGANISM: Escherichia coli

<400> SEQUENCE: 25

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
            20                  25                  30

His Tyr Gly Leu Gln Tyr Asp Ile Gln Ala Met Ile Ala Leu Asn Gly
        35                  40                  45

Ser Pro Thr Trp Arg Ile Ala Gln Ala Ile Glu Leu Asn Gln Ala
    50                  55                  60

Asp Leu Asp Pro His Ala Leu Ala Arg Glu Lys Thr Glu Ala Val Arg
65                  70                  75                  80

Ser Met Leu Leu Asp Ser Val Gly Pro Leu Pro Leu Val Asp Val Val
                85                  90                  95

Lys Ser Trp His Gly Arg Arg Pro Met Ala Val Gly Thr Gly Ser Glu
            100                 105                 110

Ser Ala Ile Ala Glu Ala Leu Leu Ala His Leu Gly Leu Arg His Tyr
        115                 120                 125
```

```
Phe Asp Ala Val Val Ala Ala Asp His Val Lys His His Lys Pro Ala
    130                 135                 140
Pro Asp Thr Phe Leu Leu Cys Ala Gln Arg Met Gly Val Gln Pro Thr
145                 150                 155                 160
Gln Cys Val Val Phe Glu Asp Ala Asp Phe Gly Ile Gln Ala Ala Arg
                165                 170                 175
Ala Ala Gly Met Asp Ala Val Asp Val Arg Leu Leu
            180                 185
```

<210> SEQ ID NO 26
<211> LENGTH: 216
<212> TYPE: PRT
<213> ORGANISM: Haemophilus influenzae

<400> SEQUENCE: 26

```
Met Asn Arg Ala Glu Leu Ser Gln Lys Ile Ile Asp Thr Cys Leu Glu
1               5                   10                  15
Met Thr Lys Leu Gly Leu Asn Gln Gly Thr Ala Gly Asn Val Ser Val
            20                  25                  30
Arg Tyr Lys Asp Gly Met Leu Ile Thr Pro Thr Gly Met Pro Tyr His
        35                  40                  45
Leu Met Lys Thr Glu Asn Ile Val Tyr Val Asp Gly Asn Gly Lys His
    50                  55                  60
Glu Glu Asn Lys Leu Pro Ser Ser Glu Trp Gln Phe His Leu Ser Val
65                  70                  75                  80
Tyr His Thr Arg Pro Glu Ala Asn Ala Val Val His Asn His Ser Ile
                85                  90                  95
His Cys Ala Gly Leu Ser Ile Leu Glu Lys Pro Ile Pro Ala Ile His
            100                 105                 110
Tyr Met Val Ala Val Ser Gly Thr Asp His Ile Pro Cys Val Pro Tyr
        115                 120                 125
Ala Thr Phe Gly Ser His Lys Leu Ala Ser Tyr Val Ala Thr Gly Ile
    130                 135                 140
Lys Glu Ser Lys Ala Ile Leu Leu Ala His His Gly Leu Ile Thr Cys
145                 150                 155                 160
Gly Glu Asn Leu Asp Lys Ala Leu Trp Leu Ala Gln Glu Val Glu Val
                165                 170                 175
Leu Ala Ser Trp Tyr Leu Lys Leu Leu Ser Thr Gly Leu Glu Ile Pro
            180                 185                 190
Leu Leu Ser Lys Glu Gln Met Gln Val Val Leu Gly Lys Phe His Thr
        195                 200                 205
Tyr Gly Leu Arg Ile Glu Glu Ser
    210                 215
```

<210> SEQ ID NO 27
<211> LENGTH: 216
<212> TYPE: PRT
<213> ORGANISM: Fusobacterium varium

<400> SEQUENCE: 27

```
Met Lys Leu Gln Thr Glu Arg Glu Lys Val Val Lys Tyr Leu Asn Leu
1               5                   10                  15
Leu Ile Glu Lys Gly Leu Thr Lys Gly Thr Gly Gly Asn Ile Ser Ile
            20                  25                  30
Tyr Asn Glu Lys Glu Asn Leu Val Ala Ile Ser Pro Ser Ser Val Pro
        35                  40                  45
```

```
Tyr Asp Ile Leu Lys Pro Glu Asp Ile Met Val Val Asp Leu Asp Gly
    50                  55                  60

Lys Val Val Asp Gly Asn Pro Met Tyr Val Pro Ser Ser Glu Thr Gly
65                  70                  75                  80

Met His Leu Lys Val Tyr Lys Gly Arg Glu Asp Ile Lys Ala Leu Val
                85                  90                  95

His Thr His Ala Met Tyr Cys Thr Thr Ile Ser Cys Leu Arg Glu Pro
            100                 105                 110

Leu Lys Ala Val Asp Tyr Met Leu Ala Ile Thr Gly Thr Asn Glu Val
        115                 120                 125

Lys Cys Ala Glu Tyr Ala Met Phe Gly Thr Pro Glu Leu Ala Glu Asn
    130                 135                 140

Ala Phe Glu Ala Met Arg Gly Ala Lys Ala Cys Leu Leu Ala Asn His
145                 150                 155                 160

Gly Val Asn Val Gly Ala Ile Asp Ile Glu Asn Ala Phe Ala Ile Thr
                165                 170                 175

Glu Tyr Val Glu Phe Cys Ala Glu Leu Tyr Val Lys Ala Arg Ser Ile
            180                 185                 190

Gly Asn Pro Val Ile Leu Ser Lys Glu Ile Asp Arg His Ile Ala
        195                 200                 205

Lys Phe Gly Ser Tyr Cys Lys Leu
    210                 215

<210> SEQ ID NO 28
<211> LENGTH: 221
<212> TYPE: PRT
<213> ORGANISM: Brachyspira murdochii

<400> SEQUENCE: 28

Met Ile Ser Gln Leu Asn Glu Tyr Arg Lys Leu Leu Ser Asn Asp Ile
1               5                   10                  15

Ile Lys Thr Cys Leu Arg Met Gln Lys Asp Gly Ile Asn Gln Gly Thr
            20                  25                  30

Ser Gly Asn Val Ser Val Arg Phe Glu Asn Gly Met Leu Ile Thr Pro
        35                  40                  45

Ser Ser Met Pro Tyr Asp Thr Met Lys Ala Glu Asn Ile Val Phe Val
    50                  55                  60

Asp Glu Asn Gly Lys Ser Glu Gly Glu Gly Lys Arg Pro Ser Ser Glu Trp
65                  70                  75                  80

Arg Phe His Leu Ser Ile Leu Lys Asp Asn Pro Asp Phe Asn Cys Val
                85                  90                  95

Ile His Ser His Ser Ile Tyr Ser Thr Val Val Ser Ile Met Gly Val
            100                 105                 110

Asp Tyr Ile Pro Ala Ile His Tyr Met Ile Ala Val Ala Gly Gly Lys
        115                 120                 125

Ile Ile Pro Cys Ala Glu Tyr Ala Thr Tyr Gly Thr Glu Glu Leu Cys
    130                 135                 140

Asn Asn Ile Ser Lys Ala Met Lys Gly Tyr Lys Ala Cys Ile Met Lys
145                 150                 155                 160

Asn His Gly Leu Val Val Ser Asp Ser Thr Ile Glu Lys Ala Tyr Gly
                165                 170                 175

Val Leu Val Glu Val Glu Asn Ile Ser Arg Glu Phe Val Glu Leu Ser
            180                 185                 190

Lys Ile Gly Lys Tyr Asn Val Leu Ser Asp Glu Asp Met Asp Ile Ile
```

```
                195                 200                 205
Leu Lys Lys Phe Gly Asn Tyr Gly Leu Asn Ala Gln Lys
    210                 215                 220

<210> SEQ ID NO 29
<211> LENGTH: 212
<212> TYPE: PRT
<213> ORGANISM: Acetoanaerobium sticklandii

<400> SEQUENCE: 29

Met Met Glu Tyr Glu Lys Glu Gln Val Val Arg Tyr Gly Lys Lys Leu
1               5                  10                  15

Ile Asp Arg Arg Leu Thr Thr Gly Ser Gly Gly Asn Ile Ser Val Tyr
                20                  25                  30

Asn Arg Glu Gln Asn Leu Val Ala Ile Ser Pro Ser Gly Leu Asp Tyr
            35                  40                  45

Tyr Glu Thr Thr Pro Glu Asp Ile Val Ile Leu Asp Ile Asp Gly Asn
        50                  55                  60

Leu Val Glu Gly Lys Asn Arg Pro Ser Ser Glu Ala Gly Met His Leu
65                  70                  75                  80

Ala Phe Tyr Lys Asn Arg Ala Asp Val Ser Gly Ile Val His Thr His
                85                  90                  95

Ser Lys Phe Ala Thr Ala Ile Ala Cys Met Gly Trp Glu Leu Pro Ala
            100                 105                 110

Val His Tyr Leu Ile Gly Met Ala Gly His Arg Val Lys Cys Thr Gly
        115                 120                 125

Tyr Ala Thr Tyr Gly Ser Asp Glu Leu Ala Lys Lys Ala Leu Glu Thr
    130                 135                 140

Ile Gly Asp Ser Asn Ala Val Leu Leu Ala Asn His Gly Leu Ile Ala
145                 150                 155                 160

Leu Gly Glu Asp Val Asp Arg Ala Phe Ser Thr Ala Glu His Leu Glu
                165                 170                 175

Phe Val Ser Glu Val Tyr Tyr Leu Thr Lys Thr Leu Gly Thr Pro Asn
            180                 185                 190

Ile Leu Ser Asp Glu Asn Met Asp Glu Val Met Lys Lys Phe Gly Thr
        195                 200                 205

Phe Arg Tyr Arg
    210

<210> SEQ ID NO 30
<211> LENGTH: 226
<212> TYPE: PRT
<213> ORGANISM: Blautia hydrogenotrophica

<400> SEQUENCE: 30

Met Leu Leu Gln Lys Glu Arg Glu Leu Val Val Glu Tyr Gly Lys Lys
1               5                  10                  15

Met Ser Ser Ser Gly Leu Ser Lys Gly Thr Ser Gly Asn Ile Ser Ile
                20                  25                  30

Tyr Asn Arg Lys Glu Gln Leu Met Ala Ile Ser Pro Ser Gly Ile Gly
            35                  40                  45

Tyr Phe Glu Thr Met Pro Glu Asp Val Val Ile Met Asp Leu His Gly
        50                  55                  60

Asn Ile Val Glu Gly Asp Lys Lys Pro Ser Ser Glu Trp Gly Leu His
65                  70                  75                  80

Thr Val Phe Tyr Leu Asn Lys Pro Asp Val Glu Ala Val Val His Thr
```

His Ser Thr Phe Cys Thr Thr Phe Ala Cys Leu Asn Gln Pro Ile Arg
            100                 105                 110

Ala Leu His Tyr Val Ile Gly Gly Ala Gly Thr Ala Thr Val Pro Cys
            115                 120                 125

Ala Pro Tyr Arg Thr Phe Gly Thr Pro Glu Leu Ala Glu Ala Ala Ile
            130                 135                 140

Glu Ala Cys Gly Lys Gly Lys Ala Val Leu Leu Ala Asn His Gly Leu
145                 150                 155                 160

Leu Thr Cys Gly Pro Asn Ile Gly Lys Ala Phe Gly Leu Ala Val Asn
                    165                 170                 175

Met Glu Phe Cys Ala Glu Met Gln Phe Arg Ala Met Cys Val Gly Asp
                180                 185                 190

Pro Val Ile Leu Ser Asp Ser Glu Met Glu Asn Val Met Glu Arg Phe
            195                 200                 205

Gln Ser Tyr Gly Gln Pro Lys Lys Asp Gly Glu Ser Lys Glu Pro Asn
210                 215                 220

Cys Tyr
225

<210> SEQ ID NO 31
<211> LENGTH: 213
<212> TYPE: PRT
<213> ORGANISM: Enterococcus gilvus

<400> SEQUENCE: 31

Met Met Glu Lys Glu Lys Glu Leu Leu Val Glu Tyr Gly Lys Leu Leu
1               5                   10                  15

Ile Ser Thr Gly Leu Thr Thr Gly Thr Gly Gly Asn Ile Ser Ile Tyr
            20                  25                  30

Asn Pro Asp Glu Gln Ile Met Ala Ile Thr Pro Ser Gly Ile Asp Tyr
            35                  40                  45

Phe Glu Met Thr Val Thr Asp Ile Val Leu Leu Asp Leu Asp Gly Lys
    50                  55                  60

Val Val Glu Gly Lys Arg Lys Pro Ser Ser Glu Trp Gln Met His Val
65                  70                  75                  80

Ile Asn Tyr Gln Lys Arg Ser Asp Thr Ile Arg Ala Val Val His Ala
                85                  90                  95

His Ser Thr Phe Ser Ser Ile Leu Ala Thr Cys Arg Lys Ser Leu Pro
            100                 105                 110

Ala Ser Asn Tyr Met Ile Ala Ile Ala Gly Gly Asp Val Arg Cys
            115                 120                 125

Ser Lys Tyr Ala Thr Phe Gly Thr Glu Glu Leu Ala Glu Tyr Ala Phe
    130                 135                 140

Glu Ala Met Glu Asp Arg Tyr Ala Cys Phe Leu Ala Asn His Gly Leu
145                 150                 155                 160

Leu Thr Gly Gly Phe Thr Leu Lys Glu Ala Phe Ser Val Ala Val Glu
                    165                 170                 175

Ile Glu Arg Leu Ala Gly Leu His Ile Gly Ala Ser Leu Phe Gly Ser
                180                 185                 190

Pro Val Ile Leu Asp Glu Ser Asp Met Lys Lys Val Gln Glu Arg Phe
            195                 200                 205

Pro Ser Tyr Gly Gln
    210

<210> SEQ ID NO 32
<211> LENGTH: 221
<212> TYPE: PRT
<213> ORGANISM: Methylocella silvestris

<400> SEQUENCE: 32

Met Glu Lys Arg Gly Glu Phe Ala Val Arg Gln Ser Ile Ile Asp Gly
1               5                   10                  15

Cys Leu Ala Leu Ala Arg Leu Gly Val Asn Gln Gly Thr Ala Gly Asn
            20                  25                  30

Ile Ser Val Arg Trp Asn Gly Gly Leu Leu Ile Thr Pro Ser Gly Leu
        35                  40                  45

Pro Tyr Asp Glu Met Gly Ala Asp Asp Ile Val Phe Met Ala Met Asp
    50                  55                  60

Gly Ser Phe Arg His Pro Leu Ala Pro Ser Ser Glu Trp Arg Phe His
65                  70                  75                  80

Arg Asp Ile Leu Ala Arg Arg Pro Glu Val Gly Ala Val Val His Ala
                85                  90                  95

His Pro Ile Phe Cys Thr Ala Phe Ala Met Cys Arg Met Glu Ile Pro
            100                 105                 110

Ala Ala His Tyr Met Ile Ala Ala Ala Gly Gly Pro Thr Ile Arg Cys
        115                 120                 125

Ala Arg Tyr Glu Ser Tyr Gly Thr Pro Glu Leu Ser Glu Ala Ala Leu
    130                 135                 140

Glu Ala Leu Glu Gly Arg Ala Cys Thr Leu Leu Ala Asn His Gly Met
145                 150                 155                 160

Ile Ala Thr Gly Pro Asp Leu Ala Glu Ala Leu Trp Leu Ala Val Glu
                165                 170                 175

Thr Glu Thr Leu Ala Arg Gln Tyr Ala Ala Ala Leu Gln Ile Gly Ala
            180                 185                 190

Pro Val Ile Leu Asp Asp Ala Glu Ile Ala Lys Thr Val Glu Lys Phe
        195                 200                 205

Lys Asp Tyr Gly Leu Arg Gly Arg Asn Arg Arg Asp Gly
    210                 215                 220

<210> SEQ ID NO 33
<211> LENGTH: 217
<212> TYPE: PRT
<213> ORGANISM: Roseobacter litoralis

<400> SEQUENCE: 33

Met Gly Gln Arg Glu Asp Ile Ile Thr Ala Cys Lys Lys Leu Glu Ala
1               5                   10                  15

Asp Gly Leu Asn Arg Gly Ala Ser Gly Asn Val Ser Met Arg Asp Gly
            20                  25                  30

Asp His Met Leu Ile Thr Pro Ser Ala Val Gly Tyr Asp Val Ile Ala
        35                  40                  45

Pro Asp Met Ile Ala Arg Met Arg Leu Asp Asp Asn Gly Gly Trp
    50                  55                  60

Glu Gly Pro Asn Lys Pro Ser Ser Glu Trp Arg Phe His Arg Asp Ile
65                  70                  75                  80

Leu Arg Gly Arg Pro Asp Ile Asn Ala Val Val His Thr His Ala Pro
                85                  90                  95

Tyr Ala Thr Ile Leu Ala Ile Ala Arg Lys Pro Ile Pro Ala Val His
            100                 105                 110

Tyr Met Ile Ala Ala Phe Gly Gly Pro Asp Ile Arg Val Cys Asp Tyr
            115                 120                 125

Ala Arg Tyr Gly Thr Ala Glu Leu Ser Glu His Ile Leu Glu Ala Met
130                 135                 140

Glu Gly Arg Asn Gly Cys Leu Met Ala Asn His Gly Met Val Val Gly
145                 150                 155                 160

Ala Ser Asp Leu Thr Arg Ala Leu Trp Leu Ala Gly Glu Leu Glu Ala
                165                 170                 175

Leu Ala His Gln Tyr Val His Thr Leu Ala Ile Gly Pro Val Leu
            180                 185                 190

Leu Ser Asp Gly Glu Ile Glu Glu Thr Ala Lys Gly Phe Glu Ser Tyr
            195                 200                 205

Gly Val Gln Ala Lys Asp Thr Ala Gln
    210                 215

<210> SEQ ID NO 34
<211> LENGTH: 218
<212> TYPE: PRT
<213> ORGANISM: Rhodobacter sphaeroides

<400> SEQUENCE: 34

Met Asn Glu Met Ser Asp Leu Ser Asp Leu Ala Lys Arg Glu Glu Ile
1               5                   10                  15

Ile Arg Gln Cys Leu Glu Met Asn Arg Ser Gly Leu Asn Gln Gly Thr
            20                  25                  30

Ser Gly Asn Ile Ser Val Arg His Gly Glu Gly Met Leu Ile Thr Pro
        35                  40                  45

Thr Ser Leu Pro Tyr Asp Thr Leu Val Pro Glu Asp Ile Val Phe Val
50                  55                  60

Ser Met Glu Gly Glu Val Arg Gly Arg His Lys Pro Ser Ser Glu Trp
65                  70                  75                  80

Arg Phe His Arg Asp Ile Leu Arg Glu Arg Ala Asp Val Asn Ala Val
                85                  90                  95

Val His Ala His Pro Thr Tyr Cys Thr Thr Leu Ala Ile Met Asn Arg
            100                 105                 110

Glu Ile Pro Ser Ile His Tyr Met Leu Ala Val Val Gly Gly Pro Asn
        115                 120                 125

Ile Arg Cys Ala Pro Tyr Ala Ile Tyr Gly Ser Glu Glu Leu Ser Arg
130                 135                 140

Asn Ala Val Glu Ala Leu His Asp Arg Lys Ala Cys Leu Leu Glu His
145                 150                 155                 160

His Gly Met Ile Ala Val Gly Lys Ser Leu Ala Gln Ala Met Trp Leu
                165                 170                 175

Ala Val Glu Val Glu Thr Leu Ala Arg Gln Tyr His Gly Cys Leu Gln
            180                 185                 190

Ile Gly Glu Pro Arg Leu Leu Ser Glu Arg Gln Ile Gln Asp Val Ile
        195                 200                 205

Asp Lys Ile Ala Gly Tyr Gly His Gln Gly
    210                 215

<210> SEQ ID NO 35
<211> LENGTH: 286
<212> TYPE: PRT
<213> ORGANISM: Escherichia coli

<400> SEQUENCE: 35

```
Met Ser Ile Ile Ser Thr Lys Tyr Leu Leu Gln Asp Ala Gln Ala Asn
1               5                   10                  15

Gly Tyr Ala Val Pro Ala Phe Asn Ile His Asn Ala Glu Thr Ile Gln
            20              25                  30

Ala Ile Leu Glu Val Cys Ser Glu Met Arg Ser Pro Val Ile Leu Ala
        35              40                  45

Gly Thr Pro Gly Thr Phe Lys His Ile Ala Leu Glu Glu Ile Tyr Ala
    50              55                  60

Leu Cys Ser Ala Tyr Ser Thr Thr Tyr Asn Met Pro Leu Ala Leu His
65              70                  75                      80

Leu Asp His His Glu Ser Leu Asp Asp Ile Arg Arg Lys Val His Ala
            85                  90                      95

Gly Val Arg Ser Ala Met Ile Asp Gly Ser His Phe Pro Phe Ala Glu
            100                 105                 110

Asn Val Lys Leu Val Lys Ser Val Val Asp Phe Cys His Ser Gln Asp
            115                 120                 125

Cys Ser Val Glu Ala Glu Leu Gly Arg Leu Gly Gly Val Glu Asp Asp
130                     135                 140

Met Ser Val Asp Ala Glu Ser Ala Phe Leu Thr Asp Pro Gln Glu Ala
145                 150                 155                 160

Lys Arg Phe Val Glu Leu Thr Gly Val Asp Ser Leu Ala Val Ala Ile
                165                 170                 175

Gly Thr Ala His Gly Leu Tyr Ser Lys Thr Pro Lys Ile Asp Phe Gln
            180                 185                 190

Arg Leu Ala Glu Ile Arg Glu Val Val Asp Val Pro Leu Val Leu His
        195                 200                 205

Gly Ala Ser Asp Val Pro Asp Glu Phe Val Arg Arg Thr Ile Glu Leu
        210                 215                 220

Gly Val Thr Lys Val Asn Val Ala Thr Glu Leu Lys Ile Ala Phe Ala
225                 230                 235                 240

Gly Ala Val Lys Ala Trp Phe Ala Glu Asn Pro Gln Gly Asn Asp Pro
                245                 250                 255

Arg Tyr Tyr Met Arg Val Gly Met Asp Ala Met Lys Glu Val Val Arg
            260                 265                 270

Asn Lys Ile Asn Val Cys Gly Ser Ala Asn Arg Ile Ser Ala
            275                 280                 285
```

METHOD FOR PREPARING PHOSPHORYLATED KETO POLYOLS, DERIVATIVES THEREOF AND USES THEREOF

CROSS-REFERENCE TO RELATED APPLICATION

This application is the U.S. national stage application of International Patent Application No. PCT/EP2018/063400, filed May 22, 2018.

The Sequence Listing for this application is labeled "Seq-List.txt" which was created on Oct. 27, 2019 and is 80 KB. The entire content of the sequence listing is incorporated herein by reference in its entirety.

FIELD OF THE INVENTION

The present invention relates to the preparation of phosphorylated keto polyols by biocatalysis and uses thereof.

BACKGROUND OF THE INVENTION

Chiral compounds are key intermediates for the synthesis of valuable compounds, especially in the pharmaceutical field wherein chirality plays a crucial role in biological activity. Due to the multitude of biological pathways controlled by carbohydrates and sugar mimics, efforts have been directed toward de novo syntheses of rare sugars. Rare monosaccharides have been extensively evaluated for biological and functional uses. These compounds can interact with a number of biological receptors that have a wide range of potential chemotherapeutic uses (Nakajima et al., Cancer Res. 2004, 64, 1794-1801). Branched sugars and other keto or aldo polyol derivatives are molecular platforms of interest which can give access of new therapeutic compounds such as antibiotics and also represent promising biological compounds of interest in the medical field. These compounds are also valuable starting and intermediary compounds in biofuel and chemical industries.

Unfortunately, an important factor restricting the use of rare sugars as well as other keto or aldo polyol derivatives is their limited availability, due to the limited available synthetic methods. Indeed, the inherent multifunctionality of sugars and analogs thereof is a challenge for organic chemists. Traditional synthesis of aldo or keto polyols generally requires many protection and deprotection steps. Moreover, the compounds may comprise several stereo-centers. The control of the configuration of these stereo-centers requires very sophisticated synthesis and purification strategies which are expensive, time-consuming and suffer from limited yields.

An alternative to traditional chemical synthesis is biocatalysis. The use of enzymes offers the main advantages of stereospecificity, regioselectivity and enantioselectivity while allowing mild conditions of reaction and minimizing the use of protective groups and products, such as organic solvents, potentially harmful to environment. Enzymes can also give access to compounds which are very difficult to prepare in few steps by traditional chemistry. Therefore, there is a need of new methods for producing ketol polyols and derivatives thereof by biocatalysis.

SUMMARY OF THE INVENTION

The invention relates to the use of a class II DHAP aldolase such as an enzyme having a RhaD activity, a FucA activity, or a TagA activity, optionally a RhaD activity or a FucA activity for promoting the reaction of dihydroxyacetone phosphate (DHAP) with a ketone selected from a 1,2-diketone and a ketone having, at a position alpha of the carbonyl group, a substituent selected from the group consisting of:

OH, F, Cl, Br, I, azido, cyano, nitro, —COOH, —SO$_3$H, —C(F)$_3$, —C(Cl)$_3$, —C(Br)$_3$, —C(I)$_3$, —NHC(=O)R, —NHC(=O)OR, —OR, —SR, —SO$_2$R, —C(=O)R, —C(=O)NHR, —OC(=O)OR, —C(=O)OR, —C(=O)SR, wherein R is a substituted or unsubstituted C$_1$-C$_{10}$ alkyl, a substituted or unsubstituted C$_5$-C$_{10}$ aryl or a substituted or unsubstituted C$_4$-C$_{10}$ heteroaryl group, N(R$^3$)$_3^+$ wherein each R$^3$ is independently selected from H, C$_1$-C$_{10}$ alkyl and C$_5$-C$_{10}$ aryl, OP(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted C$_5$-C$_{10}$ aryl, a substituted or unsubstituted C$_4$-C$_{10}$ heteroaryl group, substituted or unsubstituted C$_1$-C$_{10}$ alkoxy and substituted or unsubstituted C$_5$-C$_{10}$ aryloxy, preferably in the preparation of a phosphorylated keto polyol.

The invention also relates to a method for preparing a phosphorylated keto polyol of formula (I)

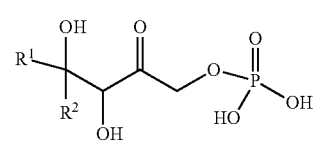

or a cyclic hemiketal isomer thereof,
said method comprising a step of reacting dihydroxyacetone phosphate (DHAP) with a ketone of formula (III):

selected from a 1,2-diketone and a ketone having a substituent X at a position alpha of the carbonyl group,
in the presence of a class II DHAP aldolase such as an enzyme having a RhaD activity, a FucA activity, or a TagA activity
wherein R$^1$ and R$^2$ are such that:
The molecular weight of the ketone of formula (III) is less than 600 g·mol$^{-1}$,
neither R$^1$ nor R$^2$ are H, and
the carbonyl shown in formula (III) is included in a moiety selected from:

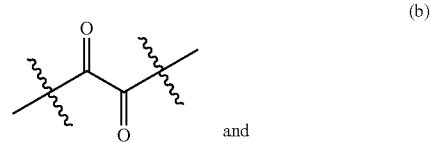

and

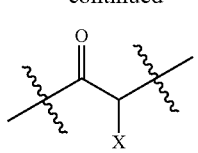

wherein X is selected from the group consisting of:
OH, F, Cl, Br, I, —N$_3$, cyano, nitro, —COOH, —SO$_3$H, —C(F)$_3$, —C(Cl)$_3$, —C(Br)$_3$, —C(I)$_3$, —NHC(=O)R, —NHC(=O)OR, —OR, —SR, —SO$_2$R, —C(=O)R, —C(=O)OR, —C(=O)NHR, —OC(=O)OR, —C(=O)SR, wherein R is a substituted or unsubstituted C$_1$-C$_{10}$ alkyl, a substituted or unsubstituted C$_5$-C$_{10}$ aryl or a substituted or unsubstituted C$_4$-C$_{10}$ heteroaryl group, —N(R$^3$)$_3^+$ wherein each R$^3$ is independently selected from H, C$_1$-C$_{10}$ alkyl and C$_5$-C$_{10}$ aryl, OP(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted C$_5$-C$_{10}$ aryl, a substituted or unsubstituted C$_4$-C$_{10}$ heteroaryl group, substituted or unsubstituted C$_1$-C$_{10}$ alkoxy and substituted or unsubstituted C$_5$-C$_{10}$ aryloxy.

In some embodiments, the method of the invention is such that the ketone of formula (III) is characterized in that:

R$^1$ and R$^2$ are independently selected from the group consisting of —(CH$_2$)$_p$-Ph, —COOH, —C(=O)—R, —CH$_2$—C(=O)—R, —C(=O)OR, and C$_1$-C$_{10}$, preferably C$_1$-C$_6$ alkyl optionally substituted with at least one group (e.g. at least 2, 3, 4 or 5) selected from —OH, C$_1$-C$_3$ alkoxy, C$_1$-C$_3$ alkyl, —F, —Cl, —Br, —I, wherein:

Ph is a phenyl optionally substituted by one or several substituents preferably selected from halogens, —OH, C$_1$-C$_6$ alkyl, and C$_1$-C$_6$ alkoxy p is an integer from 1 to 6, preferably 1, 2 or 3, and R is a C$_1$-C$_6$ alkyl optionally substituted by one or several substituents preferably selected from halogens, —OH, C$_1$-C$_3$ alkyl, and C$_1$-C$_3$ alkoxy, or R$^1$ and R$^2$ form together, with the carbonyl group, a C$_5$-C$_6$ ring bearing at least one group selected from —OH, —OCH$_3$, —F, —Cl, —Br, —I, at position alpha of the carbonyl group or a second oxo group at position alpha or beta of the carbonyl group.

In some other embodiments, the ketone of formula (III) is such that:

R$^1$ and R$^2$ are independently selected from the group consisting of —(CH$_2$)$_p$-Ph, wherein Ph is a phenyl, and p is 1 or 2; COOH; —CH$_2$—C(=O)—R, —C(=O)—R wherein R is a C$_1$-C$_3$ alkyl; C$_1$-C$_6$ alkyl optionally substituted with at least one group selected from —OH, —OCH$_3$ and —Cl, or R$^1$ and R$^2$ form together, with the carbonyl group, a C$_6$ ring bearing at least one group selected from —OH, —OCH$_3$, and —Cl at position alpha of the carbonyl group or bearing a second oxo group at position alpha or beta of the carbonyl group.

In some embodiments of the method or the use of the invention, the enzyme belongs to EC 4.1.2.19, to EC 4.1.2.17 or to EC 4.1.2.40, optionally EC 4.1.2.19 or to EC 4.1.2.17. For instance, the enzyme is an enzyme having a RhaD aldolase activity and comprising a polynucleotide having at least 30%, preferably, at least 60% of sequence identity with an amino acid sequence selected from SEQ ID NO:1-SEQ ID NO:21. As a further example, the enzyme has a FucA activity and comprises a polynucleotide having at least 30%, preferably at least 60% of sequence identity with an amino acid sequence selected from SEQ ID NO:22, SEQ ID NO:23 and SEQ ID NO:26-SEQ ID NO:34. As a further example, the enzyme has a TagA activity and comprises a polynucleotide having at least 50%, preferably at least 60% of sequence identity with an amino acid sequence selected from SEQ ID NO:35.

The aldolase having the RhaD, FucA or TagA activity, optionally RhaD or FucA activity, may be a purified enzyme, present in free form or immobilized on a solid support. In some embodiments, the reaction medium contains a metallic divalent cation, preferably Co$^{2+}$.

The method of the invention may further comprise a step of recovering and/or purifying the phosphorylated keto polyol of formula (I).

The present invention also relates to a process for preparing a keto polyol of formula (II):

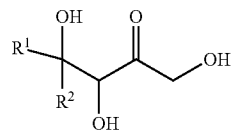

or a cyclic hemiketal isomer thereof, wherein R$^1$ and R$^2$ are as described above, said process comprises the steps of:

iii. Preparing a phosphorylated keto polyol of formula (I) as defined above, by implementing the method of the invention, and iv. Dephosphorylating the phosphorylated keto polyol obtained in step (i), so as to obtain the keto polyol of formula (II) or a cyclic hemiketal isomer thereof.

In some embodiments of the process of the invention, step (ii) is performed by contacting the phosphorylated keto polyol with a phosphatase.

The invention also relates to a compound selected from:

a phosphorylated keto polyol of formula (I)

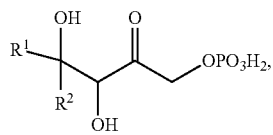

and a keto polyol of formula (II)

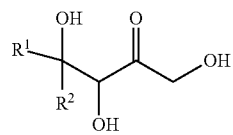

wherein R$^1$ and R$^2$ are such that
said compound comprises a moiety selected from:

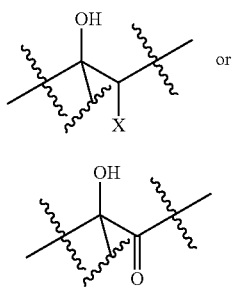

wherein X is selected from the group consisting of —OH, —OCH$_3$, and a halogen, and
R$^1$ and R$^2$ are independently selected from the group consisting of —(CH$_2$)$_p$-Ph, —OH, —CH$_2$—C(=O)—R, —COOH, —C(=O)—R, unsubstituted C$_1$-C$_3$ alkyl, C$_1$-C$_3$ alkyl substituted with at least one group selected from —OH, —OCH$_3$, and a halogen; wherein Ph is a phenyl, p is 1 or 2, and R is a C$_1$-C$_3$ alkyl; or
R$_1$ and R$_2$ form together, with the carbon bearing the tertiary alcohol function, a C$_6$ ring bearing at least one group selected from —OH, —OCH$_3$, and a halogen at position alpha of the carbonyl group or bearing a second carbonyl group at position alpha or beta of the carbonyl group,
A salt thereof, and
a cyclic hemiketal isomer thereof,
with proviso that said compound is not the compound (1b) or (2b) as shown in table 4, or a cyclic hemiketal isomer or salt thereof.

For instance, the compound of the invention may be selected from compounds (1)-(12) and (3b)-(12b) as shown in tables 4 and 5.

In another aspect, the invention relates to a process for preparing a compound of interest comprising:
preparing a keto polyol of formula (II) by the process as defined above or a phosphorylated keto polyol of formula (I) by the method as defined above and
using the resulting keto polyol, or the resulting phosphorylated keto polyol for producing the compound of interest.

The compound of interest may be a building block for chemical synthesis such as a polyol, an amino polyol, and a furfural derivative or a drug, for instance an antibiotic.

DETAILED DESCRIPTION OF THE INVENTION

Rhamnulose-1-phosphate aldolases (RhaD aldolases) are metal-dependent class II aldolases which reversibly catalyze the asymmetric addition of dihydroxyacetone phosphate (DHAP) to (S)-lactaldehyde (L-Lac) to give L-rhamnulose-1-phosphate (L-R1P). This group of enzymes corresponds to the enzyme class E.C 4.1.2.19.

RhaD of *E. coli* was shown to accept a variety of aldehydes as acceptor substrates (Fessner et al., *Angew. Chem. Int. Ed. Engl*, 1991, 30, 555-558) while being restrictive with respect to the donor substrate, namely DHAP. To the knowledge of the Inventors, the prior art does not describe any acceptor substrate other than aldehydes for class II DHAP aldolases, in particular for RhaD aldolases. As of today, only certain pyruvate aldolases has been described as accepting certain ketones as acceptor substrates for aldol reaction wherein the donor substrate is pyruvic acid, and not DHAP.

The Inventors surprisingly showed that Rhamnulose-1-phosphate aldolases of EC 4.1.2.19 are able to catalyze the reaction between DHAP as donor and an activated ketone as acceptor.

In particular, the Inventors showed that RhaD aldolase from *Bacteroides thetaiotaomicron* (SEQ ID NO:10) was able to catalyze the reaction between DHAP and dihydroxyacetone (DHA) to give phosphorylated dendroketose, which can isomerize into a hemiketal cyclic isomer:

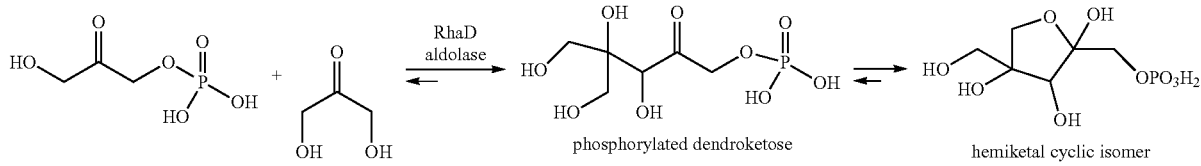

phosphorylated dendroketose         hemiketal cyclic isomer

The Inventors also showed that other RhaD aldolases, namely RhaD of SEQ ID NO: 1 to NO:9 and SEQ ID NO:11 to SEQ ID NO:21 were able to catalyze the same reaction. Noteworthy, these enzymes display a high degree of dispersity in terms of amino acid sequence. The Inventors further showed that L-fuculose-1-phosphate aldolase (FucA) from *E. coli* (SEQ ID NO:22), from *Haemophilus influenzae* (SEQ ID NO:26) and FucA from *Kyrpidia tusciae* (SEQ ID NO:23) were able to catalyze the reaction of DHAP with dihydroxyacetone (DHA), so as the tested similar sequences of SEQ ID NO:27-SEQ ID NO:34. The Inventors also further showed that D-tagatose-1,6 biphosphate aldolase (TagA) from *E. coli* (SEQ ID NO:35) is able to catalyze the reaction of DHAP with dihydroxyacetone (DHA).

Taken together, these results suggest that the ability to catalyze the reaction between DHAP and an activated ketone as acceptor substrate may be a specific feature of class II DHAP aldolases, in particular DHAP aldolases of EC 4.1.2.19 family (RhaD), EC 4.1.2.17 family (FucA), and EC 4.1.2.40 family (TagA), especially EC 4.1.2.19 family (RhaD) and EC 4.1.2.17 family (FucA). To that respect, the Inventors tested several aldolases which did not belong to class II DHAP aldolases, such as DHA aldolases (i.e. FSA of *E. coli*), deoC aldolase, class I DHAP aldolases and pyruvate aldolases (enzymes belonging to Pfam family PF03328) which all failed to catalyze the reaction between DHA and DHAP.

The Inventors also investigated the substrate spectrum of the RhaD aldolases with respect to ketones. The Inventors demonstrated that RhaD of various microorganisms including *E. coli* were unable to catalyze the reaction of DHAP with non-activated ketones such as acetone, butanone, and cyclopentanone. In contrast, high rates of conversion were obtained with 1,3-diketones (β-diketones), 1,2-diketones (α-diketones) and more generally with ketones having an activating group at an alpha position of the carbonyl group. Such electrophile substrates encompass alpha-hydroxy ketones, alpha-keto acids, alpha-halogenated ketones and derivatives thereof. The resulting products are phosphorylated keto polyols comprising a tertiary alcohol resulting from the nucleophilic attack of the DHAP to the carbonyl group of the ketone. In certain cases, said phosphorylated keto polyols can spontaneously turn into cyclic hemiketal isomers.

The resulting product of the reaction of DHAP and an activated ketone catalyzed by a class II DHAP aldolase is a phosphorylated keto polyol comprising at least one asymmetric carbon corresponding to the carbon bearing the hydroxy group, at position alpha of the keto group. Without to be bound by any theory, the Inventors are of the opinion that the reaction catalyzed by the RhaD aldolases may be enantioselective, whereby the resulting product is obtained enantiomerically pure or with an enantiomeric excess with respect to this asymmetric carbon. The resulting phosphorylated keto polyols can be dephosphorylated to lead to keto polyols. Said keto polyols can be used as building blocks, in particular as chiral synthons, for the synthesis of a molecule of interest, such as therapeutic ingredients, or as feedstock in fuel and chemical industries. The instant invention thus relates, among others, to a method for preparing phosphorylated keto polyols and their uses in chemical industry as synthons and/or starting material.

Definitions

DHAP aldolase: As used herein, a DHAP aldolase is a lyase able to catalyze in vitro the reversible aldolization reaction between a donor substrate, which is DHAP, and an acceptor substrate which is an aldehyde. Class II DHAP aldolases are metal-dependent aldolases which encompass rhamnulose-1-phosphate aldolase and fuculose-1-phosphate aldolase (natural acceptor substrate: L-Lac for L-lactaldehyde), D-fructose 1,6-bisphosphate aldolase and tagatose-1,6-bisphosphate aldolase (natural acceptor substrate: D-G3P for D-glyceraldehyde 3-phosphate).

RhaD aldolase: As used herein, a RhaD aldolase, also called herein rhamnulose-1-phosphate aldolase, is a class II DHAP aldolase which is able to catalyze in vitro the asymmetric addition of DHAP to (S)-Lac to give L-rhamnulose-1-phosphate (L-R1P):

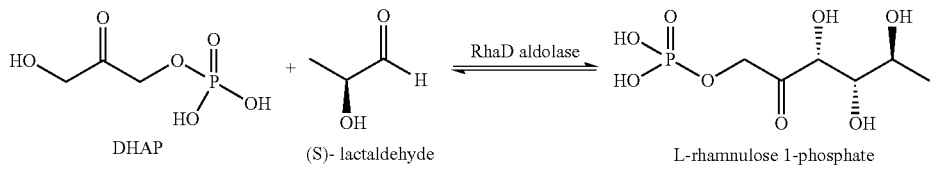

The RhaD aldolase may belong to EC 4.1.2.19 family. Examples of bacterial RhaD aldolases include, without limited to, enzymes of SEQ ID NO: 1-21.

An enzyme having a RhaD activity refers to metal-dependent aldolase able to reversibly catalyze in vitro the asymmetric addition of DHAP to (S)-Lac to give L-rhamnulose-1-phosphate (L-R1P)

Assessment of RhaD aldolase activity: As used herein "RhaD aldolase activity" refers to the ability of a given enzyme to reversibly catalyze in vitro the asymmetric addition of dihydroxyacetone phosphate (DHAP) with (S)-lactaldehyde to give L-R1P.

The reaction preferably takes place in the presence of a divalent metallic cation as cofactor. The divalent metallic cation may be selected among $Mg^{2+}$, $Zn^{2+}$, $Co^{2+}$ and $Mn^{2+}$, preferably $Co^{2+}$.

The ability of an enzyme to display RhaD activity can be assessed in vitro by contacting the enzyme with the substrates, namely DHAP as donor and (S)-lactaldehyde as acceptor in conditions conducive for the enzyme activity and for detecting the formation of the L-R1P. In vitro conditions for assessing the potential RhaD activity of an enzyme may comprise contacting the enzyme and the substrate(s) in the presence of a divalent metallic cation, preferably $Co^{2+}$. RhaD activity may be also assessed in vitro by contacting the enzyme with L-R1P and detecting the release of DHAP (retro-aldol direction). The latter is assayed by adding the glycerolphosphate dehydrogenase (GPDH) and NADH disappearance is monitored, for instance by spectrophotometry as shown below. One unit (U) for RhaD aldolase is defined as the amount of enzyme that converts 1 µmole of the substrate (L-R1P) per min under standard conditions.

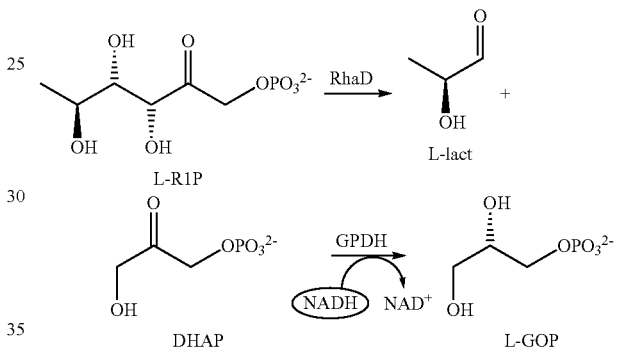

Typically, the enzymatic reaction can be implemented in a buffer at a pH ranging from 6.5 to 8, at a temperature ranging from 15° C. to 30° C.

An appropriate method is disclosed in details in F. Camps Bres, et al. *J. Mol. Catal. B: Enzym.* 2015, 114, 50-57 or in I. Oroz-Guinea et al. *Appl. Microbiol. Biotechnol.* 2015, 99, 3057-3068. For instance, the assessment of the RhAD activity can be implemented in the following conditions:

969 µL GlyGly buffer (50 mM, pH 8)

20 µL NADH (12 mg/mL)

4 µL L-R1P (32 mM)

2 µL glycerolphosphate dehydrogenase, and

5 µL of purified aldolase.

FucA aldolase: As used herein, FucA, also called herein L-fuculose-1-phosphate aldolase, is a class II DHAP aldolase which is able to catalyze in vitro the asymmetric addition of DHAP to L-lactaldehyde to give L-Fuculose-1-phosphate:

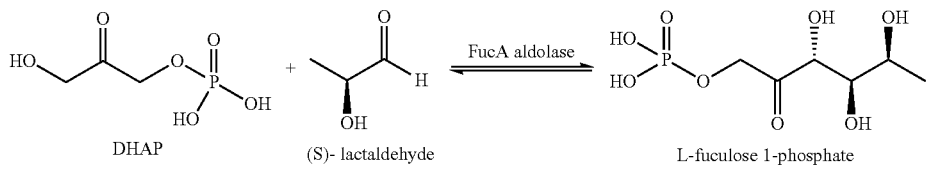

FucAs have the same natural substrates as RhaDs, but lead to a different diastereoisomer even if an high level of similarities between their respective active sites have been described (Higgins et al., J Mol Biol. 2014 Apr. 3; 426(7): 1469-82).

The FucA may belong to EC 4.1.2.17 family. Examples of bacterial FucA aldolases include, without limited to, enzymes of SEQ ID NO:22-23.

An enzyme having a FucA activity refers to a metal-dependent aldolase able to reversibly catalyze in vitro the asymmetric addition of DHAP to (S)-Lac to give L-Fuculose-1-phosphate.

Assessment of FucA aldolase activity: as used herein "FucA aldolase activity" refers to the ability of a given enzyme to reversibly catalyze in vitro the asymmetric addition of dihydroxyacetone phosphate (DHAP) with (S)-Lactaldehyde to give L-fuculose-1-phosphate (L-F1P).

The reaction preferably takes place in the presence of a divalent metallic cation as cofactor. FucA activity may be assessed in vitro as shown above for RhaD activity, except that L-F1P is used instead of L-R1P.

TagA aldolase: As used herein, TagA, also called herein tagatose-1,6-bisphosphate aldolase, is a class II DHAP aldolase which is able to catalyze in vitro the asymmetric addition of DHAP to D-glyceraldehyde 3-phosphate to give D-tagatose-1,6-biphosphate:

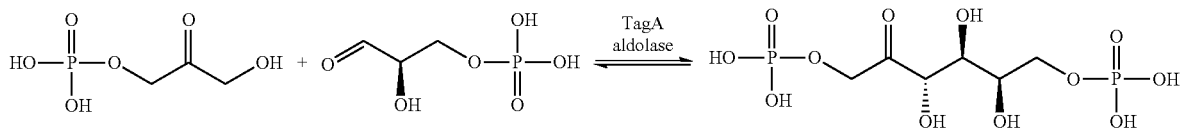

The TagA may belong to EC 4.1.2.40. Examples of bacterial TagA aldolases include, without limited to, enzymes of SEQ ID NO:35.

An enzyme having a TagA activity refers to a metal-dependent aldolase able to reversibly catalyze in vitro the asymmetric addition of DHAP to D-G3P to give D-tagatose-1,6-bisphosphate aldolase.

Assessment of TagA aldolase activity: as used herein "TagA aldolase activity" refers to the ability of a given enzyme to reversibly catalyze in vitro the conversion of D-tagatose-1,6-bisphosphate to DHAP and D-glyceraldehyde 3-phosphate.

The reaction preferably takes place in the presence of a divalent metallic cation as cofactor.

TagA activity may be assessed in vitro as shown above for RhaD activity, except that L-T1,6biP is used instead of L-R1P.

Ketone: as used herein, a ketone refers to a carbonyl-containing compound having the following formula:

$$R^1 \overset{O}{\underset{}{\diagup\!\!\!\diagdown}} R^2$$

in which $R^1$ and $R^2$ are not H.

Thus, "ketones" do not encompass aldehydes, i.e. a compound wherein at least one of $R^1$ and $R^2$ are H.

As used herein, the "ketone" may be a polyketone, namely comprises at least two carbonyl groups of the ketone type. In the context of the invention, the ketone is devoid of any formyl group, namely: —C(═O)—H.

Activated ketone: as used herein, an activated ketone refers to a ketone bearing a group able to increase the reactivity of its carbonyl group with respect to a nucleophile agent, as compared to a similar ketone devoid of said group. As used herein, "activated ketones" encompass 1,3-diketones, 1,2-diketones and ketones bearing an activating group at position alpha of the carbonyl group, preferably an electron withdrawal group (EWG).

In the context of the invention, an activated ketone is a ketone of formula (III)

$$R^1 \overset{O}{\underset{}{\diagup\!\!\!\diagdown}} R^2 \qquad (III)$$

wherein $R^1$ and $R^2$ contain at least one activating group at position alpha of the carbonyl group. $R^1$ and $R^2$ can be of any type. $R^1$ and $R^2$ can be selected from the group consisting of carboxyl, substituted or unsubstituted alkyl, substituted or unsubstituted aryl alkyl, substituted or unsubstituted heteroaryl alkyl, unsubstituted or substituted alkoxycarbonyl, substituted or unsubstituted alkylcarbonyl alkyl, and substituted or unsubstituted alkyl carbonyl. $R^1$ and $R^2$ can also form together a cycle or a heterocycle. Further details about preferred $R^1$ and $R^2$ according to the invention are detailed further below.

The activated ketone preferably comprises one of the following moieties:

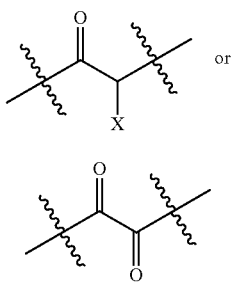
(a)

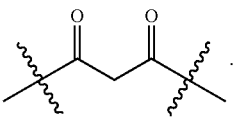
(b)

Wherein X is selected from the group consisting of:
OH, F, Cl, Br, I, —$N_3$, cyano, nitro, —COOH, —$SO_3H$, —$C(F)_3$, —$C(Cl)_3$, —$C(Br)_3$, —$C(I)_3$,
—NHC(=O)R, —NHC(=O)OR, —OR, —SR, —$SO_2R$, —C(=O)R, —C(=O)NHR, —OC(=O)OR—C(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—$N(R^3)_3^+$ wherein each $R^3$ is independently selected from H, $C_1$-$C_{10}$ alkyl and $C_5$-$C_{10}$ aryl,
—OP(=O)($R^4$)$_2$ and —P(=O)($R^4$)$_2$ wherein each $R^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy.

A particular example of moiety (a) is moiety (c):

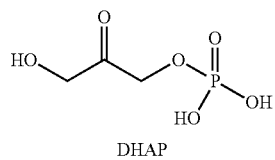
(c)

In such a case, the activated ketone corresponds to a 1,3-diketone.

In the context of the invention, examples of activated ketones of interest encompass 1,2-diketones, 1,3-diketones, α-hydroxy ketones, α-halogeno ketones, α-keto acids, and derivatives thereof.

Keto polyol: as used herein, a keto polyol (also called herein "polyhydroxy ketone") refers to a compound comprising at least one ketone group and at least two hydroxyl groups. In the context of the invention, at least one hydroxyl present in the keto polyol is a tertiary alcohol function. As shown below, in the context of the invention, said tertiary alcohol function results from the nucleophilic attack of the DHAP (which is activated in the form of an enolate in the catalytic site of the RhaD aldolase) on the carbonyl group of the ketone. In some embodiments, the keto polyol may comprise several carbonyl groups, such as 2 carbonyl groups, in particular 2 ketone groups. The keto polyol may be in equilibrium with a cyclic isomer (cyclic hemiketal). Said cyclic hemiketal isomer results from the intramolecular reaction of the ketone group with one of the hydroxyl groups of the keto polyol. As used herein, the term "keto polyol" encompass the keto polyol per se as well as any hemiketal isomers thereof.

For illustration, examples of "keto polyol" are ketoses, cyclic isomers of ketoses, and analogues or derivatives thereof.

Ketose: as used herein, a ketose is a monosaccharide comprising a ketone group. Examples of ketoses encompass ketopentoses such as ribulose and xylulose and ketohexoses such as psicose, fructose, sorbose and tagatose. The term ketose also encompasses hemiketal isomers of the monosaccharide, in particular cyclic hemiketal isomers.

Phosphorylated keto polyol: as used herein, a phosphorylated keto polyol is a keto polyol wherein at least one of the hydroxyl groups is phosphorylated. The term "phosphorylated keto polyol" refers to phosphorylated keto polyol per se and cyclic hemiketal isomers thereof.

In the context of the invention, a preferred phosphorylated keto polyol refers to the product resulting from the reaction of DHAP with an activated ketone of formula $R^1C(=O)R^2$ in the presence of a class II DHAP aldolase, preferably a RhaD aldolase, a FucA aldolase or a TagA aldolase, optionally a RhaD aldolase or a FucA aldolase, more preferably a RhaD aldolase:

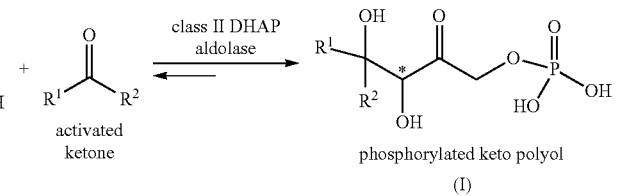

(I)

Noteworthy, said phosphorylated keto polyol generally comprises at least one asymmetric carbon, which bears a tertiary alcohol function.

In the context of the invention, preferred "keto polyols" are those obtained from the dephosphorylation of phosphorylated keto polyol of formula (I), which corresponds to a keto polyol of formula (II):

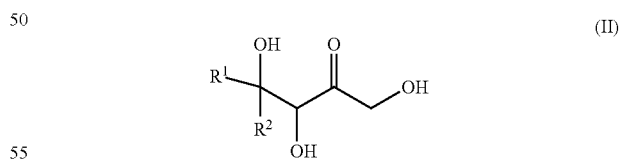
(II)

and cyclic hemiketal isomers thereof.

Alkyl: as used herein, an alkyl refers to any straight or branched chain or cyclic chain hydrocarbon radical wherein carbon-carbon bonds are simple bonds. A $C_1$-$C_6$ alkyl encompasses, without being limited to, methyl, ethyl, propyl, isopropyl, cyclopropyl, butyl, isobutyl, tert-butyl, cyclobutyl, pentyl, cyclopentyl, hexyl, and cyclohexyl. The alkyl group may be substituted or unsubstituted.

Haloalkyl or halogenoalkyl: a haloalkyl refers to an alkyl bearing at least one (e.g. 1, 2, 3 or 4) halogen as substituent. The halogen may be F, Cl, Br and I, preferably F or Cl.

Alkoxy: an "alkoxy" refers to a radical of formula Alk-O— wherein Alk represents an alkyl group.

Aryl: an aryl refers to an aromatic ring system which has 5-14 ring atoms and at least one ring having a conjugated pi electron system. An aryl may contain more than one aromatic ring such as fused ring systems or an aryl group substituted with another aryl group. Aryl encompass, without being limited to, phenyl, anthracyl, naphtyl, and biphenyl. An aryl may be substituted or unsubstituted. A preferred aryl group is phenyl optionally substituted.

Aryloxy: an "aryloxy" refers to a radical of formula Ar—O— wherein Ar represents an aryl group.

Heteroaryl: as used herein, "heteroaryl group" refers to a chemical group having 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Heteroaryl groups include, without being limited to, furanyl, thienyl, pyridyl, pyrrolyl, N-alkyl pyrrolyl, pyridyl-N-oxide, pyrimidyl, pyrazinyl, imidazolyl, benzimidazolyl, benzofuranyl, benzothiophenyl, quinazolinyl, quinolinyl, and the like. The heteroaryl group may be substituted or unsubstituted. A preferred heteroaryl group is pyridyl optionally substituted.

Heteroaryloxy: a "heteroaryloxy" refers to a radical of formula Het-O— wherein Het represents a heteroaryl group.

Aryl alkyl: as used herein, an "aryl alkyl" refers to a radical of formula Ar-Alk- wherein Ar is an aryl group and Alk is an alkyl. An example of aryl alkyl is $Ph-(CH_2)_p-$ wherein Ph is a substituted or unsubstituted phenyl and p is an integer from 1 to 6.

Heteroaryl alkyl: as used herein, a "heteroaryl alkyl" refers to a radical of formula HetAr-Alk- wherein HetAr is a heteroaryl group and Alk is an alkyl.

Alkoxy or aryloxy or heteroaryloxycarbonyl: as used herein, an "alkoxy/aryloxy/heteroalkoxy carbonyl" refers to a radical of formula:

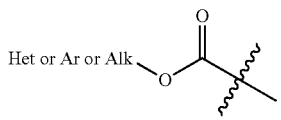

wherein Alk is an alkyl, Het is a heteroaryl and Ar is an aryl.

Alkyl or aryl or heterocarbonyl: as used herein, an "alkyl carbonyl" (also called "alkanoyl") refers to a radical of formula:

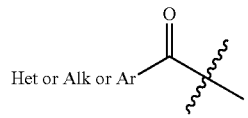

wherein Alk is an alkyl, Het is a heteroaryl and Ar is an aryl.

Alkyl, aryl and Het carbonyl alkyl: As used herein, an "alkyl carbonyl alkyl" is a radical of formula

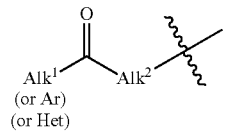

wherein $Alk^1$ and $Alk^2$ are alkyl groups, Ar is an aryl group and Het is an heteroaryl group. As used herein, a "$C_3$-$C_{20}$ alkyl, aryl or heteroaryl carbonyl alkyl" refers to a compound wherein the sum of the backbone carbon atoms in $Alk^2$ and in $Alk^1$, Het, or Ar is from 2 to 19, preferably from 2 to 10. Preferred "alkyl, aryl or heteroaryl carbonyl alkyls" are $Alk^1(C=O)-CH_2-$, $Ar(C=O)-CH_2-$ and $Het(C=O)-CH_2-$.

Substituted: as used herein, a substituted group refers to groups substituted by one or several substituents, typically 1, 2, 3, 4, 5 or 6 substituents. For instance, the substituents may be independently selected from $C_1$-$C_6$ alkyl, aryl group, $C_3$-$C_6$ cycloalkyl, $C_2$-$C_6$ heterocycloalkyl, $C_1$-$C_6$ alkoxy, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, $-N_3$, $-NH_2$, $-F$, $-I$, $-Br$, $-OH$, $-Cl$, $-SH$, $C_1$-$C_6$ alkanoyl, $C_1$-$C_6$ carboxy esters, $C_1$-$C_6$ acylamino, $-COOH$, $-CONH_2$, $-NO_2$, $OP(=O)(OH)_2$, $-SO_3H$, $C_1$-$C_6$ hydroxyalkyl, $C_1$-$C_6$ haloalkyl, $C_1$-$C_6$ alkylthio, $C_2$-$C_{10}$ alkoxy alkyl, $C_2$-$C_6$ alkoxy carbonyloxy, $-CN$, and $-CF_3$. In particular, the substituent(s) may be selected among halogens, in particular F or Cl, $-OH$, $C_1$-$C_6$ alkoxy, $C_1$-$C_6$ alkyl, $C_1$-$C_6$ hydroxyalkyl, and $C_1$-$C_6$ halogenoalkyl.

The wording "optionally substituted" can be replaced by the wording "substituted or unsubstituted" throughout this application.

Expression: the term "expression" includes any step involved in the production of a polypeptide including, but not limited to, transcription, post-transcriptional modification, translation, post-translational modification, and secretion.

Isolated: the term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance).

Recombinant: recombinant refers to a nucleic acid construct, a vector and a protein produced by genetic engineering or to a cell which has been genetically modified with the nucleic construct or the vector, e.g. so as to express a heterologous gene.

Heterologous: in the context of a host cell, a vector or a nucleic acid construct, it designates a coding sequence for the enzyme introduced into the host cell, the vector or the nucleic acid construct by genetic engineering. In the context of an host cell, it can mean that the coding sequence for the enzyme originates from a source different from the cell in which it is introduced. Alternatively, it can also mean that the coding sequence for the enzyme comes from the same species as the cell in which it is introduced but it is considered heterologous due to its environment which is not natural, for example because it is under the control of a promoter which is not its natural promoter, or is introduced at a location which differs from its natural location.

Nucleic acid construct: the term "nucleic acid construct" means a nucleic acid molecule, either single- or double-stranded, which is modified to contain segments of nucleic acids in a manner that would not otherwise exist in nature or which is synthetic, which comprises one or more control sequences.

Operably linked: the term "operably linked" means a configuration in which a control sequence is placed at an appropriate position relative to a coding sequence, in such a way that the control sequence directs expression of the coding sequence.

Amino acid modifications or changes: as used herein, by "amino acid modification" is meant a change in the amino acid sequence of a polypeptide. "Amino acid modifications" which may be also termed "amino acid changes", herein include amino acid mutations such as substitution, insertion, and/or deletion in a polypeptide sequence. By "amino acid substitution" or "substitution" herein is meant the replacement of an amino acid at a particular position in a parent polypeptide sequence with another amino acid. By "amino acid insertion" or "insertion" is meant the addition of an amino acid at a particular position in a parent polypeptide sequence.

By "amino acid deletion" or "deletion" is meant the removal of an amino acid at a particular position in a parent polypeptide sequence.

Parent enzyme or polypeptide: as used herein, it is meant an unmodified enzyme that is subsequently modified to generate a variant.

Variant: as used herein, a variant refers to a polypeptide sequence that differs from that of a parent polypeptide sequence by virtue of at least one amino acid modification. Typically, a variant comprises from 1 to 50 amino acid modifications, preferably from 1 to 40 amino acid modifications. In particular, the variant may have from 1 to 20 amino acid changes, e.g. 1, 2, 3, 4, 5, 6, 7, 8, 9, 10, 11, 12, 13, 14, 15, 16, 17, 18, 19, or 20 amino acid modifications as compared to its parent. The sequence of a variant may comprise one or several amino acid substitutions, and/or, one or several amino acid insertions, and/or one or several amino acid deletions as compared to the sequence of its parent. In some embodiments, the amino acid modifications are conservative, preferably conservative substitutions. In other words, the amino acid modifications present in the variant do not significantly change its properties as compared to its parent. Conservative substitutions and the corresponding rules are well-described in the state of the art. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill (1979, In, The Proteins, Academic Press, New York). Common substitutions are the followings Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly. Alternatively, the amino acid modifications are of such a nature that the physico-chemical properties of the polypeptides are altered. For example, amino acid modifications may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, Science 244: 1081-1085). The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for instance, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide. Single or multiple amino acid substitutions, deletions, and/or insertions can be made and tested using known methods of mutagenesis, recombination, and/or shuffling, followed by a relevant screening procedure. Other methods that can be used include error-prone PCR, phage display, and region-directed mutagenesis.

Sequence identity: the sequence identity between two amino acid sequences is described by the parameter "percentage of identity". For purposes of the present invention, the "percentage of identity" between two amino acid sequences (A) and (B) is determined by comparing the two sequences aligned in an optimal manner, through a window of comparison. Said alignment of sequences can be carried out by well-known methods, for instance, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity may be obtained by dividing the full number of identical amino acid residues aligned by the full number of residues contained in the longest sequence between the sequence (A) and (B). Sequence identity is typically determined using sequence analysis software. For comparing two amino acid sequences, one may use, for example, the tool "Emboss needle" for pairwise sequence alignment of proteins providing by EMBL-EBI and available on www.ebi.ac.uk/Tools/services/web/toolform.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Method for Preparing a Phosphorylated Keto Polyol (Also Called a Polyhydroxy Ketone) to the Invention The invention relates to the use of an enzyme belonging to a class II DHAP aldolase able to catalyze the aldol reaction of DHAP with a ketone. More specifically, the invention relates to the use of an enzyme having RhaD activity, FucA activity or TagA activity, optionally RhaD activity or FucA activity, and able to catalyze the reaction of DHAP with an activated ketone.

The activated ketone is a 1,2-ketone or a ketone comprising an activating group at position alpha of its carbonyl group. The activating group at position alpha may be selected from the group consisting of:

OH, F, Cl, Br, I, azido, cyano, nitro, —COOH, —SO$_3$H, —C(F)$_3$, —C(Cl)$_3$, —C(Br)$_3$, —C(I)$_3$, —NHC(=O)R, —NHC(=O)OR, —OR, —SR, —SO$_2$R, —C(=O)R, —C(=O)NHR, —OC(=O)OR, —C(=O)OR, —C(=O)SR, wherein R is a substituted or unsubstituted C$_1$-C$_{10}$ alkyl, a substituted or unsubstituted C$_5$-C$_{10}$ aryl or a substituted or unsubstituted C$_4$-C$_{10}$ heteroaryl group, —N(R$^3$)$_3$$^+$ wherein each R$^3$ is independently selected from H, C$_1$-C$_{10}$ alkyl and C$_5$-C$_{10}$ aryl, OP(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy.

Thus, examples of activated ketones of interest encompass, without being limited to, 1,2-diketones, 1,3-diketones, α-hydroxy ketones, α-halogeno ketones, α-keto acids, and derivatives thereof.

The product of the reaction catalyzed by the enzyme is a phosphorylated keto polyol. The phosphorylated keto polyol comprises a tertiary alcohol function which results from the nucleophilic attack of the DHAP (activated as an enolate in the catalytic site of the enzyme) on a carbonyl group of the ketone.

In a certain aspect, the invention relates to a method for preparing a phosphorylated keto polyol of formula (I):

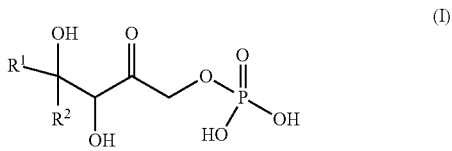
(I)

or a cyclic hemiketal isomer thereof.
said method comprises a step of reacting dihydroxyacetone phosphate (DHAP) with a ketone of formula (III)

(III)

in the presence of an enzyme having a class II DHAP activity, preferably a RhaD activity, a FucA activity or a TagA activity, optionally a RhaD activity or a FucA activity, more preferably a RhaD activity,
wherein $R^1$ and $R^2$ are such that:
The molecular weight of the ketone of formula (III) is less than 600 g·mol$^{-1}$,
neither $R^1$ nor $R^2$ are H, and
the ketone of in formula (III) comprises at least one a moiety selected from:

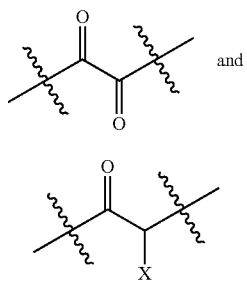

(b)

and (a)

wherein X is selected from the group consisting of:
OH, F, Cl, Br, I, —$N_3$, cyano, nitro, —COOH, —$SO_3H$, —C(F)$_3$, —C(Cl)$_3$, —C(Br)$_3$, —C(I)$_3$,
—NHC(=O)R, —NHC(=O)OR, —OR, —SR, —SO$_2$R, —C(=O)R, —C(=O)OR, —C(=O)NHR, —OC(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—N(R$^3$)$_3^+$ wherein each R$^3$ is independently selected from H, $C_1$-$C_{10}$ alkyl and $C_5$-$C_{10}$ aryl,
OP(=O)(R$^4$)$_2$ and P(=O)(R$^4$)$_2$ wherein each R$^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy.

In the context of the invention, the carbonyl group shown in formula (III) corresponds to the activated carbonyl which reacts with DHAP to give the compound of formula (I). As fully described herein, said carbonyl group shown in formula (III) is included in a 1,2-diketone moiety or has an activating group at position alpha, preferably an electron withdrawal group (EWG).

The Ketone of Formula (III)

As mentioned above, the enzyme with the class II DHAP activity is able to catalyze the reaction of DHAP with a ketone of formula (III)

(III)

wherein $R_2$ and $R_1$ are such that:
at least one oxo group is present at position alpha of the carbonyl group (e.g. the activated ketone is a 1,2 diketone), and/or
at least one activating group is present at position alpha of the carbonyl group, said activating group being, for instance, an electron withdrawal group. Preferably, the at least one activating group is selected from the group consisting of:
OH, F, Cl, Br, I, —$N_3$, cyano, nitro, —COOH, —$SO_3H$, —C(F)$_3$, —C(Cl)$_3$, —C(Br)$_3$, —C(I)$_3$,
NHC(=O)R, —NHC(=O)OR, —OR, —SR, —SO$_2$R, —C(=O)R, —C(=O)NHR, —OC(=O) OR, —C(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—N(R$^3$)$_3^+$ wherein each R$^3$ is independently selected from H, $C_1$-$C_{10}$ alkyl and $C_5$-$C_{10}$ aryl,
OP(=O)(R$^4$)$_2$ and P(=O)(R$^4$)$_2$ wherein each R$^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy,
R, R$^3$ and R$^4$ groups may comprise one or several substituents (e.g. 1, 2, 3 or 4 substituents). Said possible substituent(s) present in the R, R$^3$ and R$^4$ groups may be of any type as described above in the section entitled "Definitions". For instance, said possible substituents may be independently selected from NH$_2$, OH, F, Cl, Br, I, —$N_3$, cyano, nitro, SH, —CONH$_2$, —COOH, —$SO_3H$, —C(F)$_3$, $C_1$-$C_6$ alkyl, $C_1$-$C_6$ alkoxy, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, OP(=O)(OH)$_2$, —$SO_3H$, $C_1$-$C_6$ hydroxyalkyl, $C_1$-$C_6$ haloalkyl, $C_1$-$C_6$ alkylthio, $C_1$-$C_6$ thioalkyl, $C_2$-$C_{10}$ alkoxy alkyl, and $C_2$-$C_6$ alkoxy carbonyloxy. In particular, the substituent(s) may be selected among halogens, in particular F or Cl, —OH, $C_1$-$C_6$ alkoxy, $C_1$-$C_6$ alkyl, $C_1$-$C_6$ hydroxyalkyl, and $C_1$-$C_6$ halogeno alkyl.

It goes without saying that neither $R_1$ or $R_2$ are H.

In some embodiments, $R^1$ and $R^2$ are such that the ketone of formula (III) comprises a moiety of formula (b):

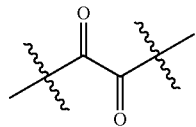

(b)

In some other embodiments, $R^1$ and $R^2$ are such that the ketone of formula (III) comprises a moiety of formula (a):

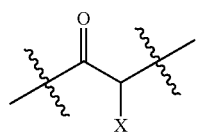

(a)

Wherein X is selected from the group consisting of:
OH, F, Cl, Br, I, —$N_3$, cyano, nitro, —COOH, —$SO_3H$, —$C(F)_3$, —$C(Cl)_3$, —$C(Br)_3$, —$C(I)_3$,
NHC(=O)R, —NHC(=O)OR, —OR, —SR, —$SO_2R$, —C(=O)R, —C(=O)OR, —C(=O)NHR, —OC(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—$N(R^3)_3^+$ wherein each $R^3$ is independently selected from H, $C_1$-$C_{10}$ alkyl and $C_5$-$C_{10}$ aryl,
OP(=O)($R^4$)$_2$ and P(=O)($R^4$)$_2$ wherein each $R^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy.

R, $R^3$ and $R^4$ groups may comprise one or several substituents (e.g. 1, 2, 3 or 4 substituents) as described above. Said possible substituent(s) present in the R, $R^3$ and $R^4$ groups may be of any type as described above. For instance, the substituent(s) may be selected among halogens, —OH, $C_1$-$C_6$ alkoxy, $C_1$-$C_6$ alkyl, $C_1$-$C_6$ hydroxyalkyl, and $C_1$-$C_6$ halogeno alkyl.

It goes without saying that the carbonyl group shown in formula (III) is included in the moiety of formula (a) or (b) and that the compound of formula (I) results from the reaction of said carbonyl group with DHAP in the presence of the enzyme.

In some embodiments, $R^1$ and $R^2$ are such that the ketone of formula (III) comprises a moiety of formula (a):

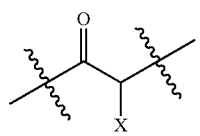

(a)

wherein X is selected from the group consisting of OH, F, Cl, Br, I, —$N_3$, cyano, nitro, —COOH, —$SO_3H$, —$C(F)_3$, —$C(Cl)_3$, —$C(Br)_3$, —$C(I)_3$, —NHC(=O)R, —NHC(=O)OR, —OR, —SR, —C(=O)R, —C(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group.

For instance, X may be selected from of OH, F, Cl, Br, I, —$N_3$, cyano, nitro, —$SO_3H$, —$C(F)_3$, —COOH, —OR, —C(=O)R, and —C(=O)OR, wherein R is a $C_1$-$C_{10}$, e.g. $C_1$-$C_6$ alkyl optionally substituted by at least one (for instance at least 2, 3, or 4) groups selected from OH, $C_1$-$C_3$ alkyl, halogen, $C_1$-$C_3$ alkoxy, $C_1$-$C_3$ hydroxyalkyl, and $C_1$-$C_3$ halogenoalkyl.

As a further example, X may be —C(=O)R with R as described above, whereby the ketone comprising the following moiety (c):

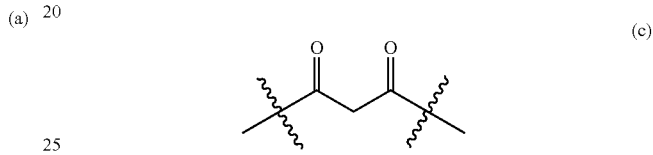

(c)

In other words, the activated ketone may be a 1,3-diketone.

$R^1$ and $R^2$ may be of any type with proviso that the ketone of formula (III) comprises one of the moieties (a), and (b) as shown above. Typically, $R^1$ and $R^2$ are such that the molecular weight of the ketone of formula (III) is less than 700 g·mol$^{-1}$, for instance less than 600, 500, 400, 350, 300, 250 or 200 g·mol$^{-1}$. Typically $R^1$ and $R^2$ may each comprise from 1 to 20 carbon atoms, for instance from 1 to 15 carbon atoms or from 1 to 10 carbon atoms such that 1, 2, 3, 4, 5, 6, 7, 8 or 9 carbon atoms.

$R^1$ and $R^2$ may be separate groups or may form together a ring. The ketone of formula (III) may thus be cyclic or acyclic. $R^1$ and $R^2$ may be independently aliphatic groups or may comprise an aromatic moiety, for instance an aryl or an heteroaryl moiety. $R^1$ and $R^2$ may further comprise one or several heteroatoms in their backbone and may bear one or several substituents, which may also contain one or several heteroatoms. Said substituents may be selected from the groups as defined for the X group above, as well as among groups such that $NH_2$, SH, —$CONH_2$, $C_1$-$C_6$ alkyl, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, $C_1$-$C_6$ hydroxyalkyl, $C_1$-$C_6$ haloalkyl, and $C_1$-$C_6$ thioalkyl. The backbone of $R^1$ and $R^2$ may be saturated, or may be unsaturated, namely having one or several double or triple bonds.

In some embodiments, $R^1$ and $R^2$ may be independently selected from the group consisting of —$(CH_2)_s$—COOH with s an integer from 0 to 3, substituted or unsubstituted $C_1$-$C_{10}$ alkyl, substituted or unsubstituted $C_6$-$C_{10}$ aryl alkyl, substituted or unsubstituted $C_6$-$C_{10}$ heteroaryl alkyl, unsubstituted or substituted $C_2$-$C_{10}$ alkoxycarbonyl, substituted or unsubstituted $C_3$-$C_{10}$ alkylcarbonyl alkyl, and substituted or unsubstituted $C_2$-$C_{10}$ alkyl carbonyl. The substituent(s) present in $R^1$ and/or $R^2$ may be independently selected from the groups as defined for the X group above as well as among $NH_2$, SH, —$CONH_2$, $C_1$-$C_6$ alkyl, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, $C_1$-$C_6$ hydroxyalkyl, $C_1$-$C_6$ haloalkyl, and $C_1$-$C_6$ thioalkyl.

The optionally substituted $C_6$-$C_{10}$ aryl alkyl may be of formula Ar—$(CH_2)_r$— with r is an integer from 1 to 6, preferably 1, 2 or 3, and Ar an aryl, for instance a phenyl which is optionally substituted. The optionally substituted heteroaryl alkyl may be of formula HetAr—$(CH_2)_r$— with r is an integer from 1 to 6, preferably 1, 2 or 3, and HetAr is an heteroaryle, for instance, a pyridyl which is optionally substituted.

Alternatively, $R^1$ and $R^2$ can form together, with the carbonyl group, a $C_4$-$C_8$ ring bearing a second oxo group at position alpha of the carbonyl and/or substituted at position alpha of the carbonyl by a group selected from:

OH, F, Cl, Br, I, —$N_3$, cyano, nitro, —COOH, —$SO_3H$, —$C(F)_3$, —$C(Cl)_3$, —$C(Br)_3$, —$C(I)_3$,
—NHC(=O)R, —NHC(=O)OR, —OR, —SR, —$SO_2R$, —C(=O)R, —C(=O)OR, —C(=O)NHR, —OC(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—$N(R^3)_3^+$ wherein each $R^3$ is independently selected from H, $C_1$-$C_{10}$ alkyl and $C_5$-$C_{10}$ aryl,
OP(=O)$(R^4)_2$ and P(=O)$(R^4)_2$ wherein each $R^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy.

R, $R^3$ and $R^4$ groups may comprise one or several substituents (e.g. 1, 2, or 3 substituents) as described above. Said possible substituent(s) present in the R, $R^3$ and $R^4$ groups may be of any type as described above. For instance, the substituent(s) may be selected among halogens, in —OH, $C_1$-$C_6$ alkoxy, $C_1$-$C_6$ alkyl, $C_1$-$C_6$ hydroxyalkyl, and $C_1$-$C_6$ halogeno alkyl.

The $C_4$-$C_8$ ring may comprise one or several ring heteroatoms selected from O, N and S. The $C_4$-$C_8$ may also bear one or several (e.g. 1, 2 or 3) additional substituents, which may be selected from OH, $C_1$-$C_3$ alkyl, halogen, $C_1$-$C_3$ alkoxy, $C_1$-$C_3$ hydroxyalkyl, and $C_1$-$C_3$ halogenoalkyl. For illustration only, the ketone of formula (III) may be a substituted cyclohexanone such as a 2-hydroxycyclohexanone, a substituted cyclopentanone such as a 2-hydroxycyclopentanone, a substituted or unsubstituted 1,3-cyclohexanedione, a substituted or unsubstituted 1,2-cyclohexanedione.

In some embodiments, the ketone of formula (III) is such that:

$R^1$ and $R^2$ are independently selected from the group consisting of —$(CH_2)_p$-Ph, —COOH, —C(=O)—R, —$CH_2$—C(=O)—R, —C(=O)OR, and $C_1$-$C_{10}$, preferably $C_1$-$C_6$ alkyl optionally substituted with at least one group (e.g. at least 2, 3, 4 or 5) selected from —OH, $C_1$-$C_3$ alkoxy, $C_1$-$C_3$ alkyl, —F, —Cl, —Br, —I, wherein:
Ph is a phenyl optionally substituted by one or several substituents preferably selected from halogens, —OH, $C_1$-$C_6$ alkyl, and $C_1$-$C_6$ alkoxy
p is an integer from 1 to 6, preferably 1, 2 or 3, and
R is a $C_1$-$C_6$ alkyl optionally substituted by one or several substituents preferably selected from halogens, —OH, $C_1$-$C_3$ alkyl, and $C_1$-$C_3$ alkoxy.

$R^1$ and $R^2$ form together, with the carbonyl group, a $C_5$-$C_6$ ring bearing at least one group selected from —OH, —$OCH_3$, —F, —Cl, —Br, —I, at position alpha of the carbonyl group or a second oxo group at position alpha or beta of the carbonyl group.

In another embodiment, the ketone of formula (III) is such that:
$R^1$ and $R^2$ are independently selected from the group consisting of —$(CH_2)_p$-Ph, wherein Ph is a phenyl, and p is 1 or 2; COOH; —$CH_2$—C(=O)—R, —C(=O)—R wherein R is a $C_1$-$C_3$ alkyl; unsubstituted $C_1$-$C_6$, preferably $C_1$-$C_3$ alkyl, and $C_1$-$C_6$, preferably $C_1$-$C_3$ alkyl substituted with at least one (e.g. at least 2, 3 or 4) group selected from —OH, —$OCH_3$ and —Cl, such as —$CH_2OH$, —CH(OH)—$CH_3$ or —CH(OH)—$CH_2OH$;
or
$R^1$ and $R^2$ form together, with the carbonyl group, a $C_6$ ring bearing at least one group selected from —OH, —$OCH_3$, and —Cl at position alpha of the carbonyl group or bearing a second oxo group at position alpha or beta of the carbonyl group.

It goes without saying that, in all the above embodiments, $R^1$ and $R^2$ are selected so that the ketone of formula (III) comprises a moiety selected from moiety (a), and (b) as described above. Moreover, $R^1$ and $R^2$ in the resulting phosphorylated keto polyol of formula (I) correspond to the $R^1$ and $R^2$ in the starting ketone of formula (III).

In some embodiments of the method or the use according to the invention, the ketone is selected from the group consisting of 1,2-diketones, 1,3-diketones, α-hydroxy ketones, α-halogeno ketones, α-keto acids, and derivatives thereof.

In a particular embodiment of the invention, the ketone comprises the moiety (a), whereby the resulting phosphorylated keto polyol comprises the moiety (a'):

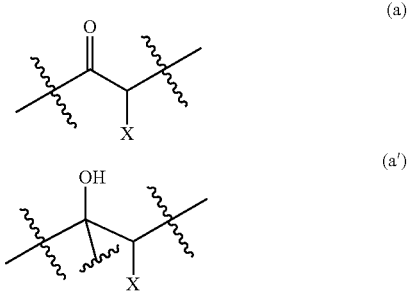

In some embodiments, the ketone is of formula (IIIa):

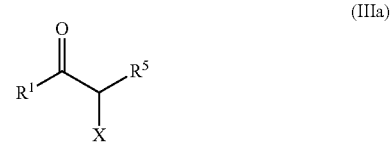

Wherein X is selected from the group consisting of:
OH, F, Cl, Br, I, —$N_3$, cyano, nitro, —COOH, —$SO_3H$, —$C(F)_3$, —$C(Cl)_3$, —$C(Br)_3$, —$C(I)_3$,
—NHC(=O)R, —NHC(=O)OR, —OR, —SR, —$SO_2R$, —C(=O)R, —C(=O)OR, C(=O)NHR, —OC(=O)OR, —C(=O)SR, wherein R is a substituted or unsubstituted $C_1$-$C_{10}$ alkyl, a substituted or unsubstituted $C_5$-$C_{10}$ aryl or a substituted or unsubstituted $C_4$-$C_{10}$ heteroaryl group,
—$N(R^3)_3^+$ wherein each $R^3$ is independently selected from H, $C_1$-$C_{10}$ alkyl and $C_5$-$C_{10}$ aryl, and $OP(=O)(R^4)_2$ and $P(=O)(R^4)_2$ wherein each $R^4$ is independently selected from H, a substituted or unsubstituted $C_1$-$C_{10}$ alkyl, a substituted or unsubstituted $C_5$-$C_{10}$ aryl, a substituted or unsubstituted $C_4$-$C_{10}$ heteroaryl group, substituted or unsubstituted $C_1$-$C_{10}$ alkoxy and substituted or unsubstituted $C_5$-$C_{10}$ aryloxy. Preferably X is selected from —OH, —$OCH_3$, —C(=O)$CH_3$ and Cl.

$R^1$ and $R^5$ are such that:
- $R^1$ and $R^5$ form together, with the moiety (a), a $C_5$-$C_6$ ring optionally bearing at least one (e.g. 1, 2 or 3) additional substituent, said additional substituent being preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, $OP(=O)(OH)_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl.

or

- $R^1$ and $R^5$ are independently selected from the group consisting of H, —OH, —$(CH_2)_p$-Ph, unsubstituted $C_1$-$C_6$ alkyl, and substituted $C_1$-$C_6$ alkyl wherein:
  - $R^1$ is not H,
  - p is an integer from 1 to 6, preferably 1, 2 or 3,
  - Ph is a phenyl group optionally substituted by one or several (e.g. 1, 2 or 3) groups preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, $OP(=O)(OH)_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl,
  - The substituted $C_1$-$C_6$ alkyl comprises at least one (e.g 1, 2, 3, 4, 5, or 6) substituent preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, $OP(=O)(OH)_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl.

In a particular embodiment, the ketone is a compound of formula (IIIa) wherein:
- X is selected from —OH, —$OCH_3$, a halogen preferably Cl or F, and C(=O)$CH_3$,
- $R^1$ and $R^5$ are independently selected from H, $C_1$-$C_6$ alkyl, $C_1$-$C_6$ alkyl substituted by 1 to 6 (e.g. 1, 2, 3 or 4) substituents selected from $C_1$-$C_3$ alkoxy, $C_1$-$C_3$ haloalkyl, F, Cl, Br, I and OH; and —$CH_2$-Ph optionally bearing at least one (e.g. 1, 2 or 3) substituent selected from F, Cl, Br, I, —OH, $C_1$-$C_3$ alkyl, $C_1$-$C_3$ haloalkyl, and $C_1$-$C_3$ alkoxy;
  - with proviso that $R_1$ is not H, or
- $R^1$ and $R^5$ form together with the moiety (a), a $C_5$-$C_6$ ring optionally bearing at least one additional substituent selected from —OH, $C_1$-$C_3$ alkyl, $C_1$-$C_3$ haloalkyl, F, Cl, Br, I and $C_1$-$C_3$ alkoxy.

For instance, the ketone may be a compound of formula (IIIa) wherein:
- X is —OH, —$OCH_3$, Cl, or C(=O)$CH_3$ and
- $R^1$ and $R^5$ are independently selected from H, —$CH_2$-Ph with Ph is a phenyl group, $C_1$-$C_3$ alkyl such as methyl, ethyl or propyl, $C_1$-$C_6$ alkyl substituted by one or several (e.g. 1,2 or 3) —OH or —$OCH_3$ such as —$(CH_2)_2OH$, —CH(OH)—$CH_2OH$, and —$CH_2OH$;
  - with proviso that $R_1$ is not H, or
- $R^1$ and $R^5$ form together, with the moiety (a), a $C_5$-$C_6$ ring.

As another example, the ketone may be a compound of formula (IIIa) wherein:
- X is —OH, —$OCH_3$, Cl, or C(=O)$CH_3$
- $R^1$ is selected from —$CH_2$-Ph with Ph is a phenyl group, $C_1$-$C_3$ alkyl such as methyl, ethyl or propyl, $C_1$-$C_6$ alkyl substituted by one or several (e.g. 1,2 or 3) —OH or —$OCH_3$ such as —$(CH_2)_2OH$, —CH(OH)—$CH_2OH$, and —$CH_2OH$; and $R^5$ is selected from H, $C_1$-$C_3$ alkyl such as methyl, ethyl or propyl, $C_1$-$C_6$ alkyl substituted by one or several (e.g. 1, 2 or 3) —OH or —$OCH_3$ such as —$(CH_2)_2OH$, —CH(OH)—$CH_2OH$, and —$CH_2OH$, or
- $R^1$ and $R^5$ form together, with the moiety (a), a $C_5$-$C_6$ ring.

The phosphorylated keto polyol obtained by the method of the invention from a ketone of formula (IIIa) is of formula (Ia):

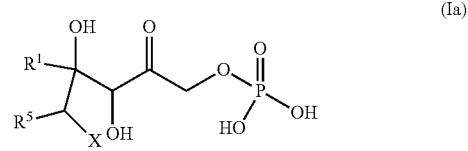

(Ia)

or cyclic hemiketal isomers thereof,
wherein $R^1$, $R^5$ and X are as defined in Formula (IIIa).

It goes without saying $R^1$, $R^5$ and X in the resulting phosphorylated keto polyol of formula (Ia) correspond to the $R^1$, $R^5$ and X present in the starting ketone of formula (IIIa).

Examples of ketones of formula (IIIa) and the corresponding phosphorylated keto polyols of formula (Ia) are shown in the below table 1:

TABLE 1

Examples of ketones of formula (IIIa) and corresponding phosphorylated keto polyols.

| Ketone of formula (IIIa) | Corresponding phosphorylated keto polyol of formula (Ia) in non-cyclic form |
|---|---|
| 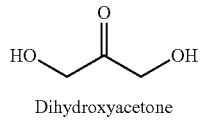 Dihydroxyacetone | 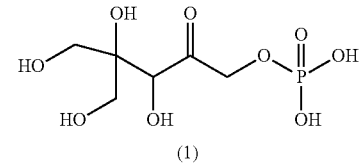 (1) |

TABLE 1-continued

Examples of ketones of formula (IIIa) and corresponding phosphorylated keto polyols.

| Ketone of formula (IIIa) | Corresponding phosphorylated keto polyol of formula (Ia) in non-cyclic form |
|---|---|
| 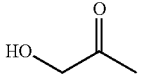<br>Hydroxyacetone | 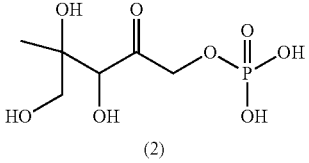<br>(2) |
| 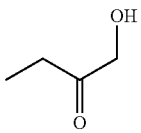<br>1-Hydroxybutan-2-one | 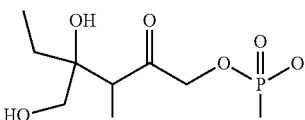<br>(3) |
| 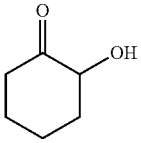<br>2-hydroxycyclohexanone | 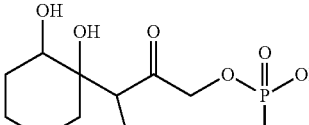<br>(4) |
| 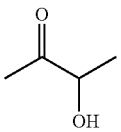<br>Acetoïne | 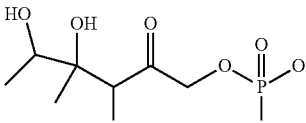<br>(5) |
| 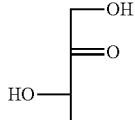<br>L-Erythrulose | 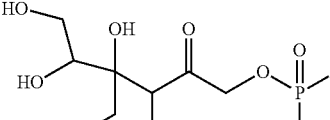<br>(6) |
| 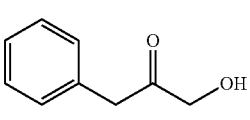<br>1-Hydroxy-3-phenylpropan-2-one | 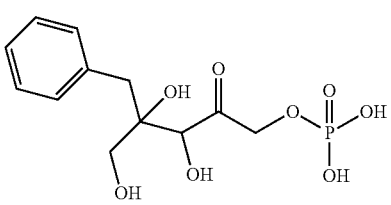<br>(7) |
| 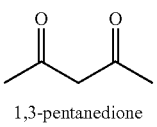<br>1,3-pentanedione | 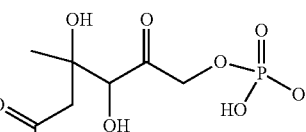<br>(8) |

TABLE 1-continued

Examples of ketones of formula (IIIa) and corresponding phosphorylated keto polyols.

| Ketone of formula (IIIa) | Corresponding phosphorylated keto polyol of formula (Ia) in non-cyclic form |
|---|---|
| 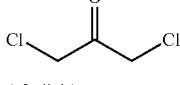 1,3-dichloropropanone | 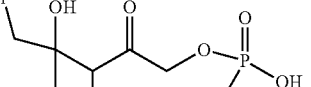 (9) |

As mentioned above, certain phosphorylated keto polyols can isomerize into cyclic hemiketal isomers, which are also included in the scope of the present invention.

In another embodiment, the ketone comprises the moiety (b). The phosphorylated keto polyol thus comprises the moiety of formula (b')

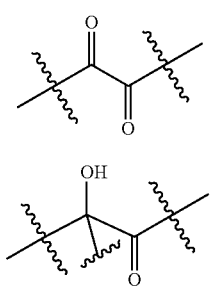

Accordingly, the ketone is of formula of:

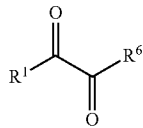

(IIIb)

wherein
  $R^1$ and $R^6$ are independently selected from the group consisting of —OH, $C_1$-$C_6$ alkyloxy, —$(CH_2)_p$-Ph, unsubstituted $C_1$-$C_6$ alkyl, and substituted $C_1$-$C_6$ alkyl wherein:
    p is an integer from 1 to 6, preferably 1, 2 or 3,
    Ph is a phenyl group optionally substituted by one or several (e.g. 2 or 3) substituents preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, OP(=O)(OH)$_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl,
    The substituted $C_1$-$C_6$ alkyl comprises at least one (e.g 1, 2, 3, 4, 5, or 6) substituents preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, OP(=O)(OH)$_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl; or $R^1$ and $R^6$ forms, together with the moiety (b), a $C_5$-$C_6$ ring optionally bearing an additional substituent preferably selected from $NH_2$, OH, F, Cl, Br, I, —$N_3$, cyano, nitro, SH, —$CONH_2$, —COOH, —$SO_3H$, —$C(F)_3$, $C_1$-$C_3$ alkyl, $C_1$-$C_3$ alkoxy, $C_1$-$C_3$ alkylamino, $C_1$-$C_3$ aminoalkyl, $C_1$-$C_3$ N,N-dialkylamino alkyl, $C_1$-$C_3$ N-alkylamino alkyl, OP(=O)(OH)$_2$, —$SO_3H$, $C_1$-$C_3$ hydroxyalkyl, $C_1$-$C_3$ haloalkyl, $C_1$-$C_3$ alkylthio, and $C_1$-$C_3$ thioalkyl.

Preferably $R^1$ and $R^6$ are not together —OR or —OH.

In a particular embodiment, $R^1$ is selected from $C_1$-$C_6$ alkyl such as ethyl or methyl, and $C_1$-$C_6$ alkyl substituted with at least one (for instance 1, 2, 3, 4, 5 or 6) hydroxyl or methoxy group and $R^6$ is selected from —OH, $C_1$-$C_6$ alkoxy such as methoxy, and $C_1$-$C_6$ alkyl such as methyl or ethyl.

The phosphorylated keto polyol obtained by the method of the invention from a ketone of formula (IIIb) is of formula (Ib):

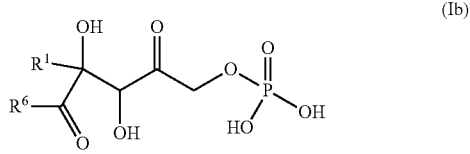

or cyclic hemiketal isomers thereof wherein $R^1$ and $R^6$ are as defined above for ketone of formula (IIIb)

It goes without saying $R^1$ and $R^6$ in the resulting phosphorylated keto polyol of formula (Ic) correspond to the $R^1$ and $R^6$ present in the starting ketone of formula (IIIb).

Examples of ketone of formula (IIIb) and the corresponding phosphorylated keto polyol of formula (Ib) are shown in the below table 2:

TABLE 2

Examples of ketones of formula (IIIb) and corresponding phosphorylated keto polyol

| Ketone of formula (IIIb) | Corresponding phosphorylated keto polyol of formula (Ib) in non-cyclic form |
|---|---|
| HPA | (10) |
| Pyruvic acid | (11) |
| 2,3-butanedione | (12) |

The ketone may be added in the reaction medium in the form of a hemiketal or a dimer thereof as in the case of dihydroxyacetone which may be added as a cyclic dimer.

The Resulting Phosphorylated Keto Polyol of Formula (I)

$R^1$ and $R^2$ in the phosphorylated keto polyol are the same as $R^1$ and $R^2$ groups in the starting ketone of formula (III). In some embodiments, the phosphorylated keto polyol is a compound of formula (Ia) and (Ib) or a cyclic hemiketal isomer thereof, as described above.

The phosphorylated keto polyol may spontaneously isomerize into a hemiketal cyclic isomer. Such isomer results from the intramolecular reaction between a hydroxyl group and a carbonyl group of the compound. The resulting cyclic isomer generally comprises a tetrahydrofuran or a tetrahydropyran ring.

The phosphorylated keto polyol comprises at least one asymmetric carbon (corresponding to the carbon atoms bearing OH at position alpha of the carbonyl in formula (I)), whereby the compound exists in two enantiomers or several diastereoisomers if the molecule comprises at least one additional asymmetric carbon. Without to be bound by any theory, the Inventors believe that the method of the invention is enantio- or diastereo-selective, which means that one enantiomer or one diastereomer of the phosphorylated keto polyol is formed in preference to another. In some embodiments, said diastereomer or said enantiomer represents more than 50%, preferably more than 60%, 70%, 80%, 90%, 95% or 98% by mole of the resulting phosphorylated keto polyol, the percentage referring to the total molar amount of phosphorylated keto polyol formed by reaction of DHAP with the ketone according to the invention.

The Enzyme Used According to the Invention

The enzyme used in the method of the invention may be a class II DHAP aldolase, preferably a class II DHAP aldolase having a RhaD activity, a FucA activity or a TagA activity, optionally a RhaD activity or a FucA activity.

In some embodiments, the enzyme has a FucA activity. Said enzyme may be any metal-dependent aldolase of class II able to catalyze in vitro the reaction of dihydroxyacetone phosphate (DHAP) with (S)-lactaldehyde to give L-fuculose-1-P, under conditions appropriate to observe the enzymatic reaction, for instance as described in the above "definitions" section. Enzymes having FucA activity are well-known in the prior art and preferably belong to E.C. 4.1.2.17. The skilled artisan may carry out the method of the invention with any enzyme belonging to EC 4.1.2.17 or identified as belonging to said class.

Appropriate enzymes with a FucA activity may be also identified from microorganisms having a FucA activity, such as bacteria and fungi. The enzyme may be identified and obtained from microorganisms isolated from nature (e.g., soil, composts, water, etc.). Alternatively, the enzyme may be obtained by screening a genomic DNA, cDNA library from microorganisms, a mixed DNA sample or DNA samples obtained directly from natural materials (e.g., soil, composts, water, etc.).

In some embodiments, the enzyme has a FucA activity and comprising a polypeptide having at least 30, 35, 40, 45, 50, 55 or 60% of sequence identity with an amino acid sequence selected from SEQ ID NO:22, SEQ ID NO:23 and SEQ ID NO:26-SEQ ID NO:34, preferably with an amino acid sequence selected from SEQ ID NO:22, SEQ ID NO:23 and SEQ ID NO:26, optionally with an amino acid sequence of SEQ ID NO:22 or of SEQ ID NO:23.

In another embodiment, the enzyme has a RhaD activity. The enzyme having a RhaD activity is used as a catalyst in the reaction of DHAP with the ketone of formula (III). Said enzyme may be any metal-dependent aldolase of class II able to catalyze in vitro the reaction of dihydroxyacetone phosphate (DHAP) with (S)-lactaldehyde to give L-R1P, under conditions appropriate to observe the enzymatic reaction, for instance as described in the above "definitions" section.

Enzymes having RhaD activity are well-known in the prior art and preferably belong to E.C. 4.1.2.19. The skilled artisan may carry out the method of the invention with any enzyme belonging to EC 4.1.2.19. Examples of RhaD are for instance described in P. Clapés, X. Garrabou, Adv. Synth. Catal. 2011, 353, 2263-2283 the disclosure of which being incorporated herein by reference. Appropriate enzymes with a RhaD activity may be also identified from microorganisms having a RhaD activity, such as bacteria and fungi. The enzyme may be identified and obtained from microorganisms isolated from nature (e.g., soil, composts, water, etc.). Alternatively, the enzyme may be obtained by screening a genomic DNA, cDNA library from microorganisms, a mixed DNA sample or DNA samples obtained directly from natural materials (e.g., soil, composts, water, etc.).

In some embodiments, the enzyme of the invention is an enzyme having a RhaD activity and comprising a polypeptide having at least 30, 35, 40, 45, 50, 55 or 60% of sequence identity with an amino sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO17, SEQ ID NO:18, SEQ ID NO:19, SEQ ID NO:20 SEQ ID NO:21.

In some embodiments, the enzyme has a TagA activity. Said enzyme may be any metal-dependent aldolase of class II able to catalyze in vitro the cleavage of D-tagatose-1,6-bisphosphate to give dihydroxyacetone phosphate (DHAP) DHAP and D-glyceraldehyde 3-phosphate, under conditions appropriate to observe the enzymatic reaction, for instance as described in the above "definitions" section. Enzymes having TagA activity are well-known in the prior art and preferably belong to E.C. 4.1.2.40. The skilled artisan may carry out the method of the invention with any enzyme belonging to EC 4.1.2.40 or identified as belonging to said class.

Appropriate enzymes with a TagA activity may be also identified from microorganisms having a TagA activity, such as bacteria and fungi. The enzyme may be identified and obtained from microorganisms isolated from nature (e.g., soil, composts, water, etc.). Alternatively, the enzyme may be obtained by screening a genomic DNA, cDNA library from microorganisms, a mixed DNA sample or DNA samples obtained directly from natural materials (e.g., soil, composts, water, etc.).

In some embodiments, the enzyme has a TagA activity and comprising a polypeptide having at least 50, 55 or 60% of sequence identity with an amino acid sequence selected from SEQ ID NO:35.

"At least 60% of sequence identity" encompasses a percentage of sequence identity of at least 65%, 70%, 75%, 80%, 85%, 90%, 95%, 96%, 97%, 98% and 99%. "At least 30% of sequence identity" encompasses a percentage of sequence identity of at least 35%, 40%, 45%, 50%, 55%, 60%, 65%, 70%, 75%, 80%, 85%, 90%, 95%, 96%, 97%, 98% and 99%.

In some embodiments, the enzyme has a RhaD activity and comprises a polypeptide having at least 60%, preferably at least 70%, 80%, 85%, 90% or 95%, of sequence identity with SEQ ID NO:10.

The enzyme having a class II DHAP activity, for instance a RhaD activity, a FucA activity or a TagA activity, optionally a RhaD activity or a FucA activity, may be a wild-type isolated enzyme, namely an isolated naturally-occurring enzyme, a variant of a wild-type enzyme, or a hybrid polypeptide.

In some embodiments, the enzyme of the invention is a wild-type enzyme originating from a microorganism such as a bacterium. For instance, the enzyme having the RhaD activity of the invention may be a wild-type enzyme from a microorganism which belongs to a genus selected from Enterobacteriaceae as *Escherichia, Serratia, Silicibacter* and *Providencia*, from Firmicutes as *Lactobacillus, Listeria, Clostridium, Marvinbryantia, Mitsuokella, Streptococcus, Pediococcus, Carnobacterium, Geobacillus, Eubacterium, Acetonema* and from *Bacteroides*, CFB group bacteria as *Parabacteroides*, and *Fusobacteria*. For instance, FucA of the invention may be a wild-type enzyme from a microorganism which belongs to a genus selected from Enterobacteriaceae as *Escherichia, Shigella, Salmonella, Edwardsiella*, from Firmicutes as *Clostridia, Abiotrophia, Lachnoanaerobaculum, Paenibacillus* and *Streptococcus*, and from Proteobacteria as *Actinobacteria, Haemophilus, Sodalis, Mannheimia* and *Rhodospirillum*. TagA of the invention may be a wild-type enzyme from a microorganism which belongs to a genus selected from Enterobacteriaceae as *Escherichia, Shigella, Edwardsiella, Enterobacter, Salmonella, Pectobacterium, Providencia* from Enterobacterales as *Citrobacter, Yersinia, Photorhabdus*, from Vibrionales as *Vibrio, Photobacterium*, from Aeromonadales as *Aeromonas*, from Firmicutes as *Clostridia*.

In some other embodiments, the enzyme of the invention is a variant of a wild-type enzyme. Said wild-type enzyme comprises an amino acid sequence preferably selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and SEQ ID:35, optionally from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO17, SEQ ID NO:18, SEQ ID NO: 19, SEQ ID NO:20, SEQ ID NO:21, SEQ ID NO:22, and SEQ ID NO:23. In some embodiments, the enzyme is a variant of a wildtype enzyme. For instance, the enzyme may be variant having an amino acid sequence which differs from an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and SEQ ID:35 in virtue of 1 to 40 amino acid modifications, preferably from 1 to 20 amino acid modifications, namely by 1, 2, 3, 4, 5, 6, 7, 8, 9, 10, 11, 12, 13, 14, 15, 16, 17, 18, 19 or 20 amino acid modifications, optionally from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO17, SEQ ID NO:18, SEQ ID NO:19, SEQ ID NO:20, SEQ ID NO:21, SEQ ID NO:22, and SEQ ID NO:23. As mentioned above in the "definition section", amino acid modifications encompass insertion, deletion and substitution. In some embodiments, the amino acid modifications are conservative whereby the properties of the mutant are similar to those of its parent. In some other embodiments, the variant displays modified properties as compared to its parent enzyme, for example a modified solubility in aqueous medium and/or in solvent medium, an improved stability to pH, temperature and/or organic solvent, an improved class II DHAP activity, for instance an improved RhaD activity, an improved FucA activity, or an improved TagA activity, optionally an improved RhaD activity or an improved FucA activity, and/or a modified regioselectivity or stereoselectivity as compared to the parent enzyme. The methods for obtaining variants of a given enzyme are well-known in the art. Some of them are cited herein in the "Definition" section.

In some further embodiments, the enzyme of the invention is a hybrid polypeptide which means that said enzyme comprises a first polypeptide having the enzymatic activity of interest, e.g. a RhaD activity, a FucA activity or a TagA activity, optionally a RhaD activity or a FucA activity, which is fused or conjugated to another chemical or biochemical entity. The chemical or biochemical entity can be fused or conjugated to the N- or C-terminus region of the first polypeptide.

In some embodiments, the hybrid enzyme comprises a first polypeptide having the enzymatic activity of interest which is fused to an additional polypeptide. Said additional polypeptide can be selected in order to enhance the stability of the enzyme, to promote the secretion (such as a N-terminal hydrophobic signal peptide) of the hybrid enzyme from a cell (such as a bacterial cell or a yeast cell), or to assist in the purification of the hybrid enzyme. More particularly, the additional region can be a tag useful for purification or immobilization of the hybrid enzyme. Such a tag is well-known by the person skilled in the art, for instance a His tag ($His_6$), a FLAG tag, a HA tag (epitope derived from the Human influenza protein haemagglutinin), a maltose-binding protein (MPB), a MYC tag (epitope derived from the human proto-oncoprotein MYC), streptavidin or avidin, or a GST tag (small glutathione-S-transferase).

A conjugated polypeptide refers to a polypeptide wherein the amino acid sequence has been conjugated by chemical means to at least one chemical or biochemical entity. Techniques for conjugating an amino acid sequence to another chemical or biochemical entity are well-known in the art. The additional entity and the polypeptide having the enzymatic activity of interest may be covalently linked to each other directly or via a spacer. The spacer can be any standard linker commonly used for the preparation of polypeptide constructs. In some embodiments, the linker is a polypeptides comprising from 1 to 50 amino acid residues. Some preferred examples are Gly-Ser linkers such as tetraglycyl-seryl-triglycyl-serine peptide or polyalanine linkers.

The additional chemical or biochemical entities may be of any type. For instance, the additional or biochemical entities may be a mean useful for immobilizing the enzyme, e.g. a biotin or a reactive functional group, a mean for detecting the enzyme, a label and the like.

The enzyme having the enzymatic activity of interest, e.g. the RhaD activity, the FucA activity or the TagA activity, optionally the RhaD activity or the FucA activity, can be added in the reaction medium in a purified form or in a pre-purified form, for instance in the form of a clarified supernatant.

The enzyme may be present in a free state or immobilized on an appropriate support. After being isolated and purified, the enzyme of interest can be immobilized on a support by any appropriate method described in the state in the art, for instance, by covalent binding, adsorption, entrapment or membrane confinement. A wide variety of supports may be used for immobilizing the enzyme. Convenient supports encompass, without being limited to, plastic, metal, inorganic support such as glass, silica, alumina, bentonite, hydroxyapatite, nickel/nickel oxide, titanium, zirconia, polymeric supports and the like. The support may be in the form of a surface, a powder, micro- or nanobeads, a gel, a solvent-swelling or water-swelling gel or matrix, a reticulated matrix or gel, a membrane, a fibrous support, a porous support and the like. In a particular embodiment, the support is selected among inorganic matrices and polymeric matrices. For instance, supports useful for the invention encompass resins or matrices comprising or consisting in polyoside such as cellulose, carboxymethylcellulose, diethylaminocellulose (DEAE), dextran, cross-linked dextran such as Sephadex®, agarose, cross-linked agarose such as Sepharose®, starches, alginate, chitosan, a synthetic polymer such as polyaminoacids, polyacrylamides, polymers and copolymers based on acrylic acid and derivatives thereof, polyamides, polystyrene, organopolysiloxanes, polyacrylate, polyvinyls polyacrilin, inorganic compounds such as hydroxyapatite, silica or bentonite, and the like. Such supports are commercially available.

For illustration, the enzyme may be entrapped in a polymeric matrix, for instance a matrix of alginate or chitosan. As an alternative, the enzyme may be covalently linked to the support. Typically, the support may contain functional groups able to react directly, or after activation, with an amino acid present in the enzyme so as to create a covalent bound. As another alternative, the enzyme may be absorbed on the support. The interactions between the support and the enzyme may be then stabilized by cross-linking with a bifunctional agent such as glutaraldehyde.

Once prepared, the support comprising the immobilized enzyme having the enzymatic activity of interest can be directly used in the reaction medium. In other words, the support with the immobilized enzyme may be merely added in the reaction medium. When the support is solvent-swelling, the solvent of the reaction may be selected so as to provide an appropriate swelling of the support to render accessible the immobilized enzyme without impairing the catalytic activity of the enzyme.

Alternatively, the enzyme of the invention can be produced in situ, namely in the reaction medium, by a cell able to express said enzyme. The cell may naturally express the enzyme of interest or may have been recombinantly modified to express said enzyme of interest, whereby the cell is a host cell. The methods for introducing a foreign gene and inducing its expression in a host cell are well-known in the prior art.

In some embodiments, the cell secretes the enzyme of interest in the reaction medium. In other embodiments, the reaction of the invention, namely the reaction of DHAP with the ketone of formula (III) in the presence of the RhaD, the FucA or the TagA enzyme, optionally of the RhaD or FucA enzyme, is performed in cellulo. The cell may be of any type. In some embodiments, the cell is a recombinant prokaryotic or eukaryotic host cell. For instance, the host cell may be any Gram-negative or Gram-positive bacterium useful to produce homologous orheterologous RhaD, FucA or TagA enzyme of interest, optionally the RhaD or FucA enzyme. The host cell may also be a eukaryotic cell such as a mammalian, insect, plant, or fungal cell, in particular yeast cell. Host cells may be selected from *E. coli, Pseudomonas putida, Corynebacterium glutamicum, Bacillus subtilis, Lactobacillus plantarum, Streptomyces lividans, Acinetobacter baylyi* ADP1, *Kluyveromyces lactis, Saccharomyces cerevisiae, Pichia pastoris*, baculovirus- and infected insect cells.

In some other embodiments, the host cell overproduces DHAP. Several microorganisms are known to, or have been modified so as to, overproduce DHAP. For illustration, one can refer to M. Wei et al. ACS Catal. 2015, 5, 4060-4065, the disclosure of which being incorporated herein by reference.

In some other or alternate embodiments, the host cell produces, or has been modified to produce, an additional enzyme of interest, depending on the final product which is sought. Such enzyme may be selected among phosphatases, aldose isomerases or dehydrogenases.

In some other embodiments, the expression of the enzyme having the class II DHAP aldolase activity may be done by in vitro protein expression (also known as in vitro translation, cell-free protein expression, cell-free translation, or cell-free protein synthesis). In vitro protein expression systems based on *E. coli*, RRL (Rabbit Reticulose Lysate), wheat germ extracts and insect cells can be used.

DHAP

DHAP refers to dihydroxy acetone phosphate having the following formula:

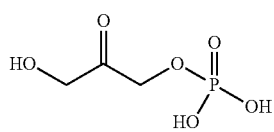

DHAP, is commercially available and can be added in the reaction medium or can be generated in situ. For instance, DHAP can be produced in situ from L-glycerol 3-phosphate by glycerol phosphate oxidase (GPO) or from fructose 1,6 biphosphate by fructose 1,6 biphosphate aldolase (FBA). Alternatively, DHAP can be prepared from dihydroxyacetone by reaction with a dihydroxyacetone kinase in the presence of ATP (see for instance R. Mahdi et al., ChemCatChem 2015, 7, 3110-3115). In situ production of DHAP is for instance described in Li et al. Biorganic & Medicinal Chemistry Letters, 2011, 21, 7081-7084 and in M. Wei, et al. ACS Catal. 2015, 5, 4060-4065.

When the enzyme of interest, e.g. the enzyme having a RhaD, a FucA or a TagA activity, optionally a RhaD or a FucA activity, is produced in situ by a host cell which is able to overproduce DHAP, the addition of external DHAP in the reaction medium may not be required.

In some embodiments, when the enzyme is added in the reaction medium, an analogue of DHAP may be used. For instance, DHAP may be replaced by adding, in the medium, dihydroxy acetone (DHA) with an anion able to mimic phosphate such as borate, arsenate and vanadate, phosphonate or methyl phosphate, preferably DHA in the presence of borate. Typically, DHA may be used instead of DHAP, in the presence of borate ester as described in Sugiyama, 2006, Adv. Synth. Catal., 348, 2555-2559. In such a case, the product of the reaction is not phosphorylated and thus corresponds to the dephosphorylated derivative of the compound of formula (I) or a cyclic hemiketal isomer thereof.

In a preferred embodiment, DHAP is added in the reaction medium.

Conditions to Implement the Reaction

As mentioned above, the enzyme having a class II DHAP aldolase activity, e.g. a RhaD aldolase activity, a FucA activity or the TagA activity, optionally a RhaD aldolase activity or a FucA activity, may be used in any appropriate forms, in particular those described herein. For instance, the enzyme may be provided in a free state, for example in an isolated form, in an enriched form, in a purified form or in a semi-purified form. For instance, said enzyme may be present in a supernatant or in a supernatant extract recovered from a culture. The enzyme may be provided as a cell lysate. Alternatively, the enzyme may be formulated in a composition. In some embodiments, the enzyme is immobilized on a support as described herein. In some other embodiments, the enzyme may be expressed in situ by a host cell, or by a cell which is able to endogenously express said enzyme.

In some embodiments, the method of the invention comprises:
(a) providing a product selected among the group consisting of an enzyme having a RhaD activity, a FucA activity or a TagA activity, optionally a RhaD activity or a FucA activity, a composition comprising said enzyme, a support on which an said enzyme is immobilized, and a cell or a host cell able to express said enzyme or a cell lysate thereof,
(b) contacting the product provided in step (a) with the DHAP and the ketone of formula (III), such as a ketone of (IIIa), or (IIIb), so as to promote the reaction of DHAP with the ketone to obtain the phosphorylated keto polyol, and
(c) optionally recovering and/or purifying the resulting phosphorylated keto polyol.

The running conditions may vary, among others, depending on the source of the enzyme which is used. When the enzyme is used in a free state, the pH, the temperature and the solvent are selected so as to promote enzymatic activity. When the enzyme is expressed in situ by a cell or a host cell, the running conditions may be conducive for the expression of the enzyme by said cell or host cell.

In some embodiments, the method of the invention is performed by adding the enzyme having RhaD, FucA or TagA activity in the reaction medium, optionally RhaD or FucA activity. Typically, the enzyme is contacting with DHAP and the ketone in conditions suitable for the enzyme activity. The enzyme may be in free state or immobilized on an appropriate support. DHAP may be added in the medium or generated in situ as described above. The reaction with DHAP, the ketone of formula (III) and the RhaD enzyme may be performed in the presence of a metallic divalent cation, such as $Co^{2+}$, $Zn^{2+}$, $Mn^{2+}$ or $Mg^{2+}$. Preferably the divalent cation is $Co^{2+}$. The divalent cation can be added in the medium as a salt such as cobalt chloride ($CoCl_2$). The solvent of the reaction may be any solvent convenient to perform the reaction and compatible with the enzyme. Typically the reaction may be performed in aqueous buffered solution or only in water. The pH of the aqueous buffered solution is typically from 6.5 to 8.5, for instance about 7.5.

Depending on the solubility of the ketone, the ketone may be firstly dissolved in an appropriate solvent such as DMF or DMSO and then added in the reaction medium.

The reagents, namely the enzyme, DHAP and the ketone, can be added in any order in the reaction medium. Preferably, the enzyme can be added at last. The ketone may be added in the reaction medium in the form of a hemiketal or a dimer thereof as in the case of dihydroxyacetone which may be added as a cyclic dimer. The molecular ratio of ketone to DHAP may be from 0.5 to 20 such as 1 to 15.

In some embodiments, the reaction may be performed under inert conditions, for instance under argon or nitrogen. Oxygen naturally dissolved in solutions may be removed prior to start the reaction, for instance when RhaD is used.

Additional Steps of the Method According of the Invention

The method of the invention may comprise one or several additional steps. For instance, the method of the invention may comprise a step of recovering the phosphorylated keto polyol of formula (I). The method may also comprise a step of purifying said phosphorylated keto polyol. Said compound may be purified by any method of purification known in the art such as precipitation, filtration, extraction, preparative chromatography, recrystallization and combinations thereof. In some particular embodiments, a chiral chromatography may be performed in order to eliminate unwanted stereoisomers. In an additional or alternate embodiment, the method of the invention may comprise a step of isomerizing the phosphorylated keto polyol into its cyclic hemiketal isomer. Typically, said isomerization can be performed spontaneously in aqueous solution.

The method of the invention may also comprise one or several steps prior to the step of reacting DHAP with the ketone in the presence of the RhaD aldolase, the FucA aldolase or the Tag aldolase, optionally the RhaD aldolase or the FucA aldolase. The method may comprise a step of preparing DHAP, for instance from DHA or L-glycerol-1-phosphate as described above, a step of providing the ketone of formula (III) and/or a step of providing the enzyme. The ketone of formula (III) may be commercially available or prepared by standard synthesis method. The enzyme may be prepared by any conventional methods, for instance by expression in a host cell followed by purification.

Uses of the Phosphorylated Keto Polyols of the Invention

The resulting phosphorylated keto polyols can be dephosphorylated so as to obtain keto polyols. Said keto polyols can be used as building blocks, in particular as chiral synthons, for the synthesis of a molecule of interest, such as pharmaceutical active ingredients. Indeed, the keto polyols of the invention comprise asymmetric carbons and a tertiary alcohol which are of high interest in the synthesis of pharmaceutical ingredients such as antibiotics. The keto polyols of the invention can also be used as starting materials or feedstock in fuel or chemical industries. The present invention thus also relates to a process for preparing a keto polyol of formula (II):

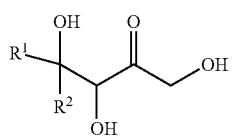
(II)

or a cyclic hemiketal isomer thereof, wherein $R^1$ and $R^2$ are as described above, said process comprises the steps of:
i. preparing a phosphorylated keto polyol of formula (I) thereof as described above, namely by reacting DHAP with a ketone of formula (III) in the presence of an enzyme with RhaD aldolase activity, a FucA aldolase activity or a TagA activity, optionally an enzyme with RhaD aldolase activity or a FucA aldolase activity
ii. Dephosphorylating the phosphorylated keto polyol of formula (I).

Typically, the step (i) corresponds to the method for preparing the phosphorylated keto polyol of formula (I) according to the invention, as fully described above. Preferred embodiments of step (i) thus correlate with those disclosed herein for the method for preparing the phosphorylated keto polyol of formula (I). In step (i), the phosphorylated keto polyol may be obtained as an acyclic compound, a cyclic hemiketal isomer, and mixtures thereof.

The step (ii) of dephosphorylation may be performed by any method known by the skilled artisan. In a preferred embodiment, step (ii) is performed by reacting the phosphorylated keto polyol obtained in step (i) with a phosphatase.

As used herein, "a phosphatase" refers to an enzyme, more precisely a hydrolase, able to remove a phosphate group from its substrate by hydrolysis, whereby a phosphate ion is released and the phosphate group in the substrate is replaced by a hydroxyl group. Phosphatases (EC 3.1.3.) encompass, without being limited to, sugar phosphatases (EC 3.1.3.23), acid phosphatases (EC 3.1.3.2) and alkaline phosphatases (EC 3.1.3.1).

For an article concerning phosphatases, one can refer to P. Clapés, X. Garrabou, Adv. Synth. Catal. 2011, 353, 2263-2283 or to Godinho L. M., de Sa-Nogueira I. FEBS J. 278:2511-2524 (2011), the disclosure of which being incorporated by reference.

In some embodiments, the phosphatase may be a naturally-occurring phosphatase isolated from any kind of organisms such as for instance E. coli, potato, wheat germ, calf intestine, bovine, porcine, human, sweet potato, shrimp, guinea pig, or may be a variant thereof.

In some particular embodiments, step (ii) of the process according to the invention is performed by reacting the phosphorylated keto polyol with a phosphatase, preferably with an acid phosphatase or a sugar phosphatase.

For illustration only, step (ii) may be performed by reacting the phosphorylated keto polyol of step (i) with an enzyme having a phosphatase activity and comprising a polypeptide having a sequence identity of at least 70%, with one of SEQ ID NO: 24 or SEQ ID NO:25. For instance, said enzyme comprises a polypeptide having at least 80%, 85%, 90%, 95% or 99% of sequence identity with SEQ ID NO: 24 or SEQ ID NO:25.

It goes without saying that in step (ii), the phosphatase may be used in any form known by the skilled artisan. The phosphatase may be provided in a free state, for example in an isolated form, in an enriched form, in a purified form or in a semi-purified form. For instance, the phosphatase may be present in a supernatant or in a supernatant extract recovered from a culture. The enzyme may be provided as a cell lysate. Alternatively, the phosphatase may be formulated in a composition. In some embodiments, the phosphatase is immobilized on a support as described herein for the enzyme having the RhaD activity, FucA activity or the TagA activity, optionally having the RhaD activity or the FucA activity. In some other embodiments, the enzyme may be produced in situ by a wild-type cell or a recombinant cell. It goes without saying that step (ii) is performed in conditions conducive for the phosphatase activity, for instance at an acidic pH.

Furthermore, the process for preparing a keto polyol according to the invention may comprise one or several additional steps. To that respect, said process may comprise one or several steps of purification which may be performed between step (i) and step (ii) or after step (iii). For instance, the process may comprise a step of separating the potential diastereoisomers or enantiomers of the phosphorylated keto polyol or those of the final keto polyol, and recovering the diastereoisomer or enantiomer of interest. Such a step may be performed by any standard purification process such as chromatography, chiral chromatography or recrystallization. Additionally and/or alternatively, the process may comprise one or several additional reaction steps occurring before step (i) (e.g. so as to prepare the ketone of formula (III) or so as to prepare DHAP in situ) and/or after step (ii).

In some embodiments, the keto polyol is selected from keto polyols of formula (IIa) and (IIb) as follows:

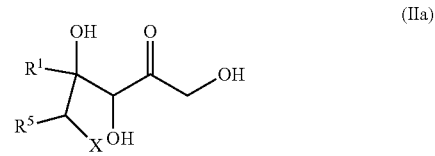
(IIa)

wherein $R^1$, $R^5$ and X are as defined above in formula (IIIa) and (Ia), and

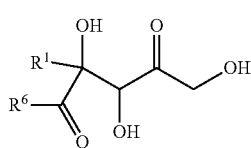

(IIb)

wherein R¹ and R⁶ are as defined above in formula (IIIb) or in formula (Ib).

The resulting keto polyol of formula (II), (IIa) or (IIb) and its phosphorylated precursor of formula (I), (Ia) or (Ib) can be used as building blocks or chiral synthons for preparing a compound of interest.

Thus, the invention also relates to a process for preparing a compound of interest comprising:
i. preparing a keto polyol of formula (II), a phosphorylated keto polyol of formula (I), or a hemiketal cyclic isomer thereof, said compound being prepared as described above and
ii. using the resulting keto polyol, the resulting phosphorylated keto polyol, the resulting hemiketal isomer thereof for producing the compound of interest.

The compound of interest may be of any type. The compound of interest may be a final product such as a drug. Alternatively, the compound of interest may be a building block or a synthesis intermediate which may be used for the synthesis of other molecules. For instance, the compound of interest may be a polyol, an amino polyol or a furfural derivative. The compound of interest may comprise at least one asymmetric carbon. In some embodiments, the process of the invention is preferably enantioselective or diastereoselective, this means that said method enables to obtain the compound of the interest in an enriched-enantiomeric or diastereoisomeric form, which means that a single enantiomer or diastereoisomer of the compound of interest is mostly obtained. Said diastereoisomer or enantiomer may account for at least 55%, 60%, 70%, 80%, 90%, 95%, 99%, even 99.9% in moles of the resulting compound of interest.

In some embodiments, step (i) comprises the preparation of a keto polyol of formula (II) or a cyclic hemiketal isomer thereof. Step (ii) may comprise several reaction sub-steps. For instance, in step (ii), the keto polyol of formula (II) or its isomer may undergo one or several of the following reaction steps:
- The reduction of one or several carbonyl groups present in the keto polyol into hydroxyl groups. Said step may be performed enzymatically with a dehydrogenase. Such a reaction may result in a polyol devoid of any carbonyl group.
- The reductive amination of the carbonyl group(s) of the keto polyol into amino groups. Such a step may be performed enzymatically by using a transaminase or an amino-oxidase. Such a step may lead to an amino polyol.
- The conversion of the keto polyol into an aldol by using an aldolase isomerase.
- The epimerization of the keto polyol so as to obtain a new diastereoisomer, by using for instance an epimerase, and
- The dehydration of the keto polyol so as to obtain a furfural derivative.

The invention also relates to a method for preparing a furfural derivative from a keto polyol of the invention by dehydration. Furfural derivatives, such as 4-hydroxymethylfurfural, can find uses in the preparation of liquid fuel. Indeed, 4-hydroxymethylfurfural is an intermediary in the liquid fuel for biomass. Furfural derivatives are also important building blocks and can be used as molecular platform to prepare a large variety of chemical compounds.

Thus, in another aspect, the invention relates to a method for preparing a furfural derivative of formula (IV):

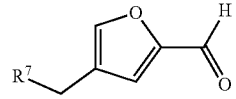

(IV)

wherein R₇ is H, OH or CH₃,
Said method comprising:
(i) The preparation a phosphorylated keto polyol of formula (Ia1)

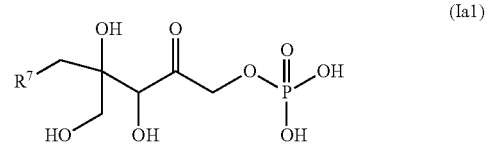

(Ia1)

or its cyclic hemiketal isomer,
by reacting a ketone of formula (IIIa1)

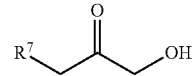

(IIIa1)

with DHAP in the presence of an enzyme having a RhaD, FucA, TagA aldolase activity, optionally having a RhaD or FucA aldolase activity,
(ii) The dephosphorylation of the compound obtained in step (i) so as to obtain the keto polyol of formula (IIa1)

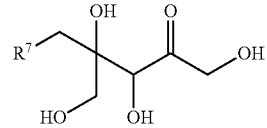

(IIa1)

or its cyclic hemiketal isomer
(iii) The dehydration of the compound of step (ii) so as to obtain the furfural derivative of formula (IV).

Steps (i) and (ii) are performed as described above.

The process may comprise an additional step aiming at isomerizing the compound of formula (Ia1) or (IIa1) into a cyclic hemiketal isomer, namely:

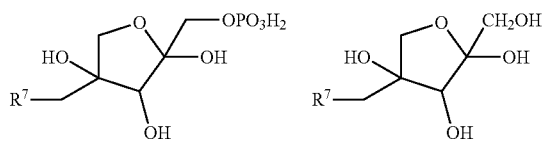

Alternatively, the process is devoid of such a step.

Step (iii) may be performed by any method of dehydration of keto polyols, in particular ketoses known in the art. The dehydration may be performed under acid condition, for instance by reacting the compound with sulfuric acid or acidic resin. For illustration, one can refer to patent application CN 103709127 or to Cui, et al. 2016, ACS Sustainable Chem. Eng., 4, 1707-1714.

The Phosphorylated Keto Polyols and the Derivatives Thereof

The invention also relates to the phosphorylated keto polyols of formula (I), (Ia) and (Ib) and cyclic hemiketal isomers thereof as described herein, per se, and to the keto polyols obtained from the dephosphorylation of said compounds.

In a particular embodiment, the compound of the invention is selected from:

a phosphorylated keto polyol of formula (I)

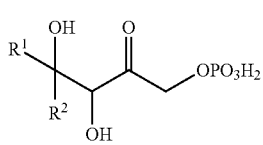

(I)

a keto polyol of formula (II)

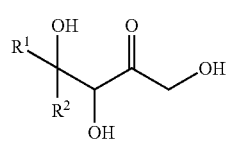

(II)

wherein $R^1$ and $R^2$ are such that the compound comprises a moiety (a') or (b') as defined above and $R^1$ and $R^2$ are independently selected from the group consisting of —$(CH_2)_p$-Ph, —OH, —$CH_2$—C(=O)—R, —COOH, —C(=O)—R, unsubstituted $C_1$-$C_3$ alkyl, $C_1$-$C_3$ alkyl substituted with at least one group selected from —OH,—$OCH_3$, and a halogen; wherein Ph is a phenyl, p is 1 or 2, and R is a $C_1$-$C_3$ alkyl; or $R_1$ and $R_2$ form together, with the carbon bearing the tertiary alcohol function, a $C_6$ ring bearing at least one group selected from —OH, —$OCH_3$, and a halogen at position alpha of the carbonyl group or bearing a second carbonyl group at position alpha or beta of the carbonyl group.

Preferred halogens are Cl and F.

In some embodiments, the invention relates to a compound selected from phosphorylated keto polyols of formula (I), (Ia) and (Ib), keto polyols of formula (II), (IIa) and (IIb), and cyclic hemiketal isomers thereof as well as salts thereof, with proviso that the compound is not the compound (1b) or (2b) or a cyclic hemiketal isomer thereof, as shown in Table 4 below.

In a particular embodiment, the invention relates to a keto polyol of formula (IIa) as defined above, or a cyclic hemiketal isomer or salt thereof with proviso that said keto polyol is not the compound (1b) or (2b) as shown in table 4 below.

In other embodiments, the invention relates to a compound selected from the compounds shown in the below table 4 and table 5, and cyclic hemiketal isomers thereof:

TABLE 4 examples of compounds of the invention

TABLE 4-continued
examples of compounds of the invention
| Particular phosphorylated keto polyol of formula (Ia) | Particular keto polyols of formula (IIa) |
|---|---|
| 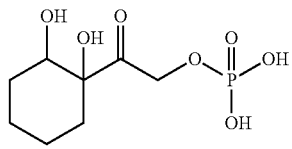<br>(4) | 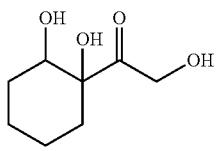<br>(4b) |
| 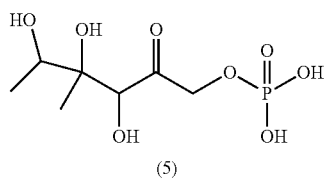<br>(5) | 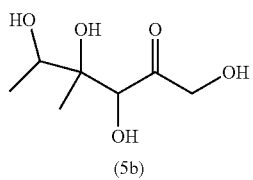<br>(5b) |
| 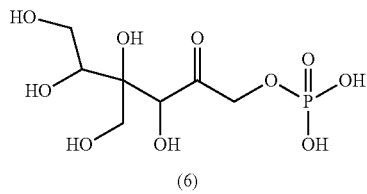 [SMILES: O=C(COP(=O)(O)O)C(O)C(O)(CO)C(O)CO]<br>(6) | 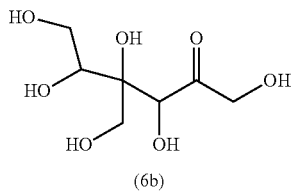 [SMILES: O=C(CO)C(O)C(O)(CO)C(O)CO]<br>(6b) |
| 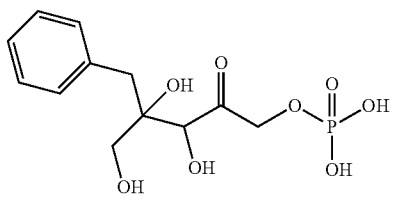<br>(7) | 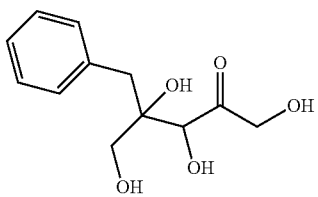<br>(7b) |
| 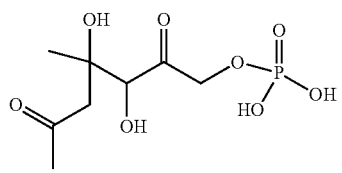<br>(8) | 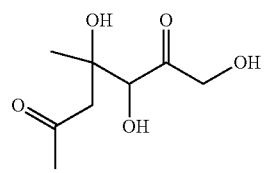<br>(8b) |
| 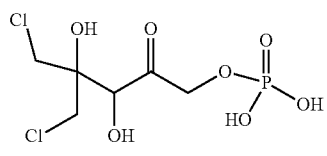<br>(9) | 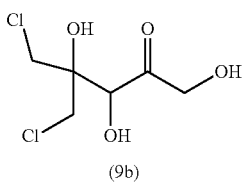<br>(9b) |

TABLE 5 examples of compounds of the invention

Particular phosphorylated keto polyols of formula (Ib)

(10)

(11)

(12)

Particular keto polyols of formula (IIb)

(10b)

(11a)

(12b)

Preferred compounds are compounds (1)-(12) and (3b)-(12b), in particular compounds (1), (2), (3), (6), (10), and cyclic hemiketal isomers and salts thereof Kits According to the Invention In another aspect, the invention relates to a kit for preparing a phosphorylated keto polyol of formula (I), said kit comprising:

A ketone of formula (III) as defined above,

An enzyme having a RhaD activity, a FucA activity or a TagA activity, optionally having a RhaD activity or a FucA activity, or a cell producing said enzyme thereof, Optionally, DHAP or a system to produce DHAP in situ.

In a further aspect, the invention relates to a kit for preparing a keto polyol of formula (II), said kit comprising:

A ketone of formula (III) as defined above,

An enzyme having a RhaD, aFucA, TagA activity, optionally having a RhaD activity or a FucA activity or a cell or a host cell producing said enzyme thereof, Optionally, DHAP or a system to produce in situ DHAP, and Optionally a phosphatase, preferably an acid phosphatase as sweet potato phosphatase or other sugar phosphatase.

The kits of the invention may comprise any additional component useful to carry out the enzymatic reaction, such as a solvent, a salt of a divalent metallic cation such as $CoCl_2$, a buffer, compounds required for culturing the cell or the host cell and the like. The kit may also comprise a mean for detecting or quantifying the progress of the reaction and/or written instructions, for instance, relating to the running conditions for preparing the compounds of interest.

The enzyme may be present in any form, preferably in purified form. The enzyme may be in free state or immobilized on an appropriate support as described above.

The kits of the invention are suitable to implement the method for preparing a phosphorylated keto polyol, or the process for preparing a keto polyol, according to the invention.

Further aspects and advantages of the present invention will be disclosed in the following experimental section, which should be regarded as illustrative and not limiting the scope of the present application.

List of Sequences

| SEQ ID NO: | Enzymes |
|---|---|
| 1 | Rhamnulose-1-phosphate aldolase (Uniprot Id: P32169) from *Escherichia coli* (strain K12) |
| 2 | Rhamnulose-1-phosphate aldolase (Uniprot Id: A0AFI3) from *Listeria welshimeri* serovar 6b (strain ATCC 35897/DSM 20650/SLCC5334) |
| 3 | Rhamnulose-1-phosphate aldolase (Uniprot Id: C0C0W7) from [*Clostridium*] *hylemonae* DSM 15053 |
| 4 | Rhamnulose-1-phosphate aldolase (Uniprot Id: C2JUR4) from *Lactobacillus rhamnosus* LMS2-1 |
| 5 | Rhamnulose-1-phosphate aldolase (Uniprot Id: D4E7Y8) from *Serratia odorifera* DSM 4582 |
| 6 | Rhamnulose-1-phosphate aldolase (Uniprot Id: C9Y4L9) from *Siccibacter turicensis* (strain DSM 18703/LMG 23827/z3032) |
| 7 | Rhamnulose-1-phosphate aldolase (Uniprot Id: D4BYG5) from *Providencia rettgeri* DSM 1131 |

-continued

| SEQ ID NO: | Enzymes |
|---|---|
| 8 | Rhamnulose-1-phosphate aldolase (Uniprot Id: C6LDG8) from *Marvinbryantia formatexigens* DSM 14469 |
| 9 | Rhamnulose-1-phosphate aldolase (Uniprot Id: C9KN12) from *Mitsuokella multacida* DSM 20544 |
| 10 | Rhamnulose-1-phosphate aldolase (Uniprot Id: Q8A1A0) from *Bacteroides thetaiotaomicron* (strain ATCC 29148/DSM 2079/NCTC 10582/E50/VPI-5482) |
| 11 | Rhamnulose-1-phosphate aldolase (Uniprot Id: I2B3W1) from *Shimwellia blattae* (strain ATCC 29907/DSM 4481/JCM 1650/NBRC 105725/CDC 9005-74) |
| 12 | Rhamnulose-1-phosphate aldolase (Uniprot Id: S0S6V8) from *Enterococcus avium* ATCC 14025 |
| 13 | Rhamnulose-1-phosphate aldolase (Uniprot Id: S0FM06) from *Clostridium termitidis* CT1112 |
| 14 | Rhamnulose-1-phosphate aldolase (Uniprot Id: U4TTI4) from *Lactobacillus shenzhenensis* LY-73 |
| 15 | Rhamnulose-1-phosphate aldolase (Uniprot Id: C6C3E9) from *Dickeya dadantii* (strain Ech703) |
| 16 | Rhamnulose-1-phosphate aldolase (Uniprot Id: A0A0B2WAC5) from *Pectobacterium carotovorum* subsp. *actinidiae* |
| 17 | Rhamnulose-1-phosphate aldolase (Uniprot Id: A0A127N812) from *Obesumbacterium proteus* DSM 2777 |
| 18 | Rhamnulose-1-phosphate aldolase (Uniprot Id: D3ADK3) from *Hungatella hathewayi* DSM 13479 |
| 19 | Rhamnulose-1-phosphate aldolase (Uniprot Id: D4KG04) from *Megamonas hypermegale* ART12/1 |
| 20 | Rhamnulose-1-phosphate aldolase (Uniprot Id: A0A011A6N3) from *Prevotella oryzae* DSM 17970 |
| 21 | Rhamnulose-1-phosphate aldolase (Uniprot Id: Q9X0G1) from *Thermotoga maritima* |
| 22 | L-fuculose-1-phosphate aldolase (Uniprot Id: P0AB87) from *Escherichia coli* (strain K12) |
| 23 | L-fuculose-1-phosphate aldolase (Uniprot Id: D5WVW4) from *Kyrpidia tusciae* DSM 2912 |
| 24 | Phosphatase (Uniprot Id: Q6FBP6) from *Acinetobacter baylyi* ADP1 |
| 25 | Phosphatase (Uniprot Id: P77475) from *Escherichia coli* (strain K12) |
| 26 | L-fuculose phosphate aldolase (Uniprot Id: P44777) from *Haemophilus influenzae* (strain ATCC 51907/DSM 11121/KW20/Rd) |
| 27 | Putative fuculose phosphate aldolase (Uniprot Id: C6JPX0) from *Fusobacterium varium* ATCC 27725 |
| 28 | Putative fuculose phosphate aldolase (Uniprot Id: D5U5S5) from *Brachyspira murdochii* (strain ATCC 51284/DSM 12563/56-150) |
| 29 | Putative fuculose phosphate aldolase (Uniprot Id: E3PVF1) from *Acetoanaerobium sticklandii* (strain ATCC 12662/DSM 519/JCM 1433/NCIMB 10654) |
| 30 | Putative fuculose phosphate aldolase (Uniprot Id: C0CS44) from *Blautia hydrogenotrophica* DSM 10507 |
| 31 | Putative fuculose phosphate aldolase (Uniprot Id: R2XFS7) from *Enterococcus gilvus* ATCC BAA-350 |
| 32 | Putative fuculose phosphate aldolase (Uniprot Id: B8ENG0) from *Methylocella silvestris* (strain BL2/DSM 15510/NCIMB 13906) |
| 33 | Putative fuculose phosphate aldolase (Uniprot Id: F7Z9Q2) from *Roseobacter litoralis* (strain ATCC 49566/DSM 6996/JCM 21268/NBRC 15278/OCh149) |
| 34 | Putative fuculose phosphate aldolase (Uniprot Id: Q3J3W1) from *Rhodobacter sphaeroides* (strain ATCC 17023/2.4.1/NCIB 8253/DSM158) |
| 35 | D-tagatose-1,6-bisphosphate aldolase subunit KbaY (Uniprot Id: P0AB74) from *Escherichia coli* (strain K12) |

EXAMPLES

Material and Methods

Cloning, Production and Purification of Enzymes

Genes were cloned and protein overexpressed in *E. coli* as previously described (Vergne-Vaxelaire et al., Adv. Synth. Catal. 2013, 355, 1763-1779). Each expression plasmid was transformed into *E. coli* (for example *E. coli* BL21-Codon-Plus (DE3)-RIPL). Cell culture, isopropyl β-D-thiogalactopyranoside (IPTG) induction of protein production and cell lysis were conducted as previously published (C. Guérard-Hélaine et al. ChemCatChem 2015, 7, 1871-1879).

The soluble fraction was applied totally to a Ni-NTA-agarose gel column according to the manufacturer's instructions (Qiagen) from 400 mL culture. After washing out any unbound proteins using buffer A, the adsorbed protein was eluted using buffer B (50 mM NaH$_2$PO$_4$, 300 mM NaCl, 250 mM imidazole pH 8). Samples were analyzed by SDS-PAGE using the NuPAGE system (Invitrogen). Protein concentrations were determined by the Bradford method, with bovine serum albumin as the standard (Bio-Rad). The fractions in which aldolase activity were grouped and dialyzed at 4° C. overnight against water. The dialyzed solution containing the protein was then lyophilized.

Detection of RhaD Aldolase Activity

Analytical assays (NADH) were performed as previously described. (I. Sanchez-Moreno et al. Adv. Synth. Catal. 2012, 354, 1725-1730 and F. Camps Bres et al. J. Mol. Catal.

B: Enzym. 2015, 114, 50-57), so as to check that the tested enzymes had RhaD activity. Aldolase activity using R1P as a substrate was measured under the following conditions: Reaction conditions: 50 mM Glygly (pH 8.0), 32 mM L-R1P, 0.2 mM NADH, 30 U GPDH, and 5 µL of aldolase in solution (2 mg/mL), optical absorbance at 340 nm measured at 30° C.

Detection of FucA Aldolase Activity

Analytical assays (NADH) were performed so as to check that the tested enzymes had FucA activity. Aldolase activity using L-F1P as a substrate was measured under the following conditions: Reaction conditions: 50 mM Glygly (pH 8.0), 32 mM L-F1P, 0.2 mM NADH, 30 U GPDH, and 5 µL of aldolase in solution (2 mg/mL), optical absorbance at 340 nm measured at 30° C.

Detection of TagA Aldolase Activity

Analytical assays (NADH) were performed so as to check that the tested enzymes had TagA activity. Aldolase activity using D-T1.6biP as a substrate was measured under the following conditions: Reaction conditions: 50 mM Glygly (pH 8.0), 32 mM D-T1.6biP, 0.2 mM NADH, 30 U GPDH, and 5 µL of aldolase in solution (2 mg/mL), optical absorbance at 340 nm measured at 30° C.

General Protocols for Ketones Screening and Results

Class II DHAP aldolases were produced and assayed as previously described (stock solution >50 mM, pH 2.5). I. Sanchez-Moreno, V. Hélaine, N. Poupard, F. Charmantray, B. Légeret, L. Hecquet, E. Garcia-Junceda, R. Wohlgemuth, C. Guérard-Hélaine, M. Lemaire, Adv. Synth. Catal. 2012, 354, 1725-1730.

Example 1: Assessment of Various RhaD Aldolases, FucA and TagA Aldolases for their Ability to Promote the Aldol Reaction of DHAP with Dihydroxyacetone (DHA)

Protocol for Assessing the Condensation Activity of the Enzyme

Aldolases were tested with DHAP as donor and DHA as acceptor. Cobalt ion (CoCl$_2$) to was added to optimize the activity. Conversion of the reactions was determined by assaying DHAP disappearance using triose-phosphate-isomerase coupled with α-glycerophosphate dehydrogenase enzymes. In addition the products of those reactions were analyzed by mass spectrometry. When the data from the two systems are in agreement, DHA is considered to be substrate of the enzyme.

Protocol (Analytical Scale Syntheses)

1 mg of aldolase (RhaD, FucA or TagA), 8 µmol of DHAP (123 µL of 65 mM solution), 8 µL CoCl$_2$ (10 mM), 10 eq of DHA and water to reach 200 µL final volume were added in a vial. The pH was adjusted to 7.5. The reaction mixture was gently stirred at RT for 5 h. DHAP disappearance was followed spectrophotometrically. The aldolase was removed by filtration over ultra-centrifugal filter unit (Amicon, 10 kDa). The reaction medium was directly analyzed by mass spectrometry (liquid chromatography (Alliance 2695—Waters) coupled to high resolution mass spectrometry (Micromass Q-TOF—Waters)).

Results

All the RhaD aldolases tested, namely aldolases of SEQ ID NO:1 to SEQ ID NO:21 were able to catalyse the reaction between DHAP and DHA to give a phosphorylated keto polyol of formula:

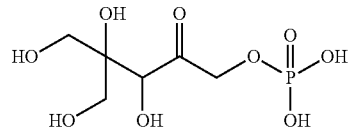

or its cyclic hemiketal isomer.

Noteworthy, these RhaD enzymes of SEQ ID NO: 1-21 displayed a high degree of dispersity in terms of amino acid sequence.

The same results were obtained with L-fuculose-1-phosphate aldolase (FucA) of SEQ ID NO:22-23, and 26-34. The same results were obtained with L-tagatose 1.6 biP aldolase (TagA) of SEQ ID NO:35.

Several aldolases which did not belong to class II DHAP aldolases, such as DHA aldolases (i.e. FSA of *E. coli*), deoc aldolase, class I DHAP aldolases and pyruvate aldolases (enzymes belonging to Pfam family PF03328) were also tested. Contrary to the RhaD aldolases, the FucA aldolases and the TagA aldolase these enzymes failed to catalyze the reaction between DHA and DHAP (data not shown).

Taken together, these results suggest that the ability to catalyze the reaction between DHAP and an activated ketone as acceptor substrate may be a specific feature of DHAP aldolases of EC 4.1.2.19 class (RhaD), EC 4.1.2.17 class (FucA) and EC 4.1.2.40 class (TagA).

Example 2: Screening of Ketones

Enzyme corresponding to SEQ ID No 10 was purified for deeper characterization and a scale up was performed to analyze the new branched sugars. This aldolase was tested with DHAP as donor and various ketones under argon conditions to avoid oxidation of DHAP and cobalt ion (CoCl2) to optimize the activity. Conversion of the various reactions was determined by assaying DHAP disappearance using triose-phosphate-isomerase coupled with ca-glycerophosphate dehydrogenase enzymes. In addition the products of those reactions were analyzed by mass spectrometry. When the data from the two systems are in agreement, the compound is considered to be substrate of the enzyme.

Protocol (Analytical Scale Syntheses)

Prior to the reaction, all the solutions and solids were degased by bubbling or circulating Ar. Under an Ar atmosphere, 1 mg of aldolase (SEQ ID NO: 10, 6.5 U), 8 µmol of DHAP (123 µL of 65 mM solution), 8 µL CoCl$_2$ (10 mM), 10 eq of electrophile (selected ketone) and water to reach 200 µL final volume were added in a vial. The pH was adjusted to 7.5. The reaction mixture was gently stirred at RT for 5 h. DHAP disappearance was followed spectrophotometrically. The aldolase was removed by filtration over ultra-centrifugal filter unit (Amicon, 10 kDa). The reaction medium was directly analyzed by mass spectrometry (liquid chromatography (Alliance 2695—Waters) coupled to high resolution mass spectrometry (Micromass Q-TOF—Waters)).

Results

The results are shown in the below tables:

TABLE 6

Examples of non-activated ketones which are not substrates.

| Acceptor | DHAP disappearance (%) | Expected mass (g/mol) | Measured mass (g/mol) |
|---|---|---|---|
| acetone | 0 | 227.0326 | Not determined—no reaction |
| butanone | 0 | 241.0483 | Not determined—no reaction |
| cyclopentanone | 0 | 253.0483 | Not determined—no reaction |
| 4-hydroxybutanone | 0 | 254.0432 | Not determined—no reaction |

TABLE 7

Reaction of DHAP with various acceptor substrates (activated ketones) using SEQ ID No 10.

| ketone | product | DHAP disappearance (%) | Expected mass (g/mol) | Measured mass (g/mol) |
|---|---|---|---|---|
| (dihydroxyacetone) | | 100 | 259.0224 | 259.0219 |
| (hydroxyacetone) | | 95 | 243.0275 | 243.0286 |
| (1-hydroxy-2-butanone) | | 84 | 257.0426 | 257.0427 |
| (2-hydroxycyclohexanone) | | 84 | 283.0588 | 283.0573 |
| (3-hydroxy-2-butanone) | | 96 | 257.0426 | 257.0270 |

TABLE 7-continued

Reaction of DHAP with various acceptor substrates (activated ketones) using SEQ ID No 10.

| ketone | product | DHAP disappearance (%) | Expected mass (g/mol) | Measured mass (g/mol) |
|---|---|---|---|---|
| [structure] | [structure] | 100 | 289.0325 | 289.0296 |
| [structure] | [structure] | 71 | 319.06 | 319.0545 |
| [structure] | [structure] | 83 | 269.0426 | 269.0404 |
| [structure] | [structure] | 92 | 273.0012 | 273.0004 |
| [structure] | [structure] | 75 | 257.0062 | 257.0079 |
| [structure] | [structure] | 100 | 255.0270 | 255.0271 |
| [structure] | [structure] | 72 | 294.9541 | 294.9539 |

This biochemical assays with SEQ ID NO: 10 revealed that 11 carbonyl compounds were acceptors when DHAP was the donor, with a structural variability in terms of chain (alicyclic, cyclic or aromatic) and functional groups (ketone, acid and alcohol). Moreover, these results further show that ketones devoid of any activating group at position alpha such as acetone, butanone, cyclopentanone, 4-hydroxybutan-2-one, were not acceptors of the enzymes.

Example 3: Small Scale Syntheses of Phosphorylated Keto Polyols and Characterization Thereof Protocol The protocol described in Example 2 was applied with the following quantities: 15 mg of aldolase (SEQ ID NO: 10, 93 U), 0.200 mmol of DHAP (3.1 mL, 65 mM), 200 µL CoCl$_2$ (10 mM), 5 eq (dihydroxyacetone, hydroxypyruvate or L-erythrulose) or 15 eq (hydroxyacetone or 1-hydroxybutanone) of electrophile and water to reach 5 mL final volume were mixed in a flask.

After 5 h, the phosphorylated keto polyol was purified directly by elution through an anionic resin (Dowex 1×8, bicarbonate form). After pouring the reaction medium on the column, the resin was first washed by 4 volumes of water. Then the aldol was eluted with 4 volumes of 0.33 M of $NH_4HCO_3$ except for the one bearing a carboxylic acid function (obtained from hydroxypyruvate) for which the elution was followed by 4 volumes of 0.66 M of $NH_4HCO_3$. The fractions were evaporated and washed with water and evaporated several times to remove $NH_4HCO_3$. TLC conditions were $NH_4OH$/EtOH 4/5.

Results.

The following products were isolated and characterized:

TABLE 8

| Product | Formula | Structure (mixtures of anomers and/or isomers) | Yield (%) |
|---|---|---|---|
| (1) | C6H12O9P | | 90 |
| (2) | C6H12O8P | | 85 |
| (3) | C7H14O8P | | 76 |
| (6) | C7H14O10P | presented as linear form | 92 |
| (10) | NaC6H9O10P | | 95 |

DHA+DHAP: Product (1), Mixture of Anomers, the Major One is Described $^1$H NMR (400 MHz, $D_2O$) δ 3.95 (s, 1H, H3), 3.88 (m, 2H, H6), 3.75 (m, 2H, H1), 3.55 (s, 2H, H5).

$^{13}$C NMR (101 MHz, $D_2O$) δ 102.44 (d, J=9 Hz, C2), 78.01 (C4), 72.86 (C6), 70.96 (C3), 65.68 (d, J=4 Hz, C1), 63.88 (C5).

HRMS ESI−: m/z calcd. for $[C_6H_{12}O_9P]$=259.0219; found 259.0278.

Hydroxyacetone+DHAP: Product (2), Mixture of Two Diastereoisomers $^1$H NMR (400 MHz, $D_2O$, pH 6.6) δ0 4.04-3.63 (m, 5H), 1.32 (s, 3H).

$^{13}$C NMR (101 MHz, $D_2O$, pH 6.6) δ 102.98 (d, J=8.9 Hz, C2'), 101.99 (d, J=10.3 Hz, C2), 78.70 (C4'), 77.90 (C3'), 76.11 (C4), 75.98 (C5), 75.61 (C5'), 74.24 (C3), 67.15 (d, J=4.4 Hz, C1'), 65.90 (d, J=4.6 Hz, C1), 20.93 (C6), 19.09 (C6').

HRMS ESI−: m/z calcd. for $[C_6H_1O_8P]$=243.0270; found 243.0286.

Ratio between the two isomers determined by NMR on the dephosphorylated sample (Isomer 3R,4R (65%)/Isomer 3R,4S(35%).

Hydroxybutanone+DHAP: Product (3), Only 1 Isomer: 3R,4R Isomer $^1$H NMR (400 MHz, $D_2O$, pH 7) δ 3.97 (s, 1H, H3), 3.94 (d, J=10.1 Hz, 1H, H7A), 3.84 (d, J=10.1 Hz, 1H, H7B), 1.71 (m, 2H, H5), 0.92 (m, 3H, H6).

$^{13}$C NMR (101 MHz, $D_2O$, pH 7) δ 102.16 (d, J=9.8 Hz, C2), 78.81 (C4), 74.74 (C7), 73.32 (C3), 65.81 (d, J=5.1 Hz, C1), 28.66 (C5), 7.32 (C6).

HRMS ESI−: m/z calcd. for $[C_7H_{14}O_8P]$=257.0426; found 257.0427.

Hydroxypyruvate+DHAP: Product (10), One Major Isomer: 3R, 4R Isomer $^1$H NMR (400 MHz, $D_2O$) δ 4.27 (s, 1H, H3), 4.17 (d, J=9.8 Hz, 1H, H6A), 3.74 (d, J=9.8 Hz, 1H, H6B), 3.80-3.65 (m, 2H, 2H1).

$^{13}$C NMR (101 MHz, $D_2O$) δ 177.76 (C5), 102.60 (d, J=10.0 Hz, C2), 82.39 (C4), 76.71 (C3), 73.78 (C6), 64.62 (d, J=4.5 Hz, C1).

HRMS ESI−: m/z calcd. for $[C_6H_{10}O_{10}P]$=273.0012; found 273.0004.

L-Erythrulose+DHAP: Product (6), Mixture of Hemiketal Isomers (with 3R,4R Configuration) in Equilibrium $^1$H NMR (400 MHz, $D_2O$) δ 4.2-3.4 (m, 8H)

$^{13}$C NMR (101 MHz, $D_2O$) δ 102.04 (d, J=8.9 Hz, C2), 98.20 (d, J=7.3 Hz, C2'), 97.56 (d, J=8.5 Hz, C2"), 79.45 (C4), 74.67 (C4'), 74.34 (C4"), 72.95 (C6), 72.57 (C5), 70.85 (C3), 69.29 (C3" or C6"), 68.39 (C3" or C6"), 66.39 (d, J=6.0 Hz, C1"), 66.20 (C6' or C3'), 66.03 (d, J=3.6 Hz, C1'), 65.66 (d, J=4.4 Hz, C1), 63.90 (C6' or C3'), 63.06 (C7' or C5'), 62.39 (C7" or C5"), 61.59 (C7), 61.29 (C7" or C5"), 58.67 (C7' or C5').

HRMS ESI−: m/z calcd. for $[C_7H_{14}O_{10}P]$=289.0325; found 289.0296.

Example 4: Validation by LCMS Orbitrap of the Phosphorylated Keto Polyols Obtained from 6 Ketones with the Enzymes of SEQ ID NO:1-10 (RhaD) and SEQ ID: 23 (FucA)

A mother solution was prepared by mixing DHAP (5.2 mL, 35 mM), $CoCl_2$ (200 μL, 10 mM), 5 to 10 eq of ketone, adjusted to pH 7.3 and degased under Ar. In 10 vials containing each 4 mg of enzyme to screen (beforehand degased under Ar) were added 400 μL of the mother solution. The reactions were gently stirred for 5 h at RT. The aldolase was removed by filtration over ultra-centrifugal filter unit (Amicon, 10 kDa). The reaction medium was analyzed by mass spectrometry.

LC/MS Validation

The detection of the compounds of interest was performed by LC/ESI-MS method using a Dionex TCC-3000RS chromatographic system (Thermo Fisher Scientific, Courtaboeuf, France) coupled to an ultra-high resolution Orbitrap Elite hybrid mass spectrometer ((Thermo Fisher Scientific, Courtaboeuf, France) equipped with a HESI source.

HPLC

A Sequant ZICpHILIC column 5 m, 2.1×100 mm (Merck, Darmstadt, Germany) thermostated at 15° C. was employed for HPLC separation. Mobile phase flow rate was set at 0.2 ml/min, and injection volume was 5 µl. Aqueous solution of 10 mM $(NH_4)_2CO_3$ (at a pH of 9.9 adjusted by $NH_4OH$) was used as phase A and acetonitrile was used as solvent B. The following gradient conditions were applied for elution: 1 min equilibration step at 80% of phase B; 7 min linear gradient from 80 to 40% of phase B; 3 min isocratic elution at 40% of B, return to 80% of phase B in 3 min and a reconditioning step of 8.5 min.

Mass Spectrometry

Mass and product ion spectra were recorded in the ESI negative ion mode. Ion spray (IS) was set at −4.5 kV and capillary temperature at 275° C. Sheath gas, auxiliary gas and sweep gas flow rates were set at 60, 10 and 0 arbitrary units, respectively. The mass resolution power of the detector was 60000.

Data Processing

Raw data were manually inspected using the Qualbrowser module of Xcalibur version 2.2 (Thermo Fisher Scientific, Courtaboeuf, France) for enzymes from SEQ ID NO:1 to 20 and SEQ ID NO:23 for DHAP+dihydroxyacetone, and for SEQ ID NO:1 to 10 for the other couples of reagents.

Results:

Theoretical mass products are reported in Table 9. For each couple of substrates and for each tested enzyme, the detected mass corresponded to the theoretical mass of the expected product with a mass deviation of 2 ppm in average. In other words, all the tested RhaD and the tested FucA were able to catalyze the reaction of DHAP with activated ketones such as butanedione, L-erythrulose, 2-hydroxycyclohexanone, dihydroxyacetone, hydroxyacetone, and hydroxypyruvate to form the expected products.

TABLE 9

Theoretical mass product

| Reaction | Theoritical mass product |
|---|---|
| DHAP + butanedione | 255.02753 |
| DHAP + L-erythrulose | 289.03301 |
| DHAP + 2-hydroxycyclohexanone | 283.05883 |
| DHAP + dihydroxyacetone | 259.02244 |
| DHAP + hydroxyacetone | 243.02753 |
| DHAP + hydroxypyruvate | 273.00171 |

Example 5: Dephosphorylation of the Phosphorylated Keto Polyol Obtained from DHAP and HA with SEQ ID NO:10

Protocol

Dephosphorylation was done with acid phosphatase as previously described (F. Camps Bres et al. *J. Mol. Catal. B: Enzym.* 2015, 114, 50-57)).

The reaction was carried out in water (10 mL, pH 4,8) containing the phosphorylated compound (0.4 mmol). The acid phosphatase from sweet potato (60 mg) was added to the solution which was kept under stirring for 48 h. The vanishing of the phosphorylated compound can be followed by TLC (4/5 $NH_4OH$/EtOH, vanillin as revelator).

TABLE 10 results of dephosphorylation

| Product | Structure (mixtures of anomers and/or isomers) | Yield (%) |
|---|---|---|
| (1b) | | 91% |
| (2b) | | 85 |
| | | |

Dephosphorylated Sample (1b): Idem Literature: Major Form $^1$H NMR (400 MHz, $D_2O$) δ 3.98 (s, 1H, H3), 3.94 (m, 2H, H6), 3.60 (1s, 2H, H5), 3.55 (m, 2H, H1).

$^{13}$C NMR (101 MHz, $D_2O$) δ 103.11 (C2), 78.18 (C4), 73.02 (C6), 70.40 (C3), 63.81 (C1), 62.57 (C5)

Dephosphorylated Sample (2b)

$^1$H NMR (400 MHz, $D_2O$) δ 3.98 (d, J=10.0 Hz, 1H, H5A), 3.93 (s, 1H, H3'), 3.89 (s, 1H, H3), 3.86 (d, J=9.7 Hz, 1H, H5'A), 3.77 (d, J=10.0 Hz, 1H, H5B), 3.74 (d, J=9.7 Hz, 1H, H5'B), 3.64 (d, J=11.9 Hz, 1H, H1'A), 3.61 (d, J=11.9 Hz, 1H, H1'B), 3.59 (d, J=12.0 Hz, 1H, H1A), 3.55 (d, J=12.0 Hz, 1H, H1B), 1.34 (s, 3H, $CH_3$), 1.33 (s, 3H, $CH_3$').

$^{13}$C NMR (101 MHz, $D_2O$) δ 104.11 (C2'), 103.03 (C2), 78.94 (C4'), 77.90 (C3'), 76.30 (C4), 76.07 (C5), 75.63 (C5'), 74.03 (C3), 64.26 (C1'), 62.80 (C1), 21.06 (C6), 19.08 (C6').

The invention claimed is:

1. A method for preparing a phosphorylated keto polyol of formula (I)

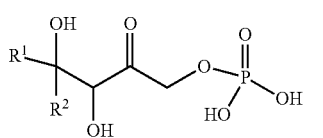
(I)

or a cyclic hemiketal isomer thereof, comprising a step of reacting dihydroxyacetone phosphate (DHAP) with a ketone of formula (III) selected from a 1,2-diketone and a ketone having a substituent X at a position alpha of the carbonyl group:

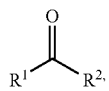
(III)

in the presence of a class II DHAP aldolase, wherein $R^1$ and $R^2$ are such that:

the molecular weight of the ketone of formula (III) is less than 600 g.mo$^{-1}$, neither $R^1$ nor $R^2$ are H, and the carbonyl group shown in formula (III) is included in a moiety selected from:

(b)

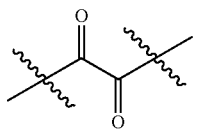

and (a)

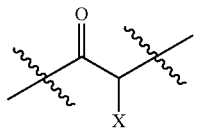

wherein X is selected from the group consisting of
OH, F, Cl, Br, I, —N$_3$, cyano, nitro, —COOH, —SO$_3$H, —C(F)$_3$, —C(Cl)$_3$, —C(Br)$_3$, —C(I)$_3$, —NHC(=O)R, —NHC(=O)OR, —OR, —SR, —SO$_2$R, —C(=O)R, —C(=O)OR, —C(=O)NHR, —OC(=O)OR, —C(=O)SR, wherein R is a substituted or unsubstituted C$_1$-C$_{10}$ alkyl, a substituted or unsubstituted C$_5$-C$_{10}$ aryl or a substituted or unsubstituted C$_4$-C$_{10}$ heteroaryl group,
—N(R$^3$)$_3$$^+$ wherein each R$^3$ is independently selected from H, C$_1$-C$_{10}$ alkyl and C$_5$-C$_{10}$ aryl,
OP(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted C$_5$-C$_{10}$ aryl, a substituted or unsubstituted C$_4$-C$_{10}$ heteroaryl group, substituted or unsubstituted C$_1$-C$_{10}$ alkoxy and substituted or unsubstituted C$_5$-C$_{10}$ aryloxy.

2. The method of claim 1, wherein the ketone of formula (III) is characterized in that:
R$^1$ and R$^2$ are independently selected from the group consisting of —(CH$_2$)$_p$-Ph, —COOH, —C(=O)—R, —CH$_2$—C(=O)—R, —C(=O)OR, and C$_1$-C$_{10}$ alkyl, optionally substituted with at least one group selected from —OH, C$_1$-C$_3$ alkoxy, C$_1$-C$_3$ alkyl, —F, —Cl, —Br, —I, wherein:
Ph is a phenyl optionally substituted by one or several substituents selected from halogens, —OH, C$_1$-C$_6$ alkyl, and C$_1$-C$_6$ alkoxy,
p is an integer from 1 to 6, and
R is a C$_1$-C$_6$ alkyl optionally substituted by one or several substituents selected from halogens, —OH, C$_1$-C$_3$ alkyl, and C$_1$-C$_3$ alkoxy, or
R$^1$ and R$^2$ form together, with the carbonyl group, a C$_5$-C$_6$ ring bearing at least one group selected from —OH, —OCH$_3$, —F, —Cl, —Br, —I, at position alpha of the carbonyl group or a second oxo group at position alpha or beta of the carbonyl group.

3. The method of claim 1, wherein the ketone of formula (III) is such that:
R$^1$ and R$^2$ are independently selected from the group consisting of —(CH$_2$)$_p$-Ph, wherein Ph is a phenyl, and p is 1 or 2; COOH; —CH$_2$—C(=O)—R, —C(=O)—R wherein R is a C$_1$-C$_3$ alkyl; C$_1$-C$_6$ alkyl optionally substituted with at least one group selected from —OH, —OCH$_3$ and —Cl, or
R$^1$ and R$^2$ form together, with the carbonyl group, a C$_6$ ring bearing at least one group selected from —OH, —OCH$_3$, and —Cl at position alpha of the carbonyl group or bearing a second oxo group at position alpha or beta of the carbonyl group.

4. The method of claim 1, wherein the ketone of formula (III) is selected from ketones of formula (IIIa):

(IIIa)

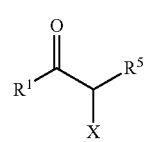

wherein X is selected from the group consisting of:
OH, F, Cl, Br, I, —N$_3$, cyano, nitro, —COOH, —SO$_3$H, —C(F)$_3$, —C(Cl)$_3$, —C(Br)$_3$, —C(I)$_3$, —NHC(=O)R, —NHC(=O)OR, —OR, —SR, —SO$_2$R, —C(=O)R, —C(=O)OR, C(=O)NHR, —OC(=O)OR, —C(=O)SR, wherein R is a substituted or unsubstituted C$_1$-C$_{10}$ alkyl, a substituted or unsubstituted C$_5$-C$_{10}$ aryl or a substituted or unsubstituted C$_4$-C$_{10}$ heteroaryl group,
—N(R$^3$)$_3$$^+$ wherein each R$^3$ is independently selected from H, C$_1$-C$_{10}$ alkyl and C$_5$-C$_{10}$ aryl, and
OP(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted C$_5$-C$_{10}$ aryl, a substituted or unsubstituted C$_4$-C$_{10}$ heteroaryl group, substituted or unsubstituted C$_1$-C$_{10}$ alkoxy and substituted or unsubstituted C$_5$-C$_{10}$ aryloxy,
P(=O)(R$^4$)$_2$ and P(=O)(R$^4$)$_2$ wherein each R$^4$ is independently selected from H, a substituted or unsubstituted C$_1$-C$_{10}$ alkyl, a substituted or unsubstituted C$_5$-C$_{10}$ aryl, a substituted or unsubstituted C$_4$-C$_{10}$ heteroaryl group, substituted or unsubstituted C$_1$-C$_{10}$ alkoxy and substituted or unsubstituted C$_5$-C$_{10}$ aryloxy,
R$^1$ and R$^5$ are such that:
R$^1$ and R$^5$ form together, with the moiety (a), a C$_5$-C$_6$ ring optionally bearing at least one additional substituent, said additional substituent being selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl, or
R$^1$ and R$^5$ are independently selected from the group consisting of H, —OH, —(CH$_2$)$_p$-Ph, unsubstituted C$_1$-C$_6$ alkyl, and substituted C$_1$-C$_6$ alkyl wherein:
R$^1$ is not H,
p is an integer from 1 to 6,
Ph is a phenyl group optionally substituted by one or several groups selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl,
the substituted C$_1$-C$_6$ alkyl comprises at least one substituent selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)

(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl.

5. The method of claim 4, wherein:

X is selected from —OH, —OCH$_3$, a halogen, and C(=O)CH$_3$,

R$^1$ and R$^5$ are independently selected from H, C$_1$-C$_6$ alkyl, C$_1$-C$_6$ alkyl substituted by 1 to 6 substituents selected from C$_1$-C$_3$ alkoxy, C$_1$-C$_3$ haloalkyl, F, Cl, Br, I and OH; and —CH$_2$-Ph optionally bearing at least one substituent selected from F, Cl, Br, I, —OH, C$_1$-C$_3$ alkyl, C$_1$-C$_3$ haloalkyl, and C$_1$-C$_3$ alkoxy;

with proviso that R$_1$ is not H, or

R$^1$ and R$^5$ form together with the moiety (a), a C$_5$-C$_6$ ring optionally bearing at least one additional substituent selected from —OH, C$_1$-C$_3$ alkyl, C$_1$-C$_3$ haloalkyl, F, Cl, Br, I and C$_1$-C$_3$ alkoxy.

6. The method of claim 1, wherein ketone of formula (III) is selected from ketones of formula (IIIb):

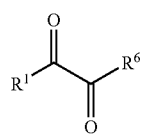

(IIIb)

wherein:

R$^1$ and R$^6$ are independently selected from the group consisting of —OH, C$_1$-C$_6$ alkyloxy, —(CH$_2$)$_p$-Ph, unsubstituted C$_1$-C$_6$ alkyl, and substituted C$_1$-C$_6$ alkyl wherein:

p is an integer from 1 to 6,

Ph is a phenyl group optionally substituted by one or several substituents selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl, the substituted C$_1$-C$_6$ alkyl comprises at least one substituent selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl; or R$^1$ and R$^6$ forms, together with the moiety (b), a C$_5$-C$_6$ ring optionally bearing an additional substituent selected from NH$_2$, OH, F, Cl, Br, I, —N$_3$, cyano, nitro, SH, —CONH$_2$, —COOH, —SO$_3$H, —C(F)$_3$, C$_1$-C$_3$ alkyl, C$_1$-C$_3$ alkoxy, C$_1$-C$_3$ alkylamino, C$_1$-C$_3$ aminoalkyl, C$_1$-C$_3$ N,N-dialkylamino alkyl, C$_1$-C$_3$ N-alkylamino alkyl, OP(=O)(OH)$_2$, —SO$_3$H, C$_1$-C$_3$ hydroxyalkyl, C$_1$-C$_3$ haloalkyl, C$_1$-C$_3$ alkylthio, and C$_1$-C$_3$ thioalkyl.

7. The method of claim 1, wherein the enzyme belongs to EC 4.1.2.19, to EC 4.1.2.17 or to EC 4.1.2.40.

8. The method of claim 7, wherein:

the enzyme has RhaD aldolase activity and comprises a polynucleotide having at least 30% of sequence identity with an amino acid sequence selected from SEQ ID NOs:1-21, the enzyme has FucA aldolase activity and comprises a polynucleotide having at least 30% of sequence identity with an amino acid sequence selected from SEQ ID NO:22, SEQ ID NO:23 or SEQ ID NOs:26-34, or the enzyme has TagA aldolase activity and comprises a polynucleotide having at least 50% of sequence identity with SEQ ID NO:35.

9. The method of claim 7, wherein the enzyme is a purified enzyme, and/or is present in free form, and/or is immobilized on a solid support.

10. The method of claim 7, wherein the reaction medium contains a metallic divalent cation.

11. The method of claim 1, said method further comprising a step of recovering and/or purifying the phosphorylated keto polyol of formula (I).

12. A process for preparing a keto polyol of formula (II):

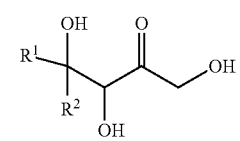

(II)

or a cyclic hemiketal isomer thereof, said process comprising preparing a phosphorylated keto polyol of formula (I) according to the method of claim 1 and dephosphorylating the phosphorylated keto polyol.

13. The process of claim 12, wherein the dephosphorylation step is performed by contacting the phosphorylated keto polyol with a phosphatase.

14. A process for preparing a compound of interest comprising:

preparing a keto polyol of formula (II) by the process as defined in claim 12 and using the resulting keto polyol keto polyol for producing the compound of interest.

15. The process of claim 14, wherein the compound of interest is a building block for chemical synthesis or a drug.

16. A process for preparing a compound of interest comprising:

preparing a phosphorylated keto polyol of formula (II) by the process as defined in claim 1 and using the resulting phosphorylated keto polyol for producing the compound of interest.

17. The process of claim 16, wherein the compound of interest is a building block for chemical synthesis or a drug.

* * * * *

UNITED STATES PATENT AND TRADEMARK OFFICE
CERTIFICATE OF CORRECTION

PATENT NO. : 11,466,298 B2
APPLICATION NO. : 16/615427
DATED : October 11, 2022
INVENTOR(S) : Véronique De Berardinis et al.

It is certified that error appears in the above-identified patent and that said Letters Patent is hereby corrected as shown below:

In the Specification

Column 50,
Lines 47-48, "with ca-glycerophosphate" should read --with α-glycerophosphate--.

Column 56,
Line 10, "[$C_6H_1O_8P$]" should read --[$C_6H_{12}O_8P$]--.

Column 57,
Line 4, "column 5 m," should read --column 5 µm,--.

In the Claims

Column 110,
Line 63, "600 g.mo$^{-1}$," should read --600 g.mol$^{-1}$,--.

Signed and Sealed this
Fifteenth Day of August, 2023

Katherine Kelly Vidal
*Director of the United States Patent and Trademark Office*